United States Patent
Wiedman et al.

(10) Patent No.: US 11,939,402 B2
(45) Date of Patent: Mar. 26, 2024

(54) ANTIFUNGAL PEPTIDES, COMPOUNDS INCLUDING THE SAME, AND METHODS OF USE THEREOF

(71) Applicants: Seton Hall University, South Orange, NJ (US); Rutgers, The State University of New Jersey, New Brunswick, NJ (US)

(72) Inventors: Gregory R. Wiedman, New Milford, NJ (US); Robert J. Tancer, Montville, NJ (US); Chaoyang Xue, Livingston, NJ (US)

(73) Assignees: Seton Hall University, South Orange, NJ (US); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 18/128,062

(22) Filed: Mar. 29, 2023

(65) Prior Publication Data
US 2023/0312650 A1     Oct. 5, 2023

Related U.S. Application Data

(60) Provisional application No. 63/324,909, filed on Mar. 29, 2022.

(51) Int. Cl.
| | | |
|---|---|---|
| C07K 7/00 | (2006.01) | |
| A61K 38/12 | (2006.01) | |
| A61P 31/10 | (2006.01) | |
| C07K 7/08 | (2006.01) | |

(52) U.S. Cl.
CPC ............... *C07K 7/08* (2013.01); *A61K 38/12* (2013.01); *A61P 31/10* (2018.01)

(58) Field of Classification Search
CPC ............ C07K 7/08; A61K 38/12; A61P 31/10
See application file for complete search history.

(56) References Cited

FOREIGN PATENT DOCUMENTS

WO     WO-2012009790 A1 *  1/2012  ............. A61K 39/12

OTHER PUBLICATIONS

Bogan, A A, and K S Thorn. "Anatomy of hot spots in protein interfaces." Journal of molecular biology vol. 280,1 (Jul. 1998): 1-9. doi: 10.1006/jmbi.1998.1843. 9 pgs.

Greco, I., Molchanova, N., Holmedal, E. et al. "Correlation between hemolytic activity, cytotoxicity and systemic in vivo toxicity of synthetic antimicrobial peptides". Sci Rep 10, 13206 (Aug. 2020). https://doi.org/10.1038/s41598-020-69995-9. 13 pgs.

Hiraizumi, Masahiro et al. "Cryo-EM structures capture the transport cycle of the P4-ATPase flippase." Science (New York, N.Y.) vol. 365,6458 (Sep. 2019): 1149-1155. doi: 10.1126/science.aay3353. 7 pgs.

Maligie, Marybeth A, and Claude P Selitrennikoff. "Cryptococcus neoformans resistance to echinocandins: (1,3)beta-glucan synthase activity is sensitive to echinocandins." Antimicrobial agents and chemotherapy vol. 49,7 (Jul. 2005): 2851-6. doi:10.1128/AAC.49.7.2851-2856.2005. 6 pgs.

Liou, Angela Y et al. "Identification and functional analyses of disease-associated P4-ATPase phospholipid flippase variants in red blood cells." The Journal of biological chemistry vol. 294,17 (Mar. 2019): 6809-6821. doi:10.1074/jbc.RA118.007270. 13 pgs.

Manno, Sumie et al. "Identification of a functional role for lipid asymmetry in biological membranes: Phosphatidylserine-skeletal protein interactions modulate membrane stability." Proceedings of the National Academy of Sciences of the United States of America vol. 99,4 (Feb. 2002): 1943-8. doi:10.1073/pnas.042688399. 6 pgs.

Huang W, et al. "Lipid Flippase Subunit Cdc50 Mediates Drug Resistance and Virulence in Cryptococcus neoformans". mBio. May 2016;7(3) e00478-16. doi: 10.1128/mbio.00478-16. 13 pgs.

Gates, Marcellene A et al. "Molecular architecture of the Cryptococcus neoformans capsule." Molecular microbiology vol. 52,1 (Apr. 2004): 13-24. doi: 10.1111/j.1365-2958.2003.03957.x. 12 pgs.

Stanchev, Lyubomir Dimitrov et al. "P-Type ATPase Apt1 of the Fungal Pathogen Cryptococcus neoformans Is a Lipid Flippase of Broad Substrate Specificity." Journal of fungi (Basel, Switzerland) vol. 7,10 843. Oct. 8, 2021, doi: 10.3390/iof7100843. 16 pgs.

Andersen, Jens P et al. "P4-ATPases as Phospholipid Flippases—Structure, Function, and Enigmas." Frontiers in physiology vol. 7 275. Jul. 8, 2016, doi:10.3389/fphys.2016.00275. 23 pgs.

Tadini-Buoninsegni, Francesco et al. "Phosphatidylserine flipping by the P4-ATPase ATP8A2 is electrogenic". Proceedings of the National Academy of Sciences. vol. 116, No. 33, 16332-16337, (Aug. 2019)https://doi.org/10.1073/pnas.1910211116. 6 pgs.

Konarzewska, Paulina et al. "Phosphatidylserine synthesis is essential for viability of the human fungal pathogen Cryptococcus neoformans." The Journal of biological chemistry vol. 294,7 (Jan. 2019): 2329-2339. doi:10.1074/jbc.RA118.006738. 11 pgs.

Tancer, RJ, et al. "Synergy among humimycins against methicillin-resistant *Staphylococcus aureus*". Peptide Science. (Oct. 2020); 113:e24197. https://doi.org/10.1002/pep2.24197. 6 pgs.

(Continued)

*Primary Examiner* — Jeanette M Lieb
(74) *Attorney, Agent, or Firm* — Lerner David LLP

(57) ABSTRACT

An antifungal peptide targeting P4-ATPase function is synthesized based on Cdc50 loop region to identify peptides sensitize caspofungin by blocking flippase function. It was found that myristylated peptides based on "AS15 sequence" was effective at high concentrations. A modified peptide, "AW9-Ma" showed minimum inhibitory concentration (MIC) of 64 μg/mL against H99 wild type and fractional inhibitory concentration (FIC) index value of 0.5 when used with caspofungin. With the AW9-Ma peptide, *C. neoformans* wild type was highly sensitive to caspofungin with a MIC of 4 μg/mL, the same as cdc50Δ mutant. Further assays with flow cytometry showed inhibition of lipid flippase enzyme activity and significant accumulation of phosphatidylserine on the cell surface. It was confirmed that the peptide co-localized with mCherry-tagged P4-ATPase protein Apt1 in *C. neoformans*. Modification studies of AW9 sequence showed that two lysine residues on the peptide are likely responsible for interaction with P4-ATPasee critical for antifungal activity.

Figure 1:
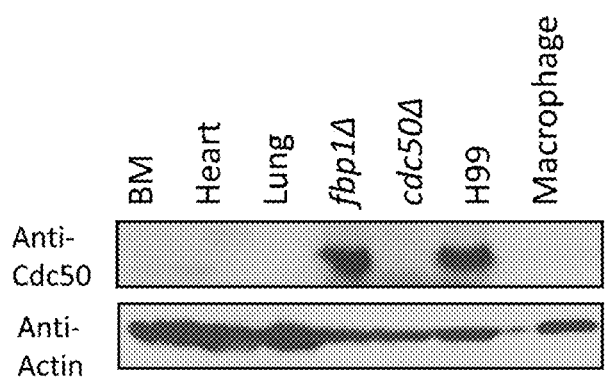

22 Claims, 5 Drawing Sheets
(4 of 5 Drawing Sheet(s) Filed in Color)

(56) References Cited

OTHER PUBLICATIONS

Odds, F C. "Synergy, antagonism, and what the chequerboard puts between them." The Journal of antimicrobial chemotherapy vol. 52,1 (Jun. 2003): 1. doi:10.1093/jac/dkg301. 1 pg.
Segawa, Katsumori et al. "The CDC50A extracellular domain is required for forming a functional complex with and chaperoning phospholipid flippases to the plasma membrane." The Journal of biological chemistry vol. 293,6 (Dec. 2017): 2172-2182. doi:10.1074/jbc.RA117.000289. 11 pgs.
Nakanishi, Hanayo et al. "Transport Cycle of Plasma Membrane Flippase ATP11C by Cryo-EM." Cell reports vol. 32,13 (Sep. 2020): 108208. doi: 10.1016/j.celrep.2020.108208. 19 pgs.
Chan, David I et al. "Tryptophan- and arginine-rich antimicrobial peptides: structures and mechanisms of action." Biochimica et biophysica acta vol. 1758,9 (Apr. 2006): 1184-202. doi:10.1016/j.bbamem.2006.04.006. 19 pgs.

\* cited by examiner

ANTIFUNGAL PEPTIDES, COMPOUNDS INCLUDING THE SAME, AND METHODS OF USE THEREOF

CROSS-REFERENCE TO RELATED APPLICATION

The present application claims the benefit of the filing date of U.S. Provisional Patent Application No. 63/324,909 filed Mar. 29, 2022, the disclosures of which are hereby incorporated herein by reference.

FIELD OF THE DISCLOSURE

The present disclosure relates to an antifungal peptide targeting a protein from the organism *Cryptococcus neoformans*. More particularly, the peptide comprises at least nine amino acids from the cdc50 protein with or without modifications at the terminal amino groups and terminal carboxyl groups to work in synergy with existing classes of drugs, including but not limited to, the triazole class (Itraconazole), the polyene class (Amphotericin B), Poly-L-Lysine, and/or Chlorhexidine.

BACKGROUND

It is well known that cryptococcosis is the leading cause of meningitis in adults living with HIV. In 2008, the number of cryptococcal meningitis (CM) cases in the sub-Saharan Africa region alone was estimated to be 720,000 (range 144,000-1.3 million). Worldwide the proportion of AIDS-related deaths due to *Cryptococcus* remains one of the most common causes of AIDS-related mortality in adults. Cryptococcal infection is believed to be acquired by inhalation of fungal cells from the environment. In immunocompetent hosts, the pathogen can be cleared or establish a latent infection.

In immunocompromised patients, *Cryptococcus* may induce pneumonia and its dissemination to the central nervous system (CNS) causes meningitis, the most severe form of the infection, which is fatal without appropriate treatment. In low income countries, the one-year mortality of CM, even in HIV-infected patients in care, has been estimated to be as high as 70%. Human cryptococcal infections were traditionally attributed to *Cryptococcus neoformans* until *Cryptococcus gattii* was classified as a distinct species by molecular methods in 2002.

*Cryptococcus neoformans* remains a problematic caspofungin resistant fungus which is the most concerning for immunocompromised patients such as people with HIV/AIDS, those undergoing cancer chemotherapy or transplantation. *C. neoformans* is the leading cause of fungal meningitis in HIV/AIDS patients and is responsible for ~15% AIDS related deaths each year. The treatment options for fungal infections are limited to only three available drug classes: triazoles, polyenes (amphotericin B), and echinocandins. Of these classes, triazoles are fungistatic and amphotericin B is fungicidal yet highly toxic. Echinocandins are the newest fungicidal drug class with fewer side-effects against a variety of invasive fungal infections, but are inactive against cryptococcosis therefore not a treatment option for patients with such a challenging prognosis.

Echinocandins are a class of drugs that inhibit the (1,3)-β-D glucan synthase, a ubiquitous fungal enzyme that is responsible for polymerizing the carbohydrate component of the fungal cell wall. Inhibiting this process leads to apoptosis of cells. The understanding of *Cryptococcus* resistance mechanism to echinocandins has been incremental. It was proposed that one or more of three possibilities are responsible: (i) the target itself is resistant; (ii) caspofungin is excluded from cells; or (iii) caspofungin is degraded. Previous investigators were able to show, in an optimized in vitro assay, that the (1,3)-β-D glucan synthase was sensitive to echinocandins. Their work suggested that the enzyme itself is not likely responsible for the apparent drug resistance and, additionally, that caspofungin is not rapidly degraded by *C. neoformans*.

Recently, mutation studies discovered an essential role of *Cryptococcus* lipid flippase in echinocandin resistance. The lipid flippase is composed of the core P4 type ATPase (P4-ATPase) and a regulatory subunit Cdc50. The same study found that fungal mutants deleted CDC50 gene or its 250 amino acid exocytoplasmic loop region were highly sensitive to caspofungin. This loop region of Cdc50 has been reported in other organisms to bind to the P4-ATPase to regulate flippase activity. The minimum inhibitory concentration (MIC) value of caspofungin in the wild-type strain H99 was decreased in cdc50Δ from 16 μg/mL to 4 μg/mL. The P4-ATPase flippase is responsible for translocating exoplasmic phosphatidylserine (PS) to the intracellular side of the cell membrane. Within these mutants, an increase in cell-surface PS was found to correlate to an increase in echinocandin sensitivity in broth microdilution MIC assays.

Therefore, there is an urgent need to identify novel drug targets and develop new antifungals. There is also a need to develop a drug that would allow for targeted, increased *C. neoformans* sensitivity to echinocandin drug caspofungin. The de novo design of effective new drugs is exceedingly expensive and challenging. There is also a need for a more reasonable approach to examine the resistance mechanisms of microbes, and ameliorate the resistance with rationally designed drugs that counteract the resistance mechanism, and potentiating the drug's effectiveness.

SUMMARY

Compared to the above prior attempts, the present disclosure fulfills the above criteria and provides additional benefits that state of the art attempts cannot provide. In accordance with embodiments of the present disclosure, an antifungal peptide targeting a protein from the organism *Cryptococcus neoformans* has been developed. The peptide comprising at least nine amino acids and preferably no more than nine amino acids from the cdc50 protein with or without modifications at the terminal amino groups and terminal carboxyl groups. Preferably, the C-terminus chain may or may not contain a fluorescent marker.

In addition the peptide contains an acid tail C-terminus tail in which a 14 Carbon chain was unexpectedly found to work best for antifungal properties. Additional carbon atoms on the terminus chain was shown not to improve the antifungal properties as well as decreasing the carbon chain below a 14 carbon chain. Binding of the drug to the fungal protein causes charged lipid molecules to be retained on the surface. This peptide works in synergy with the existing antifungal drug caspofungin. Echinocandin drugs like caspofungin are one of the few classes of existing antifungals. Due to the high concentrations needed, caspofungin is rarely used to treat *C. neoformans* infections. The peptide provides a way to lower the concentration of caspofungin needed to treat such infections, thus opening the possibility for greater utility of these antifungal.

Moreover, the peptide disclosed herein may work in synergy with existing classes of drugs, such as The triazole class (Itraconazole), the polyene class (Amphotericin B), Poly-L-Lysine, and/or Chlorhexidine.

The present inventors hypothesized that peptides that could interfere with the P4-ATPase activity of *C. neoformans* would increase the sensitivity to caspofungin. Such peptides would prove to be a novel combinational therapeutic agent together with echinocandins like caspofungin.

Furthermore, the present inventors identified a peptide in the loop region of the Cdc50 protein that produced an antibody showed strong binding to the protein in a whole cell assay. The inventors generated a stable peptide based on the sequence by adding a lipid tail. Antifungal activity tests showed that a nine amino acid peptide significantly increased the fungicidal activity of caspofungin in *C. neoformans*. Peptide treatment leads to increased surface PS exposure. The results herein demonstrated that this peptide could act as a peptide-based inhibitor for fungal lipid flippase function and antifungal development.

Thus, one objective is to develop a drug that would allow for targeted, increased *C. neoformans* sensitivity to echinocandin drug caspofungin. The de novo design of effective new drugs is exceedingly expensive and challenging.

Another objective is to examine the resistance mechanisms of microbes, and ameliorate the resistance with rationally designed drugs that counteract the resistance mechanism, potentiating the drug's effectiveness.

Yet another objective is to examine a possible mechanism addressing exclusion as a route to increase caspofungin sensitivity in *C. neoformans* because the enzyme itself is not likely responsible for the apparent drug resistance and, additionally, that caspofungin is not rapidly degraded by *C. neoformans*.

Any combination and/or permutation of the embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, reference is made to the following Detailed Description, considered in conjunction with the accompanying drawings, in which:

FIG. 1. Western blot analysis of a Cdc50 antibody. Antibodies were tested for its binding to total proteins from animal tissues (BM, Heart and Lung), *Cryptococcus neoformans* cells (H99, fbp1Δ, cdc50Δ), and murine macrophages in SDS-PAGE. The signal detected by an Anti-actin antibody was used as a protein loading control.

FIG. 2. Structure of the peptides AS15 and QY15. These sequences were selected because of their antigenic properties in the development of Anti-cdc50 antibodies. AS15-derived antibodies were found to be active against *C. neoformans* protein isolates whereas QY15-derived antibodies were not active (data not shown).

FIG. 3. Hemolysis caused by proteins and caspofungin (Caspo) at varying concentrations in μg/mL. Each sample tested against human RBC at $5*10^8$ cells/mL. Fractional lysis was determined with respect to a control of 1 μL of Triton X-100 added to control wells.

FIG. 4. Flow cytometry data of *C. neoformans* exposed to peptides AS15-Ma and AW9-Ma. Cells were gaited first to ensure only singlets were collected (4A) and then for morphology (4B) Data were collected and gaited for signal as indicated (4C). Finally, the distribution of counts (in relative units, RU) in that region was determined (4D).

FIG. 5*a*-5*b*. Sensitivity of peptide-treated fungal cells to SDS. Relative CFUs are shown above. Growth of the indicated strains was conducted in YPD media and SDS-modified media (A). Colony dilution assays were conducted for strains with the associated treatment in YPD or YPD+0.03% SDS. The error bars indicate standard deviations for three experiments. ***, P<0.001 (determined by ordinary one-way ANOVA).

FIG. 6. Imaging of FITC-AW9-Ma peptide co-localization with Apt1:mCherry. The FITC labeled AW9-Ma peptide was added to the fungal strain expressing Apt1:Cherry fusion protein for 10 min before observed under fluorescent microscope. The insert area of the images was highlighted at the bottom of each image. Bar, 10 μm.

FIG. 7. Structure of homologous lipid flippase-Cdc50 loop (7BSU) interaction. The 14.0 Å distance between Cdc50 loop region and phosphatidylserine in the flippase protein with green (flippase), purple (Cdc50), blue (phosphatidylserine) are highlighted.

FIG. 8. Histogram of Annexin V Signal Counts in *C. neoformans* treated with peptides. Cells were treated using the same methods as for the active peptides. Relative counts (RU) of annexin V signal were recorded. Signal for the peptides is relatively close to baseline.

FIG. 9. Possible mechanism of action of Cdc50 and P4-ATPase in *C. neoformans*. Fungal loop region interacts with the peptide in a manner to facilitate the turnover of a region in the peptide (dark red) which allows for the movement of lipids from exofacial to internal.

FIG. 10. Proposed mechanism of action of antifungal peptides. Peptides bind to P4-ATPase through hydrogen bonding interactions with charged residues, this prevents the turnover of the region responsible for lipid flipping.

DETAILED DESCRIPTION

As previously described, *Cryptococcus neoformans* is a major fungal pathogen that often causes life-threatening meningitis in immunocompromised populations. This yeast pathogen is highly resistant to the echinocandin drug caspofungin. Previous studies showed that *Cryptococcus* lipid translocase (flippase) is required for the caspofungin resistance of that fungus. Mutants with a deleted subunit of lipid flippase, Cdc50, showed increased sensitivity to caspofungin.

Shown and described herein is an antifungal peptide targeting the P4-ATPase function. The present inventors synthesized stable peptides based on the Cdc50 loop region to identify peptides that can sensitize caspofungin by blocking flippase function and found that myristylated peptides based on the "AS15 sequence" was effective at high concentrations. A modified peptide, "AW9-Ma" showed a minimum inhibitory concentration (MIC) of 64 μg/mL against H99 wild type and a fractional inhibitory concentration (FIC) index value of 0.5 when used in combination with caspofungin.

Most notably, in the presence of the AW9-Ma peptide, *C. neoformans* wild type was highly sensitive to caspofungin with a MIC of 4 μg/mL, the same as the cdc50Δ mutant. Further assays with flow cytometry showed inhibition of the lipid flippase enzyme activity and significant accumulation of phosphatidylserine on the cell surface.

Using a fluorescently labelled peptide, it was confirmed that the peptide co-localized with mCherry-tagged P4-ATPase protein Apt1 in *C. neoformans*. Modification studies of the AW9 sequence showed that two lysine residues on the peptide are likely responsible for the interaction with the P4-ATPase, hence critical for its antifungal activity.

Described herein is now examples that further illustrate the principles of the present invention. It is noted that these examples are merely given to further illustrate the principles of the invention. The scope of the invention is therefore not intended to be limited to these examples but the examples merely given to illustrate the invention.

Peptide Design

The present inventors designed a peptide based on a portion of the outer loop region from the Cdc50 protein. The *C. neoformans* capsules and cell wall are thick multicomponent systems, that provide a barrier preventing large molecules from binding to its target. Peptides are low molecular weight molecules that are potentially less excluded from the cell than larger antibody fragments. The present inventors selected regions of the Cdc50 outer loop that were confirmed to be exposed in H99 spheroplasts using anti-Cdc50 antibodies and identified one polyclonal antibody that showed positive signal in a western blot assay.

Figure 2:
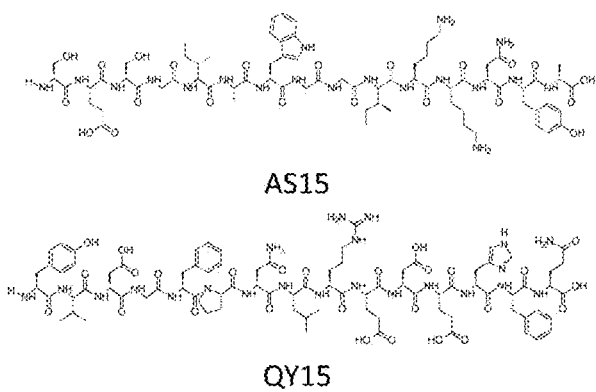

This AS15 peptide-based antibody was shown to target total protein extracts from H99 cells while also not labelling the cdc50Δ mutant total protein extract nor animal cells or macrophages (FIG. 1). The binding regions (AS15 and Qy15) for two antibodies (one positive and one negative in Western blot) were shown below and are part of the fungal Cdc50 loop (FIG. 2).

The present inventors hypothesized that peptides based on these sequences could disrupt the Cdc50 interaction with P4-ATPase to block the flippase function, hence making *C. neoformans* susceptible to caspofungin, similar to the cdc50Δ mutant.

Previously work found that myristic acid-modified peptides are able to work synergistically with other antimicrobial drugs. The present inventors hypothesized that a lipid tail would be essential for interaction with a lipid-flipping enzyme. The present inventors synthesized and characterized both lipidated and non-lipidated versions of these AS15 and QY15 peptides. Such flippase inhibitors could slow the growth of *C. neoformans*, and also improve the activity of caspofungin.

Given the apparent importance of the flippase activity for caspofungin sensitivity, the inventors created and tested a series of peptides with different fatty acid tail (FAT) lengths to determine the ideal length for activity. Then a series of myristylated peptides with reduced amino acid counts were made to determine which section of the peptide was most important for flippase binding (Table 1).

TABLE 1

Sequence Names and Structures of antifungal peptides studied.

| N' lipidation | Name | Mass |
| --- | --- | --- |
| None | AS15 | 1580.76 |
| Ma C14 | AS15-Ma | 1791.13 |
| None | QY15 | 1865.98 |
| Ma C14 | QY15-Ma | 2076.34 |
| Acetic C2 | AS15-Ac | 1622.80 |
| Hexanoic C6 | AS15-Ha | 1678.91 |
| Decanoic C10 | AS15-Da | 1733.94 |
| Palmitic C16 | AS15-Pa | 1819.18 |
| Ma C14 | AW9-Ma | 1246.56 |
| Ma C14 | KS9-Ma | 1098.40 |
| Ma C14 | GS9-Ma | 1072.27 |
| Palmitic C16 | AW9-Pa | 1274.62 |

Each peptide name is displayed along with any possible C terminal modifications (Ac, acetic acid; Ha, hexanoic acid; Da, decanoic acid; Ma, myristic acid; and Pa, palmitic acid).

The chemical structures of the peptides in Table 1 and other related peptides are the following:

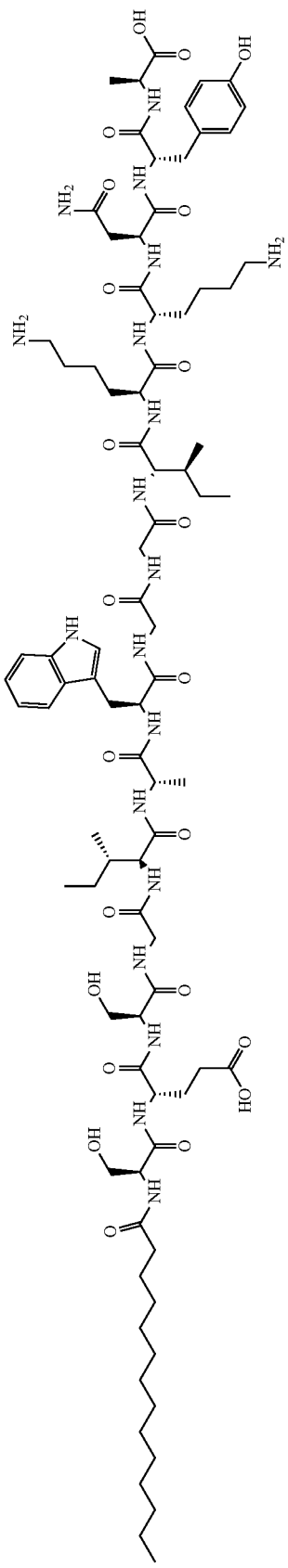
AS15-Ma
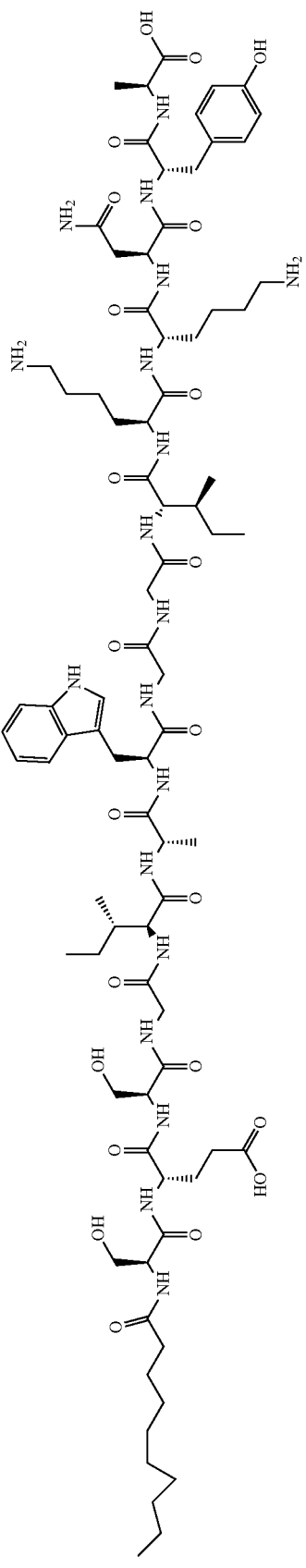
AS15-Da
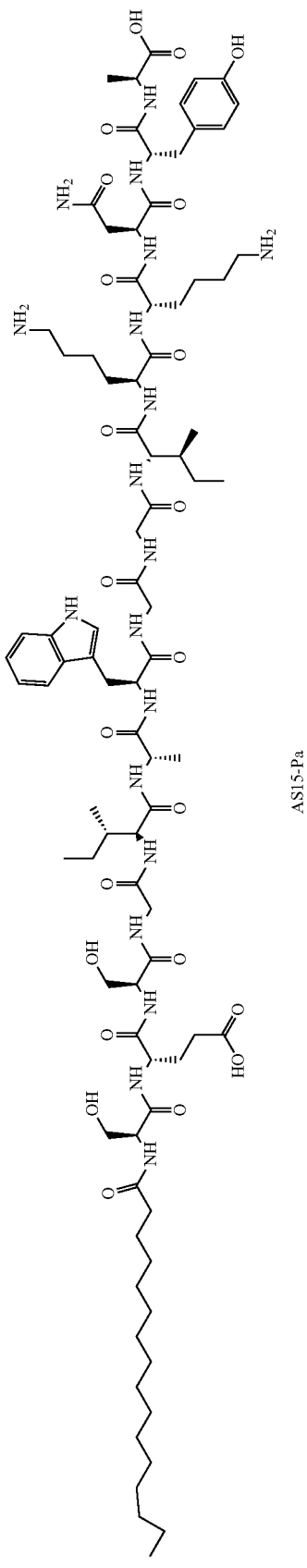
AS15-Pa

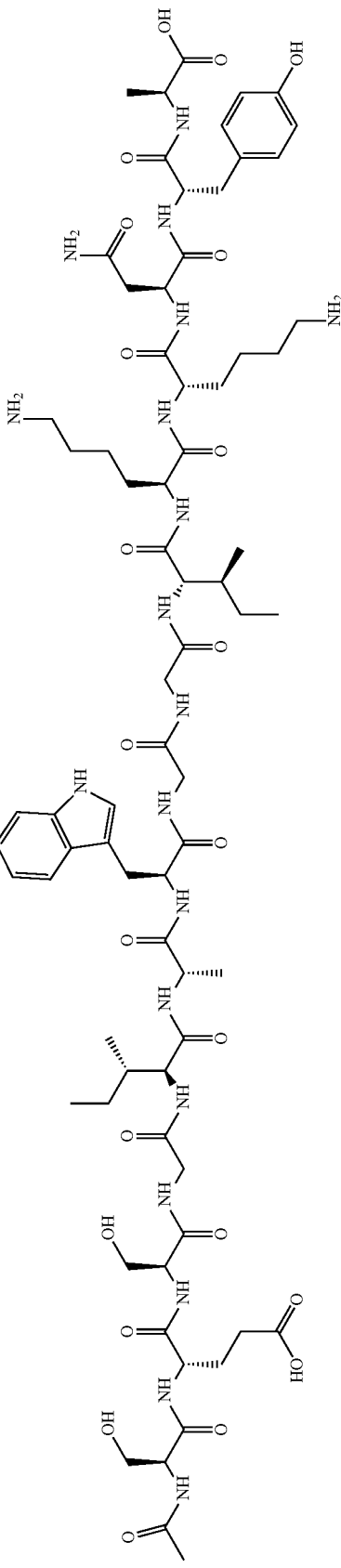
AS15-Ac
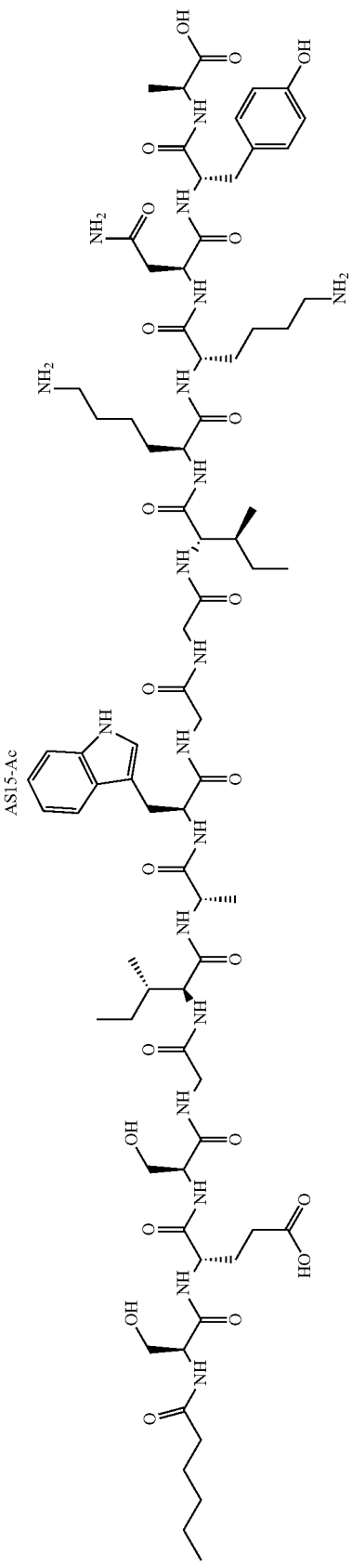
AS15-Ha
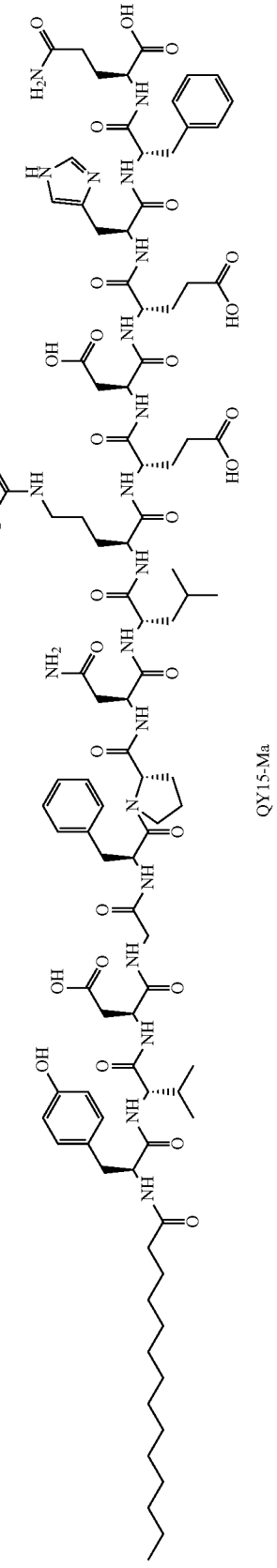
QY15-Ma

-continued
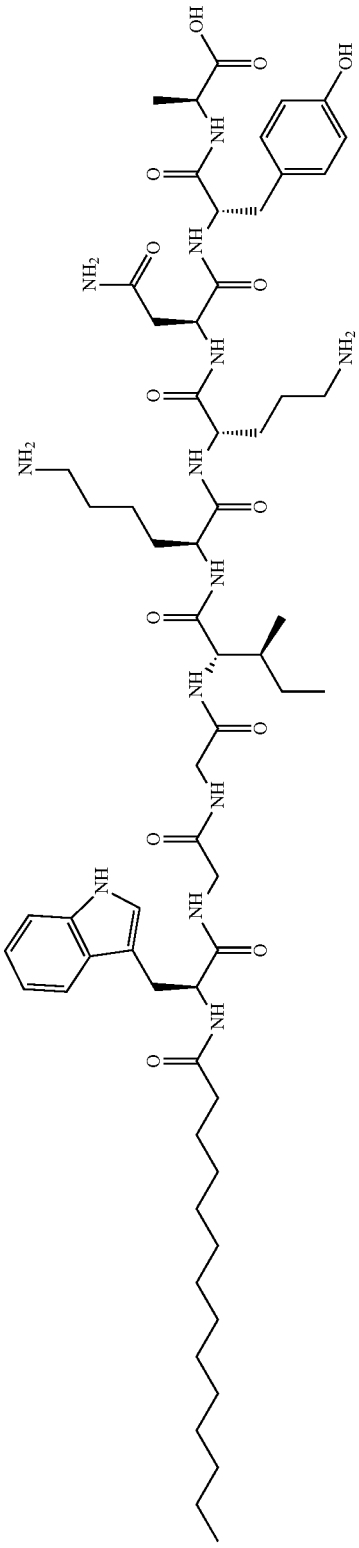
AW9-Ma
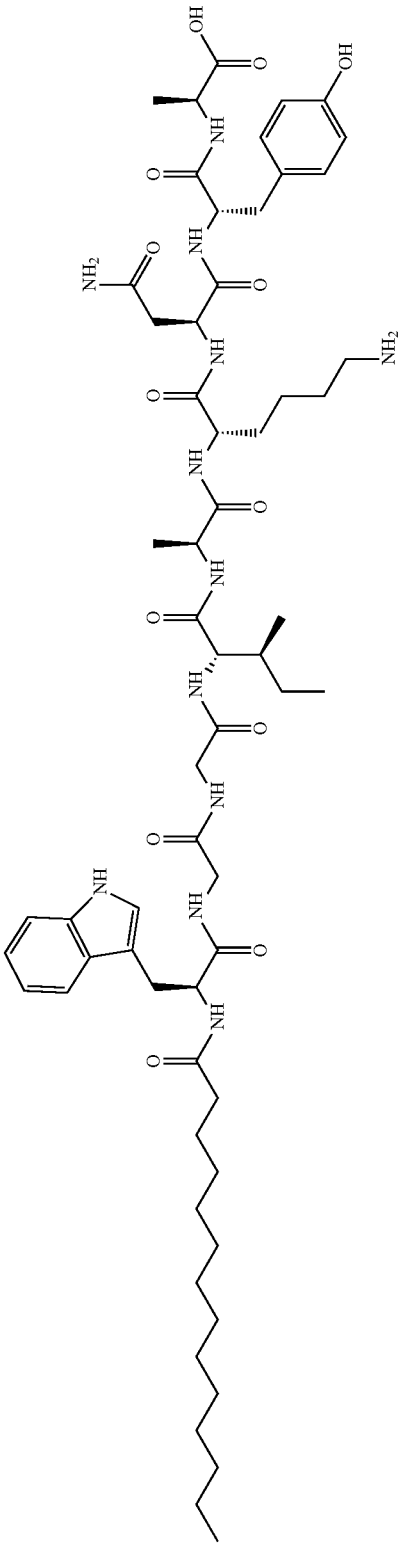
AW9-Ma-K5A (K54)

-continued
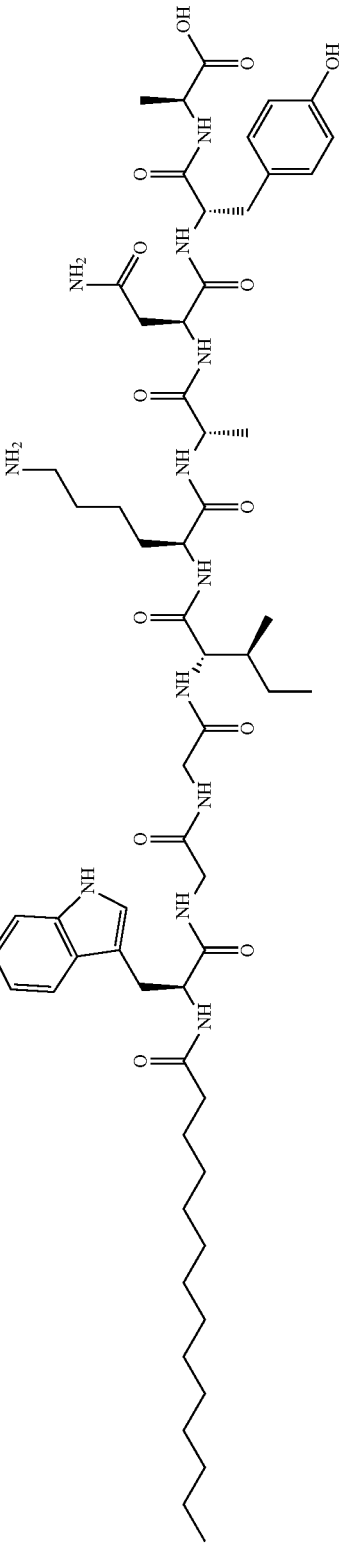
AW9-Ma-K6A (K6A)
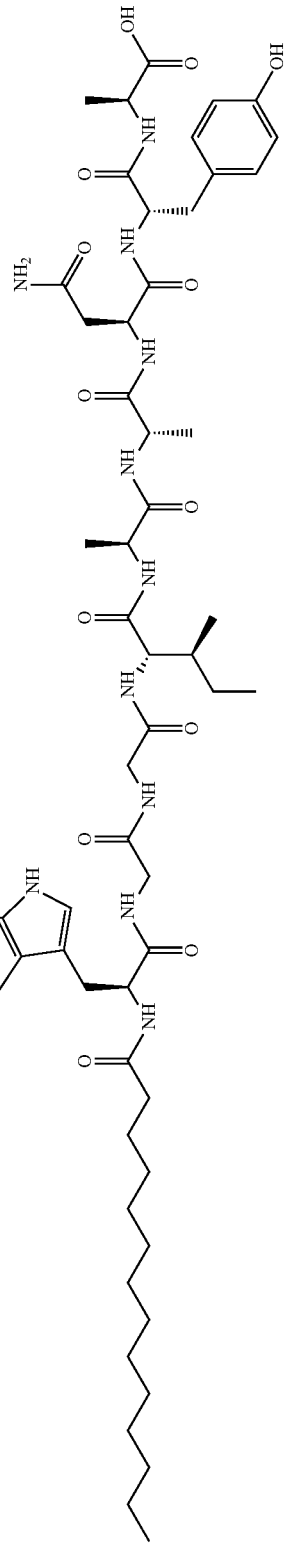
AW9-Ma-K5A;K6A (K5A;K6A)

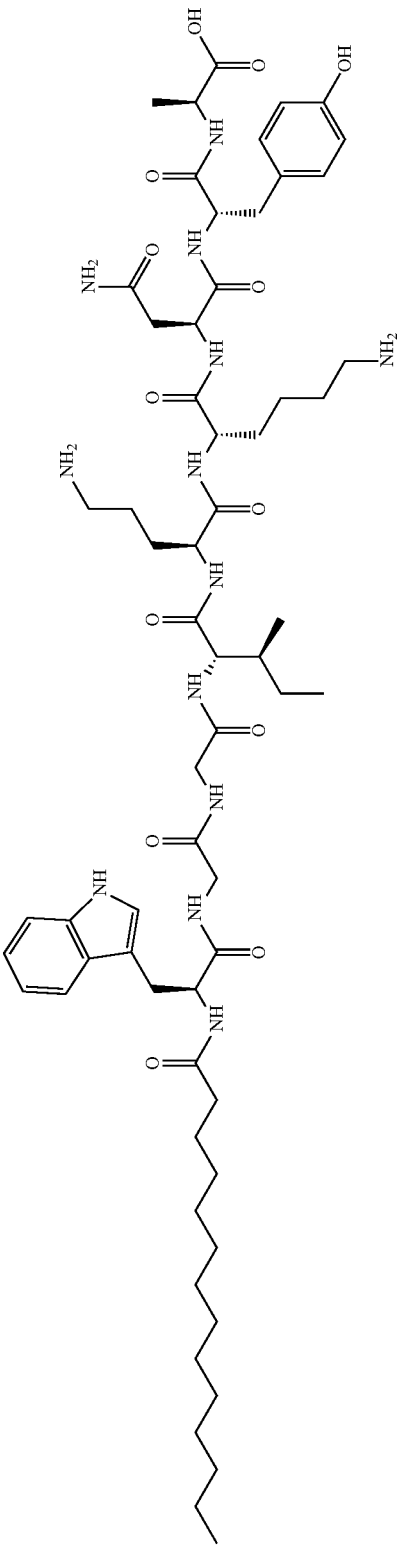
AW9-Ma-K5O (K5O)
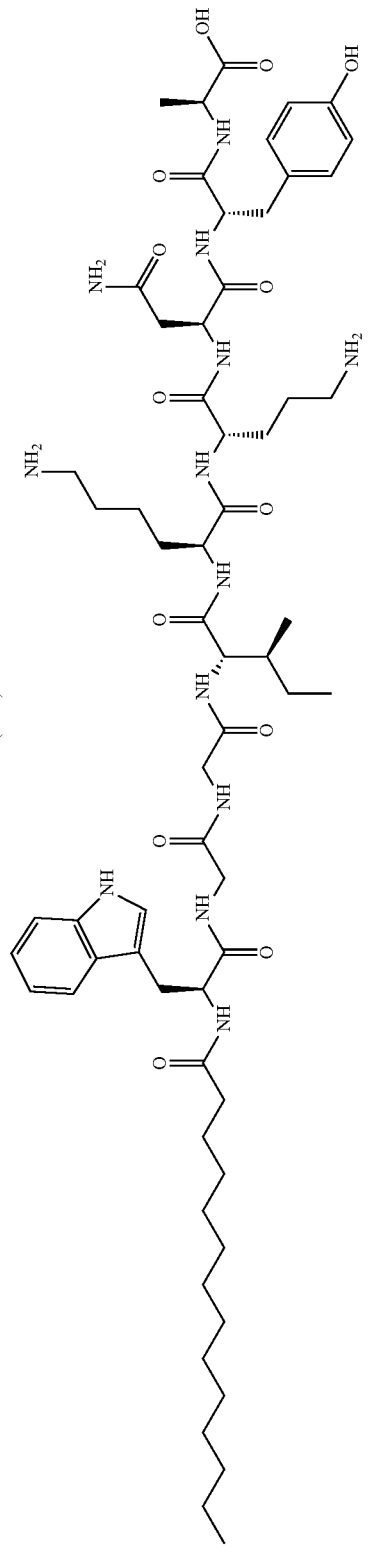
AW9-Ma-K6O (K6O)

-continued
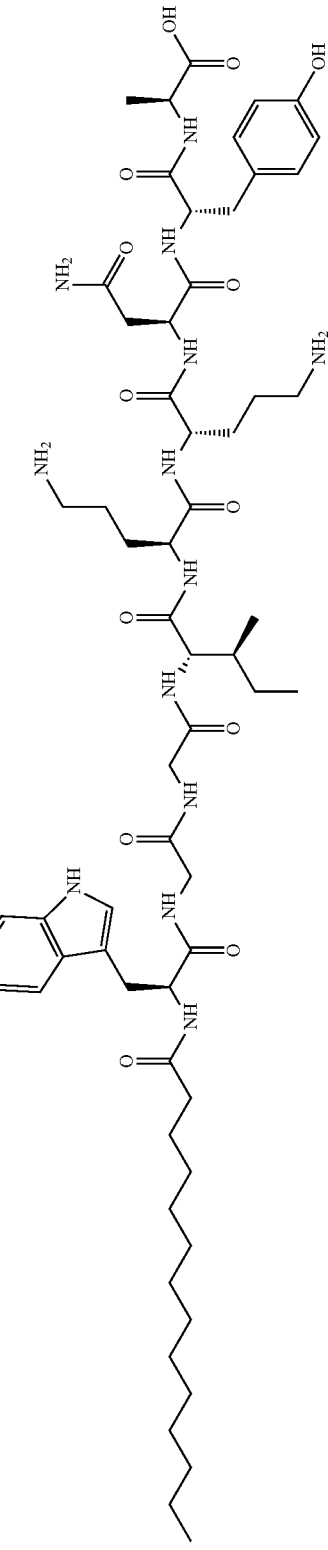
AW9-Ma-K5O;K6O (K5O;K6O)
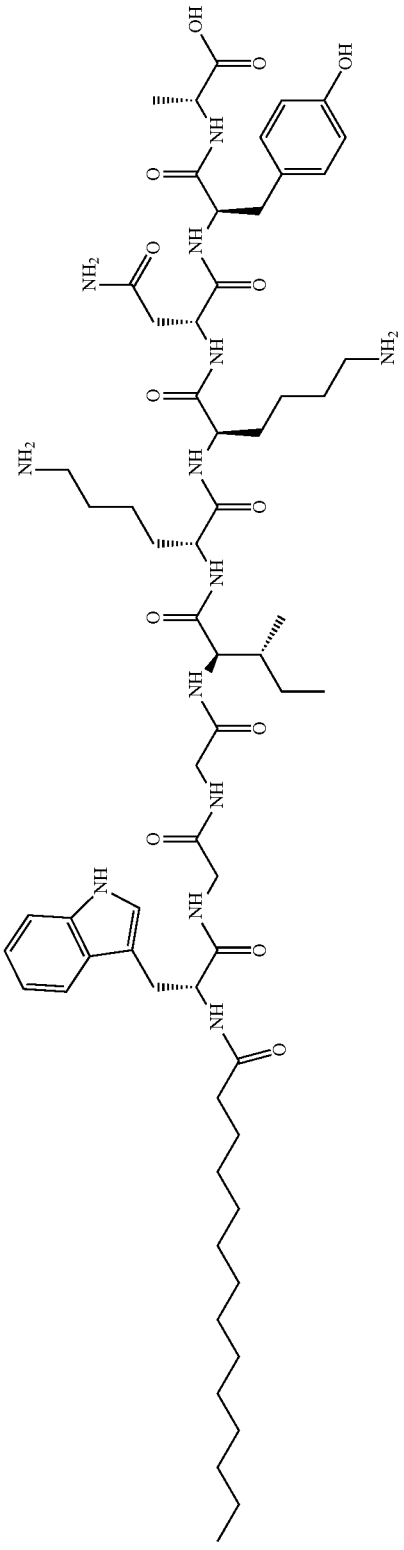
AW9-Ma-D

-continued
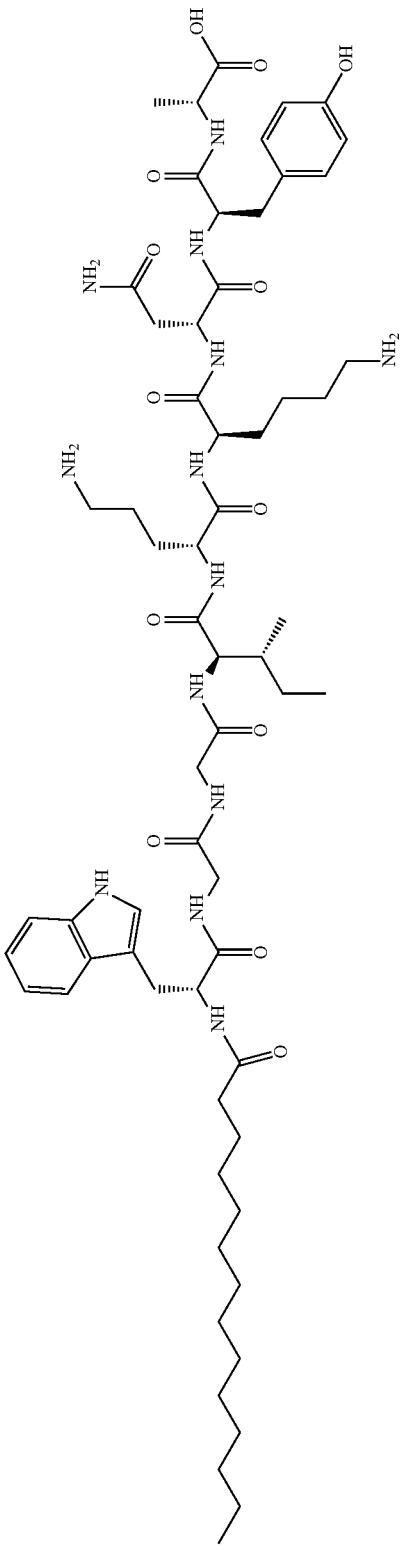
AW9-Mα-K5O-D (K5O-D)
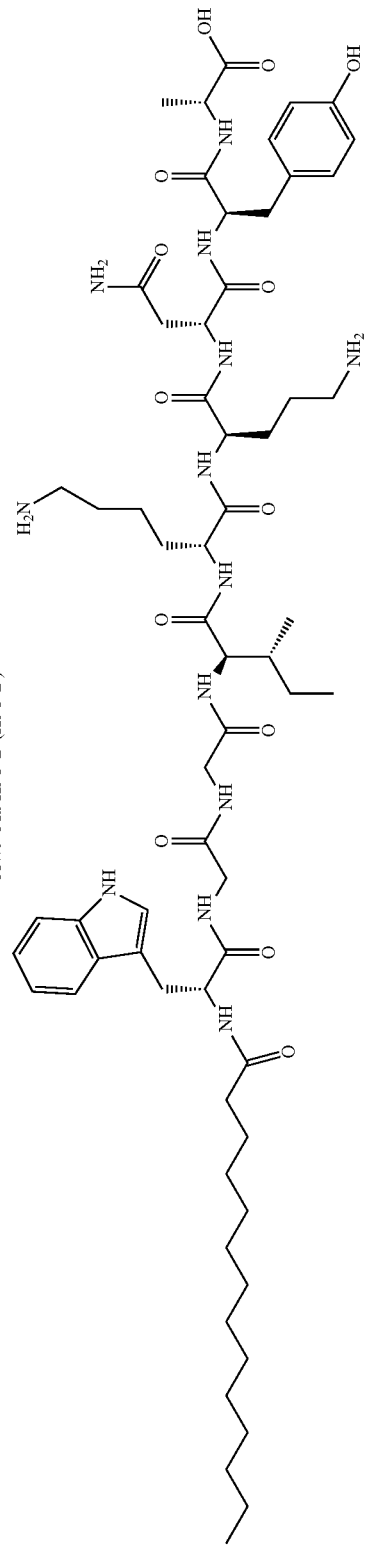
AW9-Mα-K6O-D (K6O-D)

-continued
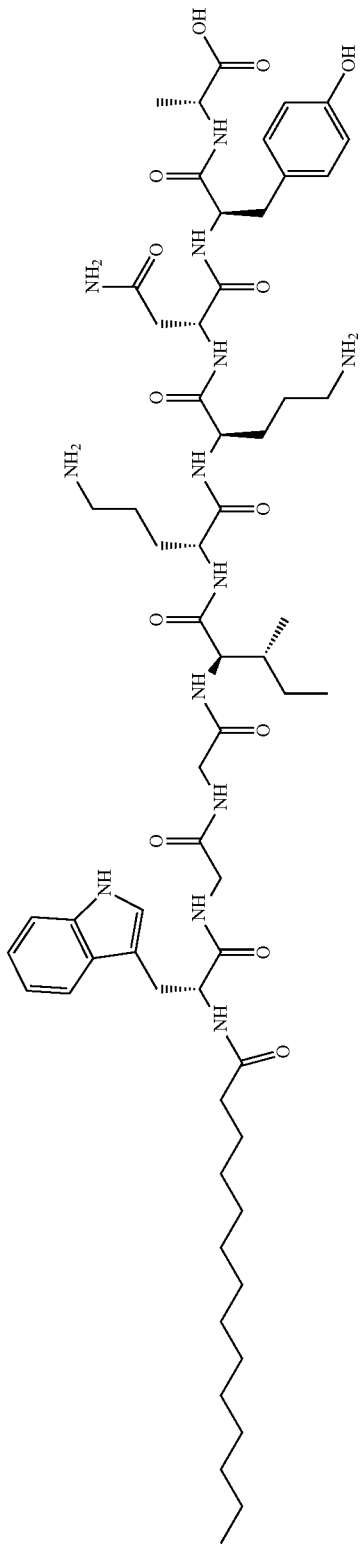
AW9-Ma-K5O;K6O-D (K5O;K6O-D)
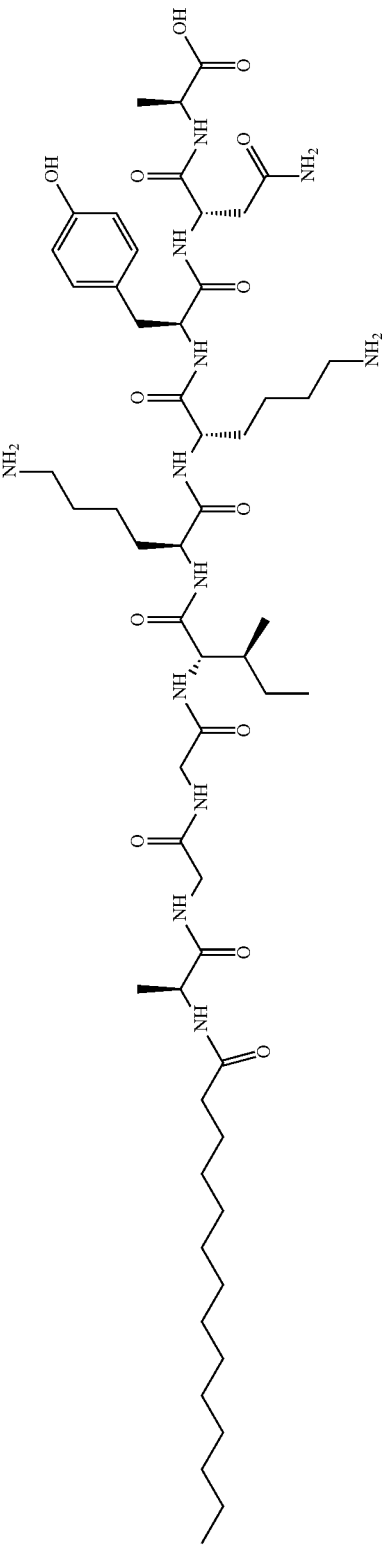
AW9-A1

-continued
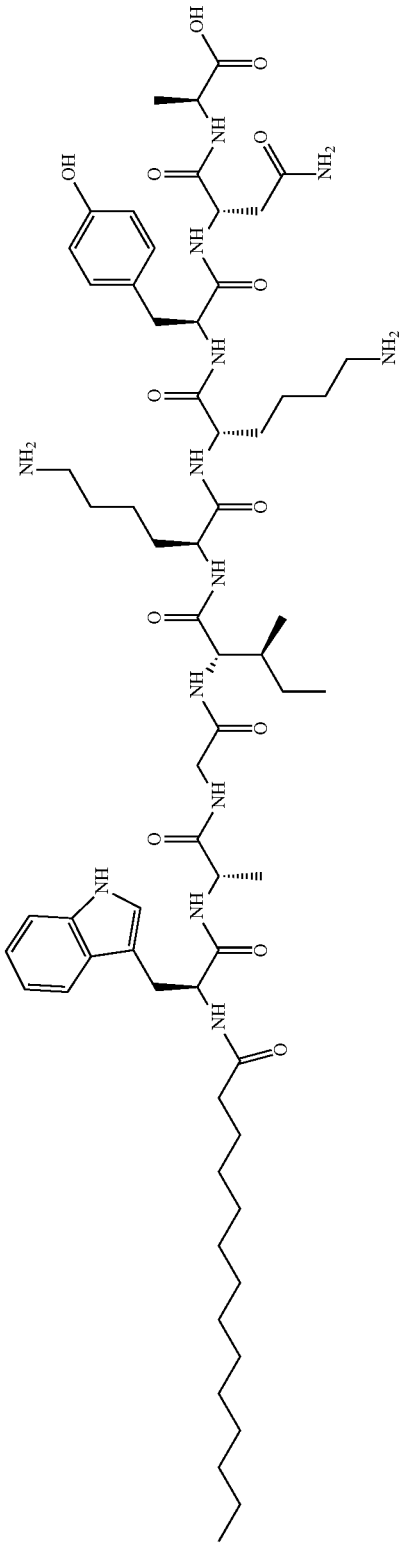
AW9-Ma-A2
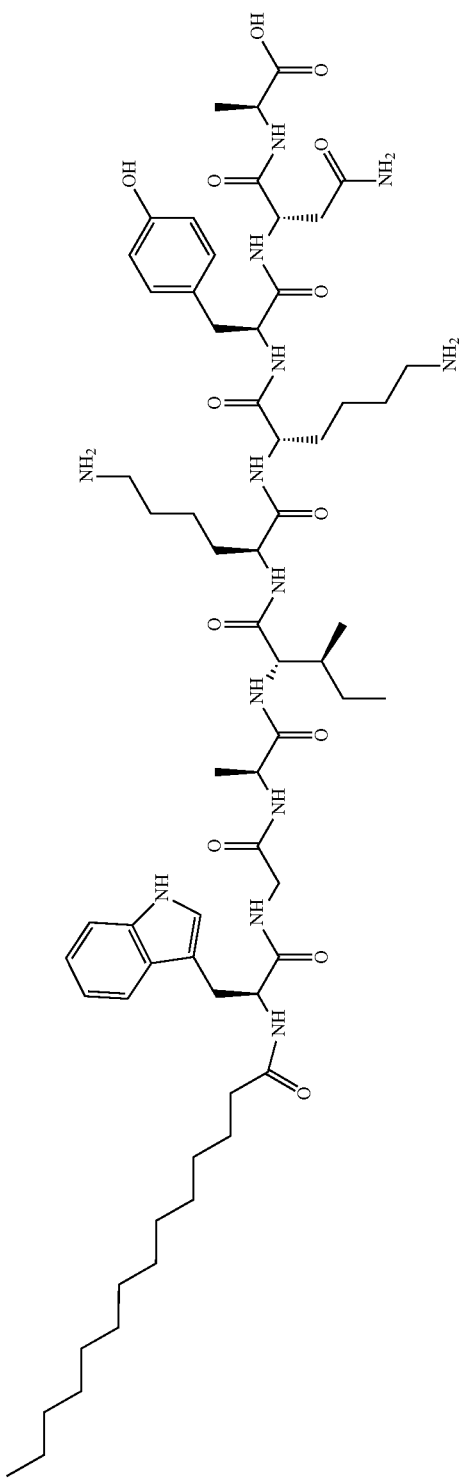
AW9-Ma-A3

-continued
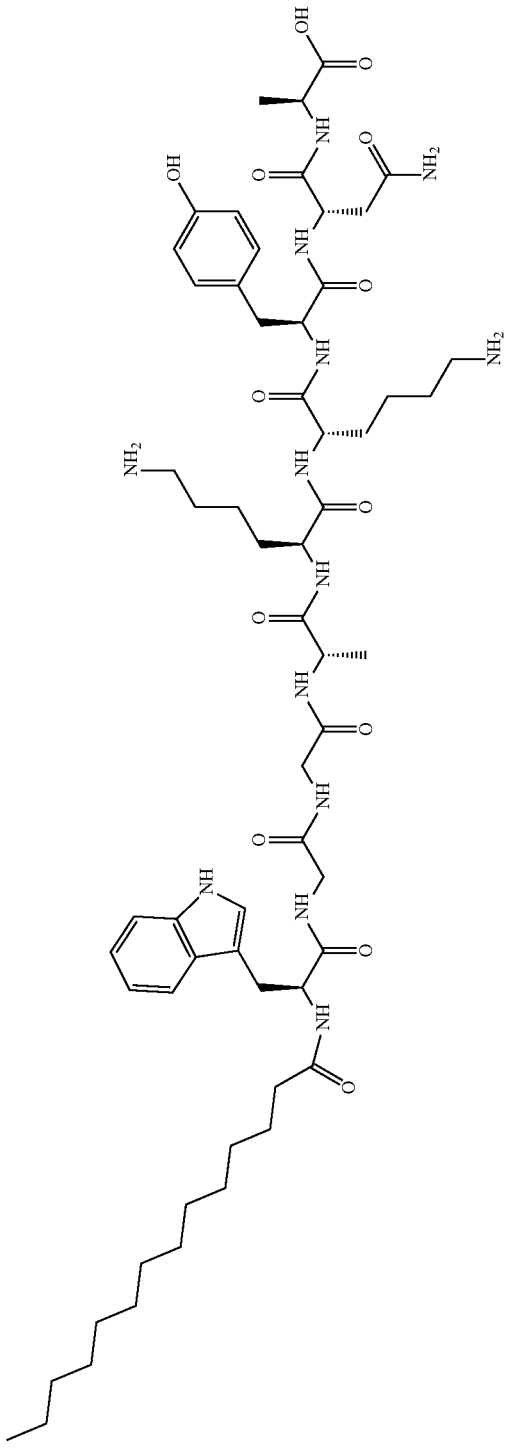
AW9-Ma-A4
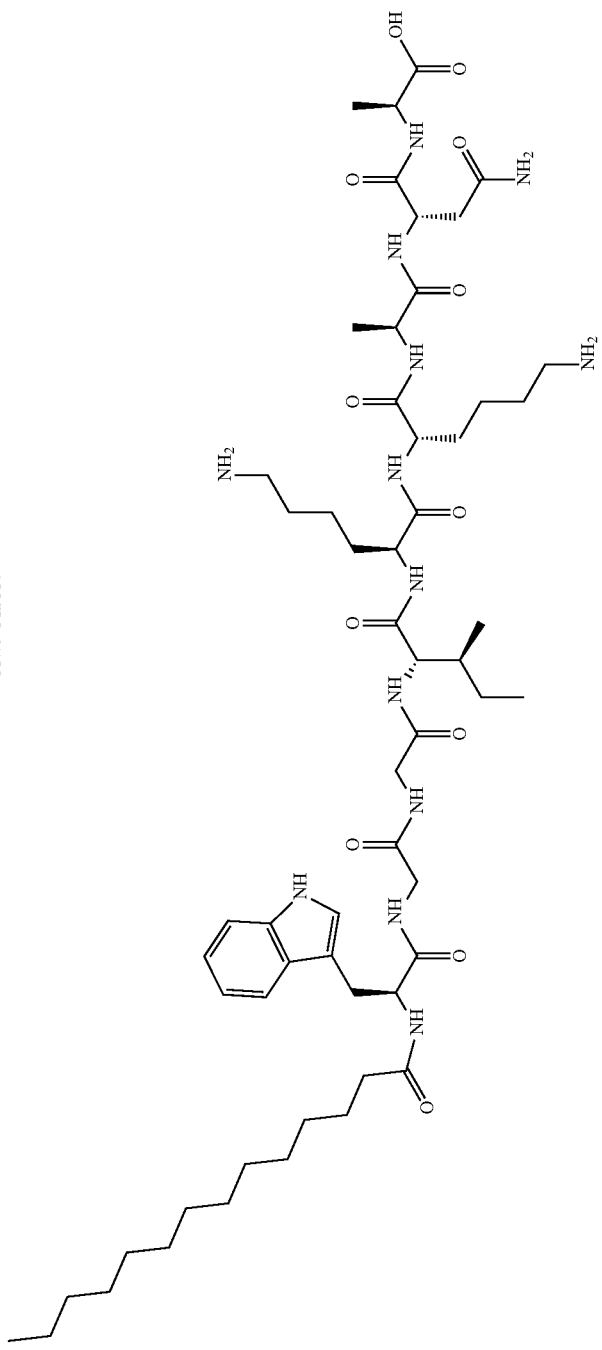
AW9-Ma-A7

-continued
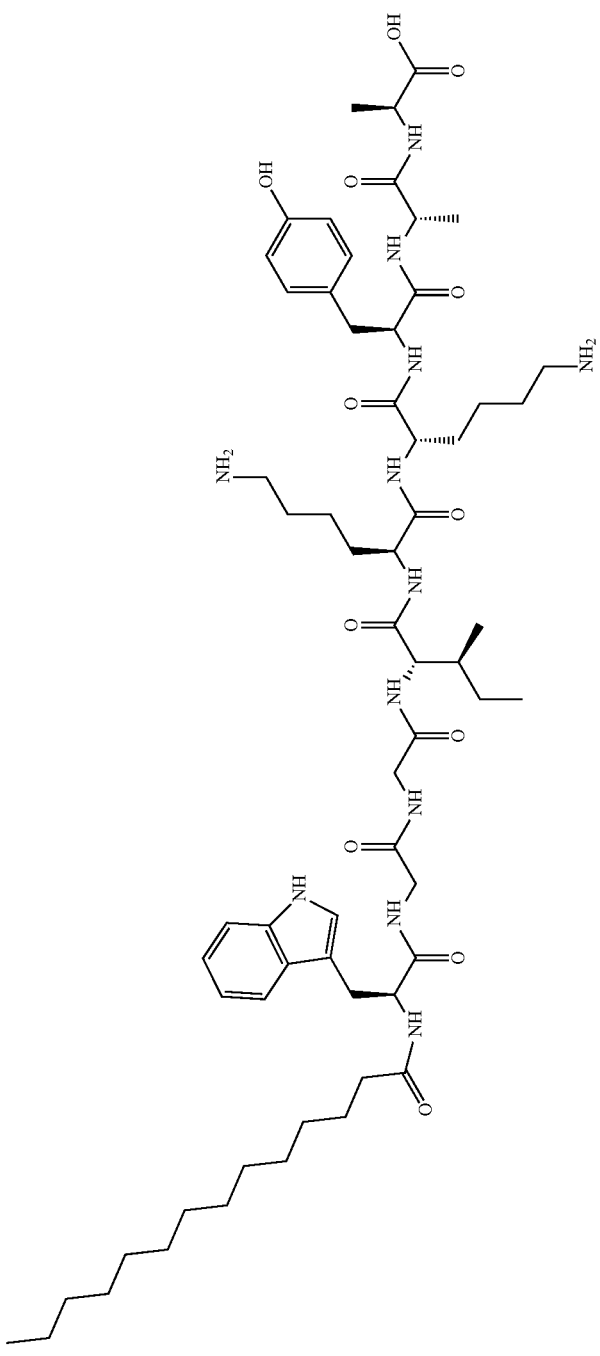
AW9-Ma-A8
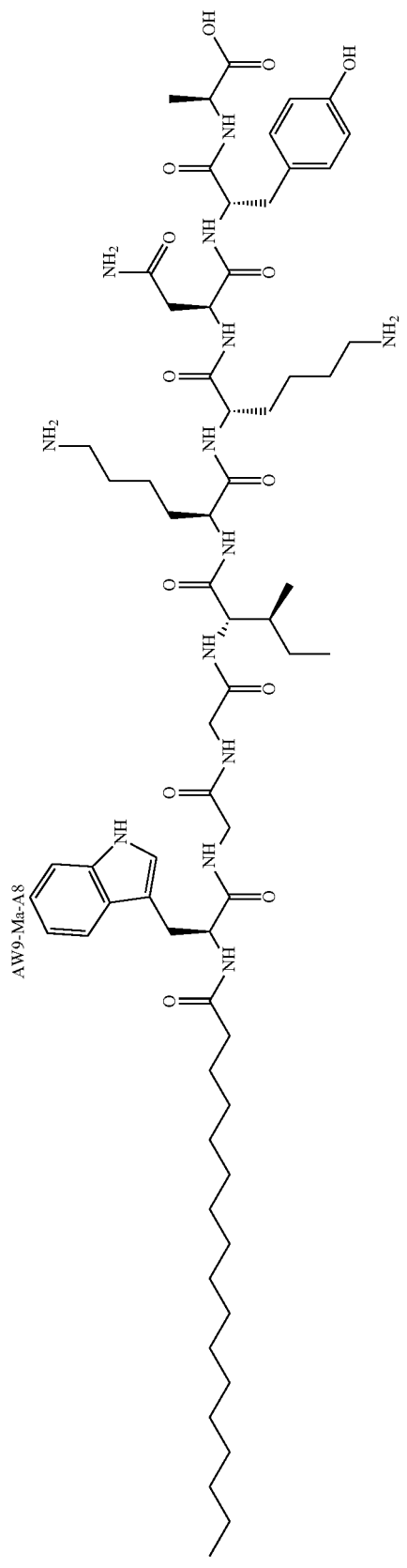
AW9-Pa

-continued
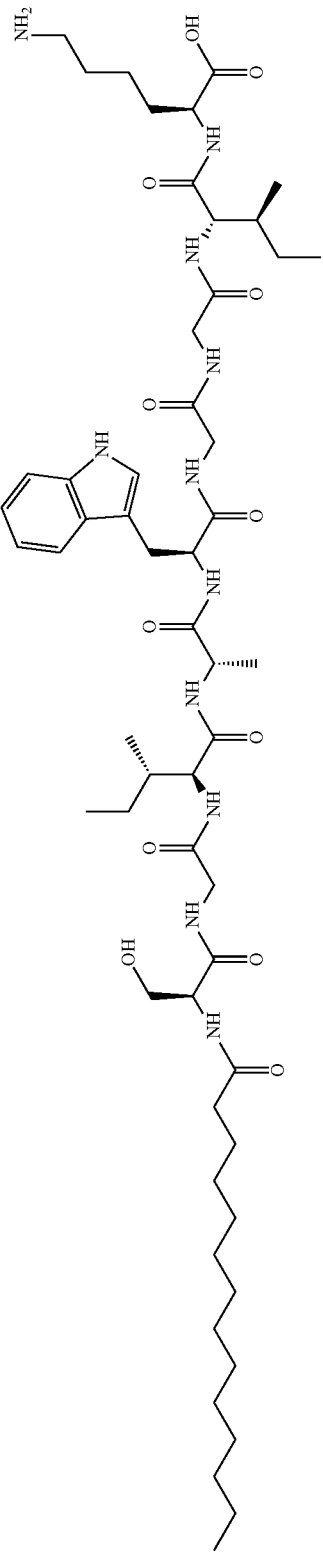
KS9-Ma
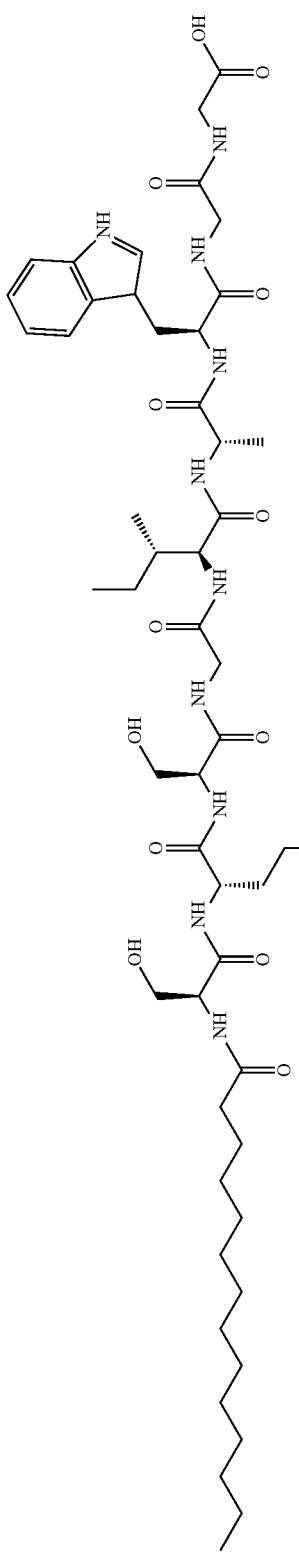
GS9-Ma

-continued
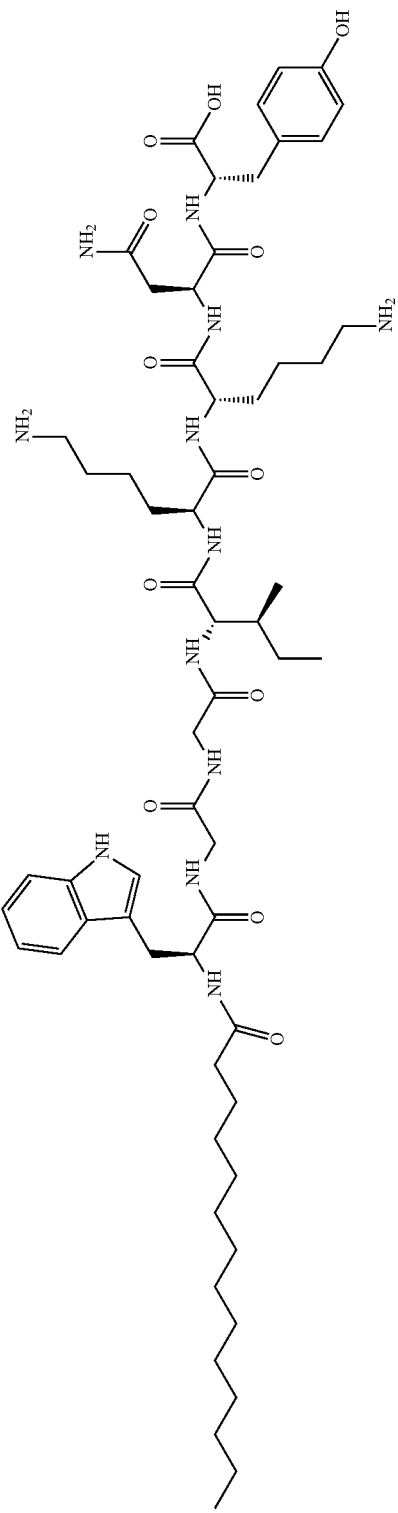
YW8-Ma
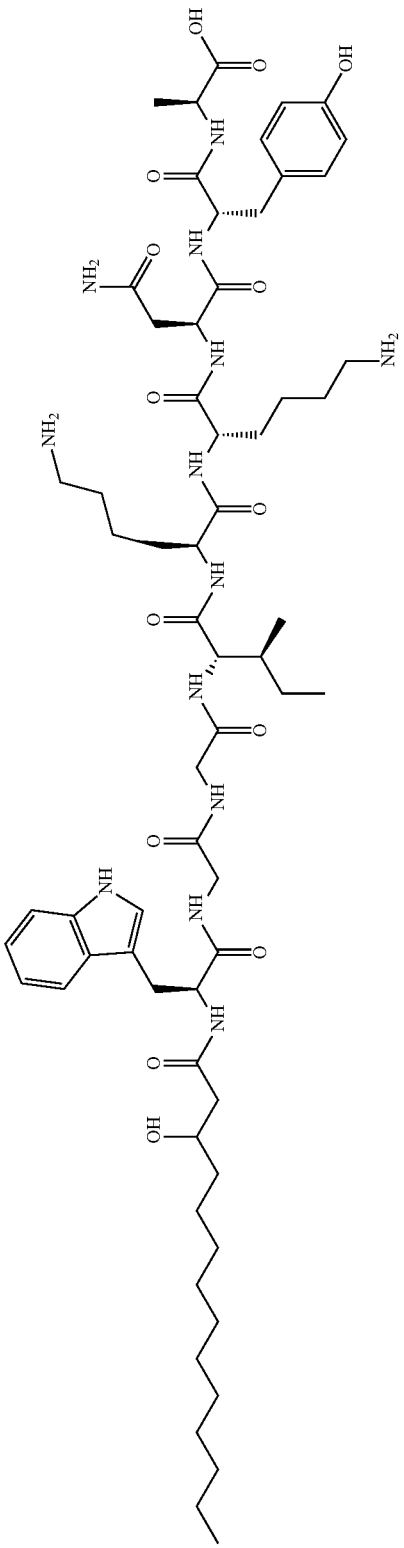
AW9-βHMa

-continued
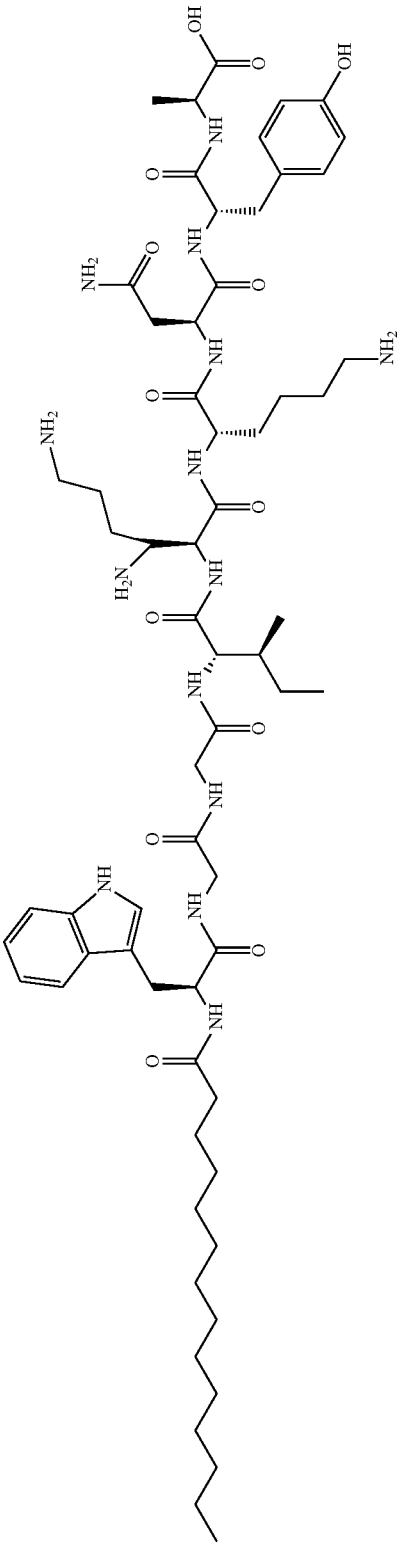
AW9-K5Dab
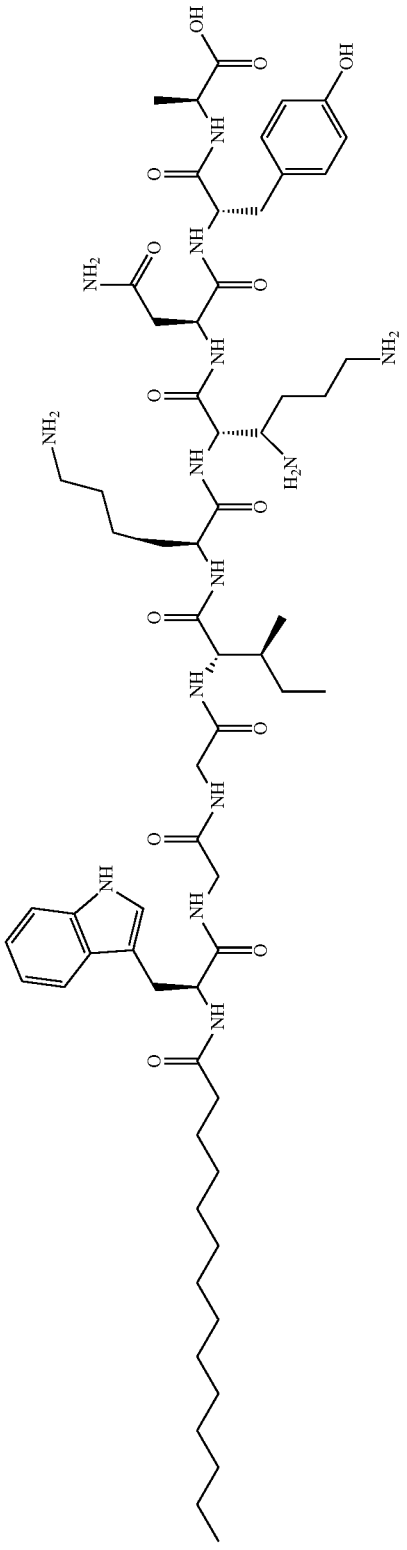
AW9-K6Dab

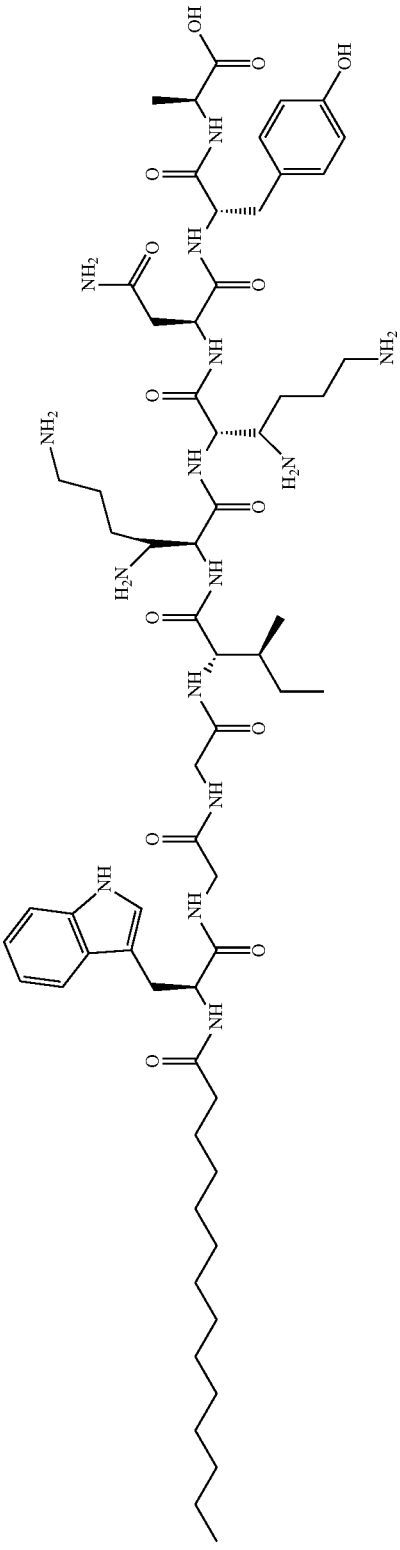
AW9-KKDabDab
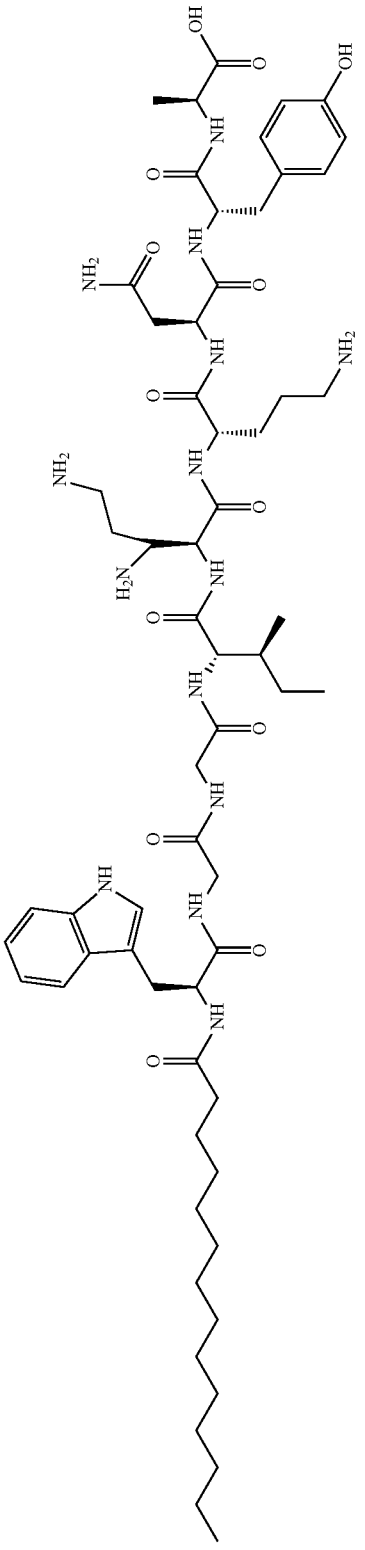
AW9-K5Dap

-continued
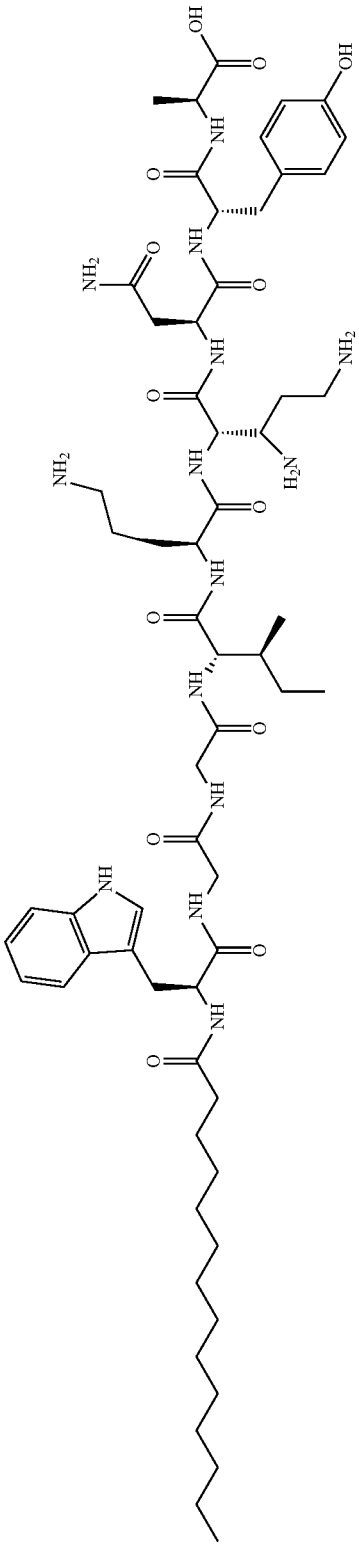
AW9-K6Dap
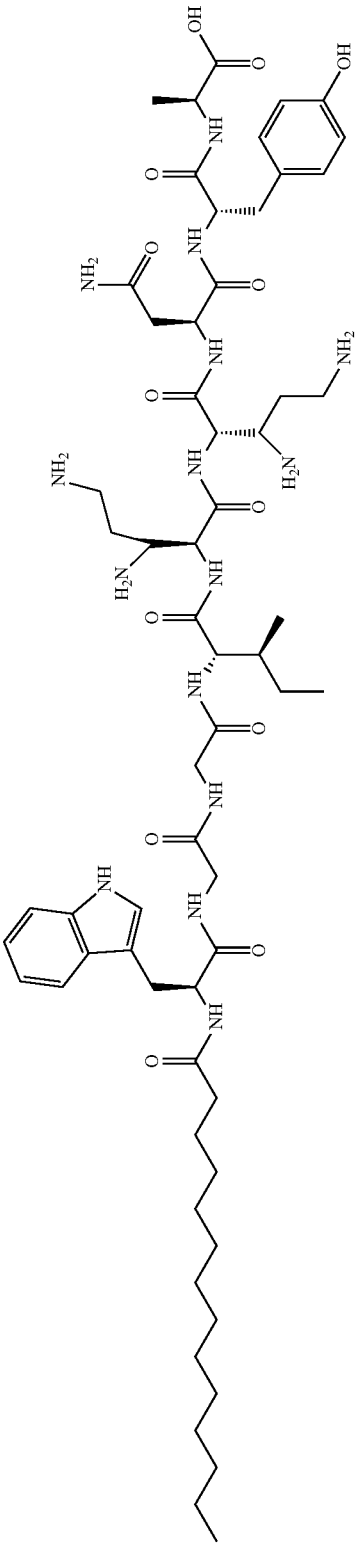
AW9-KKDapDap

Experimental Materials and Methods

Materials

Piperidine and acetic anhydride were supplied by Alfa Aesar (Haverhill, MA). Caspofungin was supplied by AM Beed (Arlington Heights, IL). Sodium hydroxide was supplied by Avantor (Philipsburg, NJ). Yeast peptone dextrose media was supplied by Beckton Dickinson (Franklin Lakes, NJ). Formic acid and Sabouraud dextrose agar were supplied by Merck (Kenilworth NJ). Wang resin and fluorenylmethoxycarbonly (Fmoc) protected amino acids were supplied by Novabiochem (Burlington, MA). O-(1H-6-Chlorobenzotriazole-1-yl)-1,1,3,3-tetramethyluronium hexafluorophosphate (HCTU) was supplied by Peptides International (Louisville, KY).

Biorad Assay Reagents were supplied by Bio-Rad (Richmond, CA). Sulfuric Acid was supplied by Pharmco (Brookfield CT). Alexafluor350 and Alexafluor350-labeled Annexin V were supplied by Thermo Fisher Scientific (Waltham, MA). Dimethyl formaldehyde (DMF), Dimethyl sulfoxide (DMSO) and Acetonitrile (ACN) were supplied by VWR (Radnor, PA). Human red blood cells (RBCs) were supplied by Interstate Blood Bank (Philadelphia, PA). All other materials and reagents were supplied by Sigma Aldrich (St. Louis, MO).

Western Blot Analyses

Total proteins from animal tissues (Bone Marrow, Heart and Lung), *Cryptococcus neoformans* cells (wild type strain H99,fbp1Δ mutant strain and cdc50Δ mutant strain), and mouse macrophage cell line J774 were extracted. Protein extraction was performed as previously described. Animal tissue cells, yeast cells and macrophage cells were rapidly frozen in a dry ice/ethanol bath, resuspended in lysis buffer (50 mM Tris-HCl [pH 7.5], 1% (w/v) sodium deoxycholate, 5 mM sodium pyrophosphate, 10 nM sodium orthovanadate, 50 mM NaF, 0.1% (w/v) SDS, and 1% (v/v) Triton X-100) containing a cocktail of protease inhibitors (0.5 mM phenylmethylsulfonyl fluoride, 1 μg of pepstatin $ml^{-1}$, 1 mM benzamidine, and 0.001% aprotinin) with 1-1.2 g of acid-washed glass beads and disrupted using a FastPrep instrument (FastPrep-24 5G, MP Biomedicals, CA).

Protein concentrations were determined by Bio-Rad Protein Assay reagent. Proteins were loaded into a 10% Trisglycine gel, and separated proteins were further transferred to Immuno-blot PVDF membrane (Bio-Rad) and incubated overnight at 4° C. with a primary rabbit Cdc50 specific antibody (GenScript, Piscataway, NJ) and with a secondary anti-rabbit IgG horseradish peroxidase-conjugated antibody. The blot was developed using the ECL Western Blotting Detection System (Amersham Bioscience, Piscataway, NJ). Subsequently, the blot was stripped and further used for detection of Actin, with a mouse beta-actin monoclonal antibody (GenScript) as a loading control.

Peptide Synthesis

Microwave assisted (CEM Discover), solid phase peptide synthesis (SPPS) was used to synthesize the peptides. Each peptide was made using standard FMOC, tBu protection scheme at 0.05 to 0.1 mmol scale. The first amino acid coupling was repeated 4 times to ensure quantitative labeling to wang resin 100-200 mesh before proceeding to the first deprotection. All other amino acids were coupled once. For the first two groups of peptides, coupling ingredient molar ratios were 5:5:10:1, amino acids:HCTU:DIEA:peptide.

Excess 20% piperidine in DMF was used as the deprotection solution. Subsequent peptides were synthesized with molar ratios of 3:3:6:1 respectively. Fatty acid tails (FATs) were conjugated to the N terminus of the peptide using their respective anhydrides C2-C14, and DIEA, 1:1:1, FAT:DIEA:peptide. Palmitic C16 FAT was coupled using palmitic acid, HCTU, and DIEA, 1:1:3:1, FAT:HCTU:DIEA:Peptide. All fatty acid tails were double coupled to ensure maximum labeling. Peptides were cleaved in 6 mL tubes for 1 hour using 95%:2.5%:2.5% trifluoroacetic acid (TFA):Triethylsilane (TES):$H_2O$ (v:v:v).

Resulting solution was collected quantitatively in a 50 mL falcon tube. A steady stream of $N_2$ gas was used to evaporate the liquid. The remaining plug of material was diluted to 25 mL in 10% acetic acid in water. The sample was vortexed and sonicated for 30 minutes before freezing in the −80° C. freezer overnight. The frozen peptide solutions were lyophilized and stored for further purification.

Purification and Liquid Chromatography

A Varian Prep Star chromatographic system (Palo Alto, CA), was used to purify the peptides. Samples were diluted to 15 mL in 30% acetonitrile in water with 0.1% Formic acid (FA) buffer. The mixture was vortexed and heated with a heat gun until sample was mostly dissolved. The mixture was clarified by filtering through 0.45 μm filter tip. Clarified filtrate (5-8 mL) was loaded into a 10 mL injection loop. Preparatory column used was Phenomenex, Luna 10 C18(2), 250 λ21.20 mm, 10μ. A 5 mL per minute flow rate was used for a gradient of 5-95% ACN. The 220 nm and 280 nm channels were used to detect the sample via dual channel detector. Fractions were collected in 50 mL falcon tubes and were switched by hand. Fractions were selected, combined, and worked up based on the mass spectra and analytical HPLC traces. Combined volumes were reduced to 20-30 mL on a roto-evaporator and acidified to 10% acetic acid V/V. Solutions were vortexed and sonicated for 10 minutes before freezing overnight in the −80° C. freezer. Subsequent solids were lyophilized to dry powder and characterized. Results are provided as shown and labeled S4.

Analytical HPLC was performed using a Shimadzu Nexera-i LC-2040C 3D plus device. The column used was a Waters XBridge Shield RP 18, 3.5μ, 3.0×150 mm. Peptides were prepared at 1 mg/mL in 40% ACN with 0.1% FA and filtered through 0.22 μm filter. Experiments were performed with a flow rate of 1 mL/min. A mobile phase gradient of 5-95% ACN ($H_2O$ with 0.1% FA and ACN with 0.1% FA. Data was recorded using a PDA spectrometer with a spectral window of 200-456 nm, a resolution of 256, and a frequency of 30 Hz.

Mass Characterization

Peptide masses were verified using several different methods. Peptides were characterized using an ESI-MSD single quad device, HP Series 1100 (Palo Alto, CA). This was done using 10 μL direct injections with a flow rate of 0.5 mL/min. In these experiments, the mobile phase was 90% MeOH in water with 0.1% FA. Peptides were prepared at 1 mg/mL in 40% ACN with 0.1% FA and filtered through 0.22 μm filter. Some peptides were further analysed using a triple quad device, Perkin Elmer QSight 225MD (Waltham, MA). Clarified filtrate from single quad sample prep was diluted by a factor of 1000 in ACN with 0.1% FA to 1 μg/mL for direct infusion at 30 μL/min. Further analysis by MALDI-TOF was provided by the Mass Spectroscopy Lab (University of Illinois, Urbana, IL). Results Table is provided in S5.

Cryptococcal Minimum Inhibition Concentration (MIC) Assay

The assays followed standard CLSI protocol for broth microdilution assays using yeasts.(32) Microbes were passaged in YPD media at 37° C. with mixing for 2 days before harvesting with an inoculation loop to prepare monocultures on Sabouraud Dextrose Agar (SDA) plates. Monocultures on SDA plates were incubated for 2 days at 37° C. before harvesting cells for microdilution assays. RPMI media (100 µL) was charged to each of the 96 wells in a 96 well plate, with an additional 100 µL in the first column. Peptide-DMSO solution (4 µL) at 12.8 mg/mL was charged to each of the wells in the first column. The 100 µL was serially diluted by a factor of 2 from the first column to the 11th column. Microbe inoculant was then prepared. An inoculation loop was used to transfer 1-3 colonies of cells to 1 mL phosphate buffer solution (PBS). The PBS and microbe solution was made uniform by vortex mixing. Cell concentration was computed by comparing the absorbance at 530 nm to 1× McFarland standard solution and multiplying the resulting ratio by $10^7$ cell/mL conversion factor. Plate inoculant was prepared by diluting the PBS microbe solution to 5000 cell/mL, in RPMI media. A 100 µL aliquot of cells was transferred to each of the wells on the plate other than column 11 for the no growth control. The operating volume was 200 µL, with 500 CFU per well for a final concentration of $2.5*10^3$ cells/mL. Inoculated plates were incubated for 48 hours at 37° C. and read at 24 and 48 hours.

Checkerboard Assay

Microbes were prepared in the same manner as the MIC assay. The first set of drug dilutions were prepared in a similar manner as the MIC assay except for 4 µL peptide-DMSO stock solution was charged to the wells instead of 2 µL and drugs were serially diluted to column 8 instead of 11. 100 µL of RPMI media was added to the first 8 wells in the first row. A 2 µL aliquot of Peptide-DMSO stock solution at 12.8 mg/mL was added to each of the 8 wells in the first row. The 100 µL of media with drug was serially diluted from the first row to the final row. Columns 9 and 10 were used as MIC control wells for the two drugs. Column 11 was the no growth control, and 12 was the no drug control. The plate was inoculated with microbes in the same manner as the MIC assay. Again, 200 uL was the operating volume, 500 CFU per well, $2.5*10^3$ cell/mL. Plates were incubated for 48 hours at 37° C. and read thereafter. The Fractional Inhibitory Concentration Index were calculated as follows:

$$\text{FIC Index} = \frac{FIC_A}{MIC_A} + \frac{FIC_B}{MIC_B} \quad \text{Equation 1}$$

Where the $MIC_A$ and $MIC_B$ are the MIC values of drugs A and B alone and $FIC_A$ and $FIC_B$ are the Fractional Inhibitory concentrations of drugs A and B in the presence of each other, respectively.

Hemolysis Assay

Hemolysis assays were preformed using human red blood cells (RBCs), which were provided by Interstate Blood Bank (Philadelphia, PA) and stored immediately at 4° C. upon arrival. A description of the method development for this assay is further provided in Supporting Information. Free heme was extracted from stored RBCs washing in PBS with gentle centrifugation at 1000 RPM for 5 minutes. Washed cells resuspended to 4 mL in PBS and counted using a hemocytometer. Hemolysis assay plates were prepared by charging 50 µL PBS to each well of an 8×8 grid on the 96 well plate, and an additional 50 µL aliquot PBS to the first 8 wells in row A. A 2 µL aliquot of peptide-DMSO stock solution at 12.8 mg/mL was transferred to 4 of the wells in row A. A second peptide-DMSO stock solution was transferred in the remaining 4 wells in row A. A 50 µL aliquot of solution was then serially diluted by a factor of 2 down the plate from row A to row H. A 50 µL aliquot of PBS was charged to 8 additional wells on the plate to account for the positive and negative controls. Red blood cells were adjusted to $5*10^8$ cells/mL and 50 uL was added to each of the wells. Operating conditions were 100 µL and $2.5*10^8$ cell/mL. The positive control used as 2 µL of 1% Triton X-100. The plate was incubated at 37° C. for 1 hour. The resulting plate was spun down at 1000 RPM for 5 minutes. 20 µL supernatant was transferred to 80 µL PBS in a fresh 96 well plate for analysis (operating volume 100 µL.) A Spectra Max 340 plate reader (Molecular Devices, Sunnyvale, CA) was used to measure the absorbance of the analysis plate at 410 nm. The scans were run in triplicate. Averages and standard deviations between scans and replicates were computed. The negative control was subtracted from all the data points. The resulting corrected data was normalized by the corrected positive control.

AF350-Annexin V Flow Cytometry Assay

Stock microbes were defrosted from the −80° C. freezer and were passed twice for 48 hours each in YPD media. The YPD media was removed by spinning down and the supernatant was decanted. Pelletized cells were resuspended in 1 mL PBS media and washed for 5 minutes with incubation at 25° C. and 250 RPM. Washed cells were spun down again and suspended in 1 mL of PBS solution. cells were diluted 20-fold into 1 mL fungal working solution in an eppendorf. Cell concentration was quantified via comparison to 1× McFarlain's standard on a plate reader using the absorbance value at 530 nm. An aliquot of $1*10^6$ cells in 100 µL was created ($1*10^7$ cell/mL). A 100 µL aliquot of peptide working solution at 0.256 mg/mL was added to the cell suspension for final operating parameters of 200 µL, 0.128 mg/mL peptide, and $5*10^6$ cell/mL. The cells were incubated for 20 minutes at 25° C. and 250 RPM. Baseline and experimental samples were prepared in triplicate. Cells were stained using an operating concentration of 0.001 mg/mL Propidium Iodine (PI) and a 40-fold dilution of AlexaFluor 350 labelled annexin V as per manufactures instructions. After staining the cells, samples were spun down and supernatant decanted. Cells were then fixed in 4% formaldehyde for 5 minutes. Fixed cells were spun down and supernatant decanted and resuspended in 400 µL 1% formaldehyde for flowcytometry. Samples were collected at a slow flow rate on a MACS Quant 10 device (Miltenyi Biotech, Auburn, CA) with 20,000 events collected per injection.

SDS and Plate Spotting Assay

To test cell integrity, C. neoformans strains from 3 ml YPD overnight cultures were washed, resuspended, and serially diluted (1:10) in dH2O and spotted (5 µl) on YPD agar plates or YPD agar plates containing 0.03% SDS and incubated for 2 days at 30° C. and 37° C.

To test the effect of peptide AW9-Ma on cell phenotype. Of each strain, yeast cells were inoculated into liquid YPD with 128 µg/ml or 64 µg/ml peptide and co-incubated for 1 h at 30° C. And then, ten-fold serial dilutions were prepared, and 5 µl of each was spotted on YPD and YPD agar plates containing 0.03% SDS. The results were photographed after a 48 h incubation. Their growth was determined by serial dilutions and the fungal colonies were assessed by CFU numbers.

Example 1—Lipidated Loop Region Peptides Show MIC Toward C. neoformans

Some peptides from Table 1 was examined for the activity against C. neoformans wild type strain H99 in both the presence and the absence of caspofungin. The initial set of peptides (QY15, QY15-Ma, AS15, AS15-Ma) were comprised of the AS15 and QY15 fungal loop region sequences and the lipidated versions of both.

These peptides were termed "Group 1". The nonlipidated peptides from the first group were unable to inhibit the growth of the H99 strain at any concentration up to 128 μg/mL (Table 2). Similarly, the fractional inhibitory concentration (FIC) index for such peptides was 1 or greater, indicating little to no improvement of caspofungin activity or even antagonistic effects.

Visual inspection of the MIC plates suggested that stronger and more confluent growth in the wells dosed with high concentration of un-lipidated AS15 peptide compared to the no drug control. These peptides, contrary to inhibiting the growth of *C. neoformans*, may be involved in growth enhancement as a nutrient supplement.

Unlike the nonlipidated peptides, the lipidated versions showed promising antifungal activity against *C. neoformans*. These peptides exhibited an MIC value of greater than 128 μg/mL, however growth was significantly reduced compared to the no-drug control.

Thus, these peptides may not provide any benefits to growth as observed with the nonlipidated peptides. It was observed an apparent additive effect when combining AS15-Ma and caspofungin in checkerboard assays against H99. In the presence of 0.5 μg/mL AS15-Ma, the MIC of caspofungin was reduced from 16 μg/mL to 8 μg/mL against H99.

An accurate MIC for many of these peptides alone could not be established due to limitations in solubility. For those peptide that did cause the MIC of caspofungin to decrease, an FIC index value was calculated assuming a conservative MIC of 128 μg/mL (see Equation 1).

This suggested that the FIC index for such peptides as 0.504, a value between 0.5-1 and an addative effect. Thus, even a small amount of the myristylated peptide was able to improve the effectiveness of caspofungin against the WT strain.

Similar results were seen with the QY-15-Ma peptide. Unlike QY15-Ma, however, AS15-Ma exhibited an MIC value of 8 μg/mL could be determined against the cdc50Δ mutant strain (Supplemental Material, S1). This suggested that AS15-Ma was the more potent peptide.

Table 2 illustrates the relationship between peptide and FIC Index discussed herein.

TABLE 2

| Peptide and FIC Index For Selected Peptides | |
|---|---|
| Peptide | FIC Index |
| QY15 | >1 |
| QY15-Ma | >1 |
| AS15 | >1 |
| AS15-Ma | 0.504 |

Table 2. FIC index values of caspofungin with original loop peptides against *C. neoformans*. FIC index values are shown. The following are commonly accepted standard interpretations of FIC Index (FICI) values: 2>FIC>1 antagonistic, FICI=1 autonomous, 1>FICI>0.5 additive, FICI≤0.5 drug synergy.

Example 2—Fatty Acid Tail Length is Important for Activity

AS15-Ma was selected for further examination due to the increased activity against cdc50Δ (Supplemental Material). It was sought to determine if the fatty acid tail length was crucial for antifungal activity and drug synergy. Fatty acid tail lengths between acetic (C2) and decanoic (C10) were conjugated to the N-terminus of the AS15 peptide using their respective anhydrides. We also synthesized a palmitic acid version of the AS15 peptide (AS15-Pa).

These peptides comprised a second group (Group 2) of possible antifungals and or caspofungin potentiators. As seen in Table 3, none of the FAT scan peptides with tails smaller than C14 inhibited the growth of *C. neoformans*. The effects were autonomous or mildly antagonistic. The palmitic labelled AS15 showed a similar, additive effect compared to the Group 1 peptide (0.5<FIC Index<1).

These results suggest a minimum fatty acid tail length is required for peptide activity. Additionally, this shows that increased hydrophobicity from the longer tail lengths does not lead to inhibition or complications for delivery through the cell capsule.

TABLE 3

| Peptide and FIC Index For Selected Peptides | |
|---|---|
| Peptide | FIC Index |
| AS15-Pa | 0.504 |
| AS15-Ma | 0.504 |
| AS15-Da | >1 |
| AS15-Ha | >1 |
| AS15-Aa | >1 |

Table 3. FIC index values of caspofungin with peptides of varying fatty acid tail lengths against *C. neoformans*. FIC index values are shown. The following are commonly accepted standard interpretations of FIC Index (FICI) values: 2>FIC>1 antagonistic, FICI=1 autonomous, 1>FICI>0.5 additive, FICI≤0.5 drug synergy.

Example 3—Truncation of the Peptide Region Shows Improved Activity

The initial peptide length of fifteen amino acids was chosen based on previous data using loop-targeting antibodies. It was sought to determine if truncation of the peptides to regions shorter than fifteen amino would alter activity. It was sought to retain the tryptophan W7 due to the fact that it can be utilized in a variety of important bioanalytical and biophysical applications. The present inventors also hypothesized that the important amino acids in AS15 were the lysines: K11 and K12 due to lysine's known importance of charged amino acids for antimicrobials. For these reasons a third group (Group 3) of truncated peptides was synthesized which contained both lysines (AW9), one lysine (KS9), or lacking both lysines (GS9).

It was found that removal of either lysine decreased the activity of the Group 3 peptides and removed their ability to sensitize *C. neoformans* towards caspofungin (Table 4). It was further found that AW9-Ma exhibited improved activity, having a detectable MIC value of 64 μg/mL against *C. neoformans* WT as well as an FIC Index of 0.5. An FIC Index value of ≤0.5 denotes drug synergy. The FIC of caspofungin is 4 μg/mL, which is the value obtained in literature for the MIC of the cdc50Δ against caspofungin. A small amount of group 3 palmitic labelled peptide, 0.5 μg/mL, did improve the effectiveness of caspofungin against the H99, lowering the MIC from 16 to 8 μg/mL. This suggests that the myristic peptide tail is optimal for the activity of the peptides.

TABLE 4

Peptide and FIC Index For Selected Peptides

| Peptide | FIC Index |
|---|---|
| AW9-Ma | 0.5 |
| AW9-Pa | 0.75 |
| KS9-Ma | >1 |
| GS9-Ma | >1 |

Table 4. FIC index values of caspofungin with differentially truncated peptides acid tail lengths against *C. neoformans*. FIC index values are shown. The following are commonly accepted standard interpretations of FIC Index (FICI) values: 2>FIC>1 antagonistic, FICI=1 autonomous, 1>FICI>0.5 additive, FICI≤0.5 drug synergy.

Example 4—Peptides Showed Minimal Hemolytic Activity

Human red blood cells (RBCs) are known to contain a mammalian version of P4-ATPase. These flippases contribute to their membrane integrity. It was therefore aimed to determine if the peptides could contribute to cell death or hemolysis of RBCs in a similar mechanism as compared to *C. neoformans*.

Figure 3:
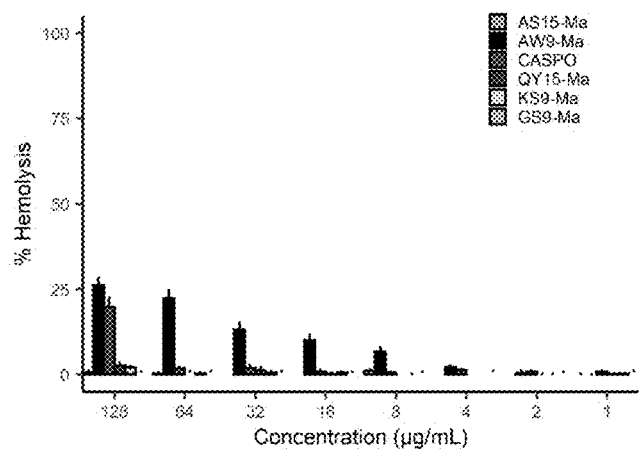

Method development for the hemolysis assay was carried out to ensure the measurements were within the linear response range of the instrument. Different concentrations of RBC's and supernatant transfer volumes were analyzed such as 2*10^8 cell/ml, 4*10^8 cell/ml, 5*10^8 cell/ml, 8*10^8 cell/ml, and 1*10^9 cell. The working number of RBCs used was selected based on the range of cell concentrations seen in patient samples and used in the literature. All peptides showed minimal hemolytic activity, directly proportional to its concentration (FIG. 3).

Of the peptides tested, AW9-Ma did show a concentrate-dependent minimal amount of hemolysis. This would be consistent with interference of the P4-ATPase and possible damage of the RBC membrane. However, at the concentrations needed for synergy, AW9-Ma causes low amounts of hemolysis. Additionally, this amount of RBC hemolysis is lower than what is observed for known cytotoxic antimicrobial peptides.

Figure 4:
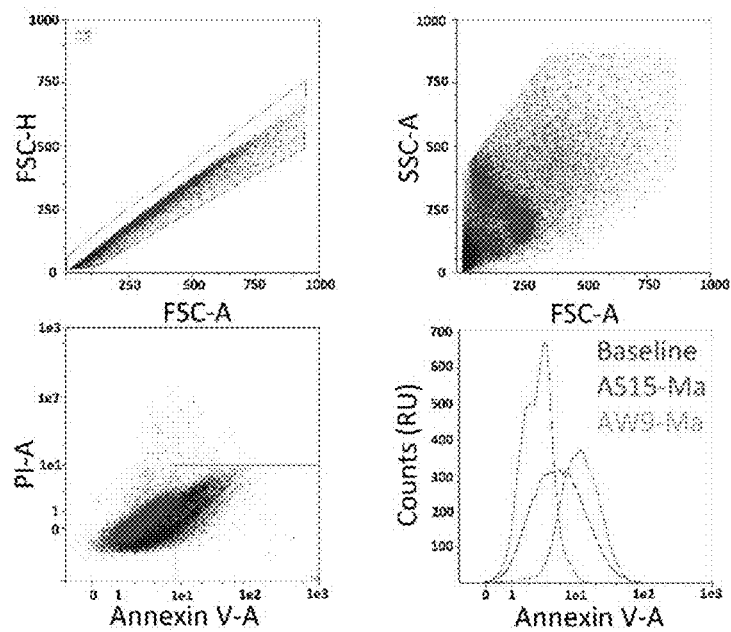

Example 5—Peptide Activity Correlates with Increased Surface Phosphatidylserine It was sought to determine whether the activities of the peptides were related to the lipid-flipping activity of the P4-ATPase. For this reason, flow cytometry experiments were conducted using AW9-Ma or AS15-Ma, propidium iodine, and AlexaFluor 350 labelled annexin V (AF350-annexin V). The intensity of the AF350-annexin V signal corresponds to concentration of PS on the exofacial side of the membrane. The propidium iodine signal corresponds to cell viability. It was found that, compared to a no drug control, there is a significant increase in AF350-annexin V signal, and hence exofacial PS on *C. neoformans* cells caused by the peptides (FIG. 4).

Single cells were first selected and gated based on morphology to ensure homogeneity among the cell population (4A, 4B). Cells with low propidium iodine intensity (PI-A<9 RU) and high AF350-annexin V intensity (Annexin V-A>9 RU) (4C, 4D) were examined. Under these gating parameters there should be, respectively, low non-specific cell death and high exofacial PS. For the control sample, the percentage of cells found within this range was only 0.2±0.1% while for the AS15-Ma treated cells the amount was 12.1±2.0% and AW9-Ma treated cells the amount was 67.6%±2.3%. These values were found to be mutually statistically significantly different with p-values <0.05 in two-sample Student's t-tests. This suggests that, while the peptides were capable of increasing exofacial PS via disruption of P4-ATPase activity, they alone were not permeating the cell membrane. Additionally, increased peptide activity among those peptides tested correlated with increased exofacial PS.

Example 5—Peptide AW9-Ma Co-localizes with a P4-ATPase Apt1 on Cells

Figures 5A, 5B:
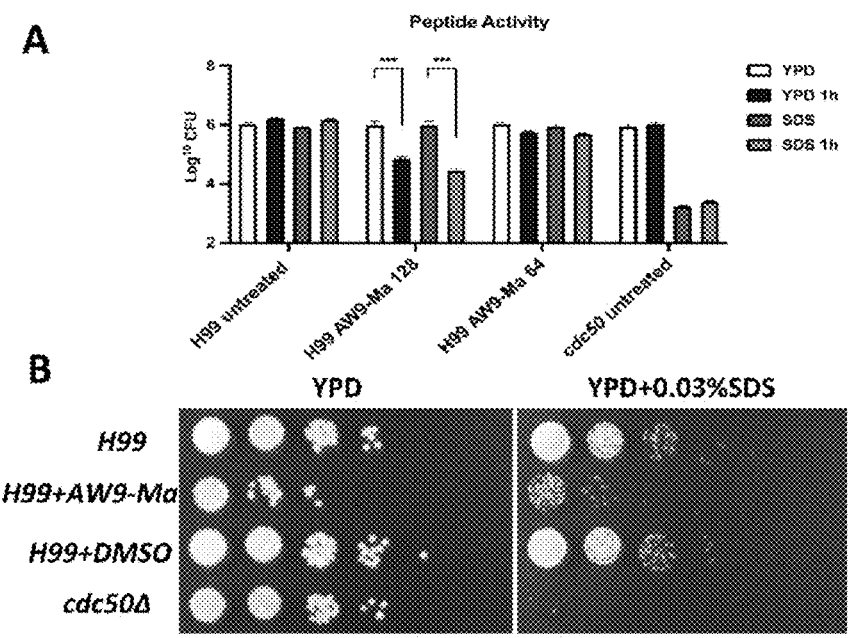

A FITC fluorescently labelled version of the AW9-Ma peptide (FITC-AW9-Ma) was generated to visualize the interaction of the peptides with the cells. This was done to determine whether the peptide was interacting with the surface of the fungi, the location of the P4-ATPase, or some internal portion of the cell. Along the same lines, we also generated a *C. neoformans* strain CUX281 that expresses a mCherry tagged P4-ATPase Apt1 (Apt1:mCherry). Co-localization of the signal would indicate a possible interaction between the peptide and the enzyme. This fungal strain was co-incubated with FITC-AW9-Ma peptide for 10 mins and observed under fluorescent microscope. It was found that the FITC signal was mostly colocalized with the mCherry signal (FIG. 5a-5b). These images show a lack of signal, and hence lack of peptide, in the internal portions of the cells. Rather, peptide accumulated either on the surface or was retained within the cell capsule. This again suggests that the peptides are active on the cell surface rather than an internal target and are not cell penetrating.

Figure 6:
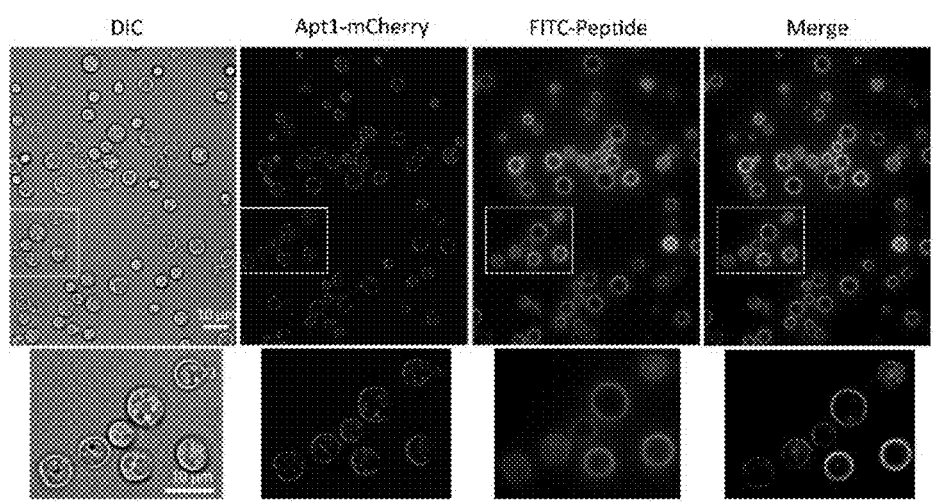

Example 6—Wild-type H99 Treated with Peptides Exhibits cdc50Δ-like SDS Susceptibility Phenotype The *C. neoformans* mutant strain cdc50Δ exhibits increased sensitivity to sodium dodecyl sulphate (SDS) due to a membrane integrity defect. The inventors aimed to determine if this phenotype can be seen in H99 cells treated with the most potent peptide, AW9-Ma, known to the inventors at the time of the experiment. Briefly, cultures of *C. neoformans* were grown in YPD and then spotted on YPD plates containing 0.03% SDS. To test the effect of peptide AW9-Ma on cell phenotype, yeast cells were inoculated into liquid YPD with 128 µg/ml or 64 µg/ml peptide and co-incubated for 1 h at 30° C. Plate spotting assays were performed with the fungi alone (H99, cdc50), with peptide (H99+Aw9-Ma) or with DMSO control (H99+D). Indeed, *C. neoformans* cells pre-treated with AW9-Ma at 128 m/mL for one hour showed a significantly reduced growth in terms of colony forming units on agar medium with 0.03% SDS as compared to untreated or DMSO controls (FIG. 6).

These data indicate that AW9-Ma treatment of *C. neoformans* wild type cells phenocopies the cdc50Δ mutant cells, likely due to its disruption of Cdc50 mediated lipid flippase function.

Figure 7:
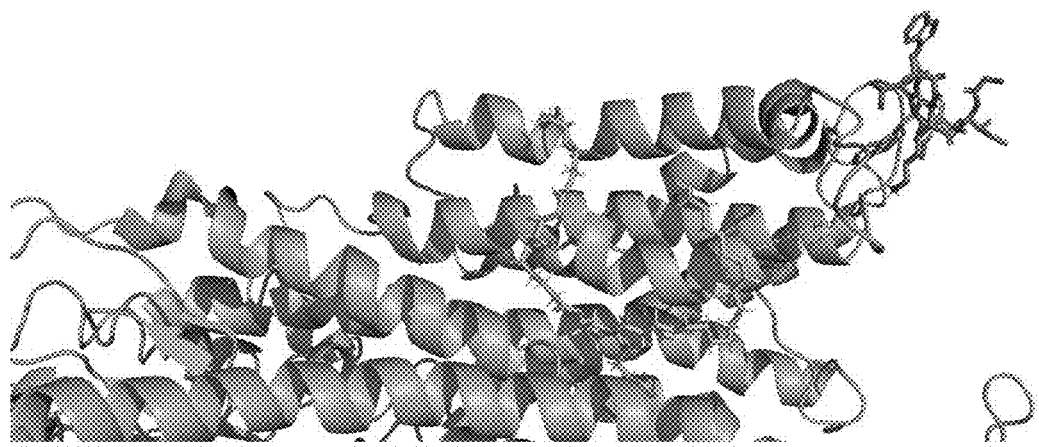

Example 7—Lysine Residues are Involved in Key Interactions in Analogous Flippase-Cdc50 Structures It was sought to examine the interaction of our new lead compound, AW9-Ma with the P4-ATPase. To do so, the homologous structure of an ATPase-PS-Cdc50a complex in several cryo-EM structures were examined. The complementary region in the human P4-ATPase structures was first identified. This was an attempt to find the binding site where the Cdc50a exoplasmic loop interacts with the P4-ATPase. Sequence alignment of the fungal Cdc50 shows that only a portion of the amino acids are conserved between *Homo sapiens* and *C. neoformans*. Nonetheless, this region has several similarities, and can be recognized as related to the source of the original AS15 sequence from *C. neoformans*. The inventors therefore deduce that the interactions of this region of the *H. sapiens* Cdc50a with the *H. sapiens* P4-ATPase are analogous to the interactions of AS15 or AW9 with the *C. neoformans* P4-ATPase. Several existing Cryo-EM derived structures of *Homo sapiens* flippase ATP11C were analysed, which was found in human RBCs as it interacts with Cdc50 to translocate PS molecules. The analogous region for the peptide AW9-Ma is shown in the red box described in FIG. 7.

The structures were screened for any interactions between the protein and the "peptide", the analogous region on Cdc50a which were within 5 Å. Three common interactions were found, lysine-glutamine, tryptophan-valine, and lysine-glycine/alanine (Table 5).

TABLE 5

Interactions between the defined region of the Cdc50 loop and the ATP11C protein.

| Protein | Protein - "Peptide" | interaction |
|---|---|---|
| 7bsp | K 988 - G 203: 3.3 Å | H-bond, K side chain - G carbonyl |
|  | V 989 - W 206: 2.1 Å | H-bond, V carbonyl - W side chain N—H |
|  | Q 1051 - K 213: 2.2 Å | H-bond, Q carbonyl - K side chain N—H |
| 7bsq | K 988 - A 205: 2.4 Å | H-bond, K side chain - A carbonyl |
|  | V 989 - W 206: 2.3 Å | H-bond, V carbonyl - W side chain N—H |
|  | Q 1051 - K 213: 1.8 Å | H-bond, Q carbonyl - K side chain N—H |
| 7bss | K 988 - A; 205: 2.6 Å | H-bond, K side chain - A carbonyl |
|  | V 989 - W 206: 2.1 Å | H-bond, V carbonyl - W side chain N—H |
|  | Q 1051 - K 213: 2.4 Å | H-bond, Q carbonyl - K side chain N—H |
| 7bsu | K 988 - G 203: 2.8 Å | H-bond, K side chain NH - G carbonyl |
|  | V 989 - W 206: 2.4 Å | H-bond, V carbonyl - W side chain N—H |
|  | Q 1051 - K 213: 2.7 Å | H-bond, Q carbonyl - K side chain N—H |
| 7bsv | K 988 - A 205: 2.5 Å | H-bond, K side chain - A carbonyl |
|  | V 989 - W 206: 2.3 Å | H-bond, V carbonyl - W side chain N—H |
|  | Q 1051 - K 213: 1.9 Å | H-bond, Q carbonyl - K side chain N—H |
| 7bsw | K 988 - A 205: 2.9 Å | H-bond, K side chain - A carbonyl |
|  | V 989 - W 206: 2.2 Å | H-bond, V carbonyl - W side chain N—H |
|  | Q 1051 - K 213: 2.0 Å | H-bond, Q carbonyl - K side chain N—H |

Table 5. Interactions between the defined region of the Cdc50 loop and the ATP11C protein. Key interactions were identified as those where the ATP11C protein was within 5 Å of the homologous Cdc50 peptide loop region. Here the "protein" amino acid is indicated in green and the "peptide" amino acid is indicated in purple.

These key interactions are, therefore, mostly likely analogous to the interactions between AW9 and the P4-ATPase as these are the similar residues in both. The fatty acid tail of the AW9-Ma peptide likely binds closely to this region as well. The inventors hypothesized that the most likely binding pocket for the AW9-Ma would be located where the PS molecule exists in these structures. The closest of these interactions is modelled in PyMol (FIG. 6). Interestingly, the distance between the end of the closest amino acid and the hydrogen of the fatty acid tail is 14 Å. This is roughly the length of a myristic acid. Thus, the lipid tail is within this distance for interacting with the hydrophobic pocket of P4-ATPase where the PS is located. This observation is supported by the previously described data showing that fatty acid tails shorter than 14 carbons deplete the peptide activity.

Example 8—Modifying Peptide AW9-Ma to Replace Lysine for Alanine Removes Activity From the analysis of analogous structures, the inventors hypothesized the lysine residues of the AW9-Ma peptide were crucial for antifungal activity. To address this possibility, three further peptides were created by changing either one or both lysine residues to alanine. These peptides had modifications at residue number 5 lysine (K6A-Ma), residue number 6 lysine (K6A-Ma), and both (K5A;K6A-Ma). The method was similar to the common molecular biology alanine scan technique but using solid phase peptide synthesis rather than mutagenesis. The change from lysine to a nonpolar alanine has the potential to disrupt hydrogen bonding between the flippase and the peptide. Indeed, among these peptides, each of them exhibited a higher MIC value towards the H99 wild-type peptide than the parent peptide (Table 6). These data suggest that the lysine residues are key for interaction of the peptides with the flippase and are thus partly responsible for their antifungal activity.

TABLE 6

MIC values of lysine→alanine mutant peptides against *C. neoformans*.

| Peptide | MIC (μg/mL) |
|---|---|
| K5A-Ma | >128 |
| K6A-Ma | >128 |
| K5A; K6A-Ma | >128 |

Table 6. The MIC values of lysine→alanine mutant peptides against *C. neoformans*. The sequences of each peptide are shown along with their corresponding MIC values. In all cases, the peptides were inactive against *C. neoformans*.

Figure 8:
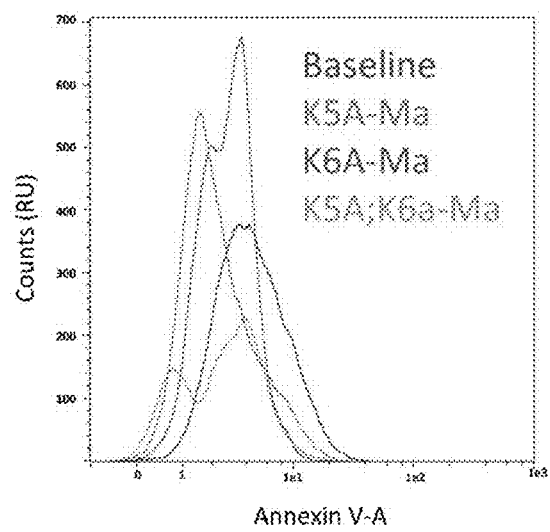

In addition to having different MIC values, the peptides also have a different effect on the accumulation of exofacial PS. For the peptide K5A-Ma the percentage of cells in the gated region of interest was 5.6±0.1%, which was significantly lower than the AW9-Ma peptide (Student's t-test, p-value <0.05). Interestingly, the K6A-Ma showed a more modest decrease in the positive cell population of 17.9±2.1%, though this was still a significant decrease from the AW9-Ma peptide (Student's t-test p-value <0.05). Most interestingly, the double alanine substitution peptide K5A; K6A-Ma caused only 1.3±0.9% of cells to be in this range. (FIG. 8) This value was not even statistically significantly different than the control, untreated cells (Student's t-test p-value >0.1). Retention of one lysine residue provides some activity, with the residue number 6 lysine apparently being more important. It is clear that replacing both lysine residues depletes peptide activity.

CONCLUSIONS AND DISCUSSION

Peptides have been developed based on the Cdc50a loop region that have antifungal activity against *C. neoformans*. The most successful peptide was labelled AW9-Ma and was derived from nine residues in Cdc50a with a myristic acid tail. Furthermore, when used in combination with caspofungin, the FIC of caspopfungin drop to 4 μg/mL. It is noted that this is the same value as the previously reported MIC for the cdc50Δ mutant strain against caspofungin.

This peptide not only successfully inhibited the growth of H99 C. neoformans but it also caused significant changes in the properties of the cell membrane. Peptide accumulation was detected on the membrane and its co-localization with the flippase P4-ATPase Apt1. The accumulation of exofacial PS can have a detrimental effect on the stability of the membrane.(26) One such effect is an increased susceptibility of peptide-treated cells to SDS similar to the cdc50Δ phenotype. The fungal cells treated with AW9-Ma showed increased exofacial phosphatidylserine as monitored by an AF350-annexin V-PI assay. Together, these results suggest that AW9-Ma binds to the flippase and promotes exofacial PS on the cell membrane.

Figure 9:
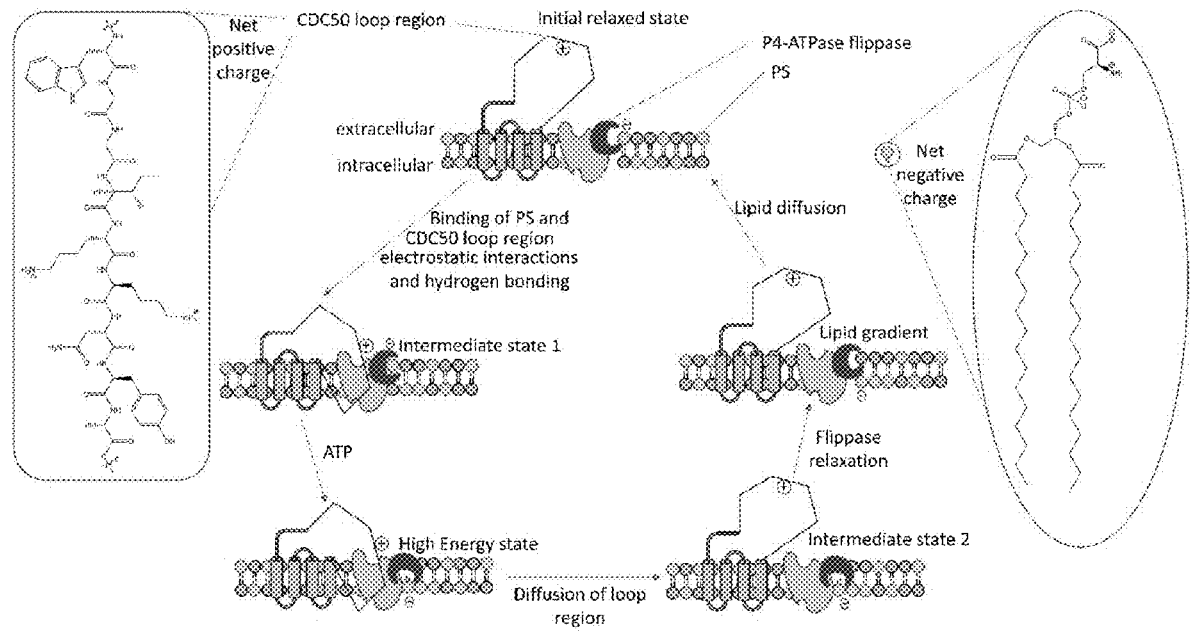
Figure 10:
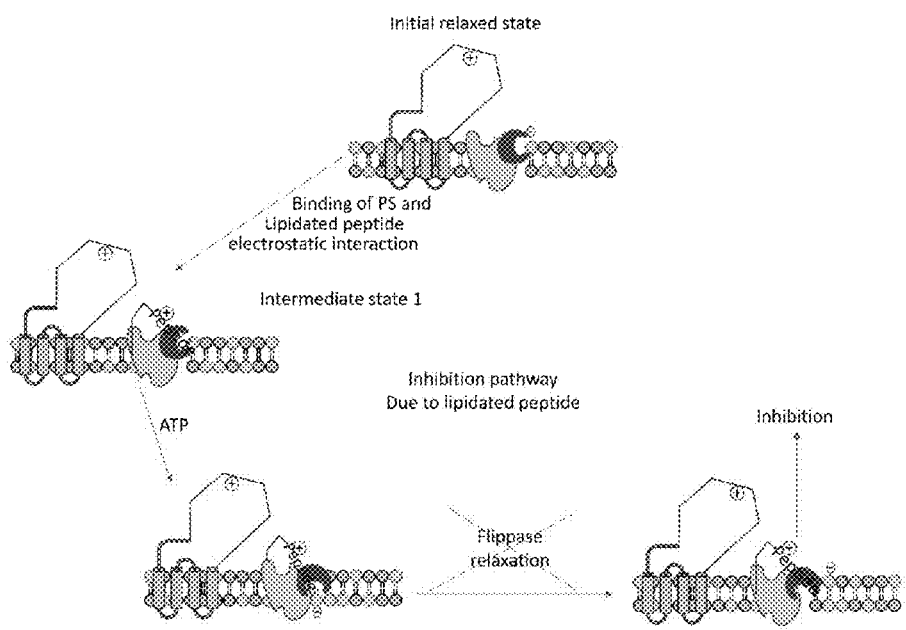

Taking these results into consideration we propose a mechanism of peptide activity. Opening of channel region (red) is required for shuttling of lipids from one side of the membrane to the other (FIG. 9). Normal P4-ATPase function is regulated by diffusion of the Cdc50 loop region out of the binding pocket in the P4-ATPase-Cdc50 complex. This is required for the flippase to relax back to an initial state. In the absence of the peptide, the Cdc50 loop region binds to complex through specific hydrogen bonds and electrostatic interactions. In the presence of a molecule such as AW9-Ma, these bonds are replaced by interactions with the peptide (FIG. 10). This is supported by our data showing that truncated peptides lacking the lysine residues as well as Lys→Ala modified AW9-Ma all have decreased activity. The enzyme will eventually become locked in a peptide-bound conformation, unable to relax back to the initial state. Thus, further lipid flipping is prevented.

It is within the scope of this disclosure for future work to further validate the precise mechanism of the peptide action. Specifically, an alanine scan of Cdc50 in vivo could address whether Lys→Ala mutants exhibit a similar phenotype to cdc50Δ. Modifications to the peptides can be implemented in the future to tune the specificity of the peptide to fungal membranes over mammalian membranes.

Possible modifications include post translational modifications, like side chain glycosylation, cyclization, substitution with amino acid derivatives, or unnatural-D amino acids. Along these lines, future peptide modifications should attempt to tune the hydrophobic moment of the peptide to fungal membranes with different types of branched and unsaturated fatty acid tails, or fatty acid tail derivatives like Beta-hydroxymyristic acid.

Further complications exist in the fact that the importance of 1,3-β-D glucan for C. neoformans survival is debated.

Overall, however, AW9-Ma is a promising candidate with a plausible activity that could serve as a useful molecule to improve C. neoformans susceptibility to caspofungin.

While exemplary embodiments have been described herein, it is expressly noted that these embodiments should not be construed as limiting, but that additions and modifications to what is expressly described herein also are included within the scope of the invention.

Moreover, it is to be understood that the features of the various embodiments described herein are not mutually exclusive and can exist in various combinations and permutations, even if such combinations or permutations are not made express herein, without departing from the spirit and scope of the invention.

The following is given to further supplement the above examples. Again these materials are merely to permit further illustration of the principles of the invention and not meant to limit the scope to these specific examples.

Related Supplemental Materials Supporting the Above Examples

| | | | FIC ug/mL | | | | | |
|---|---|---|---|---|---|---|---|---|
| | MIC ug/mL | | $H_{99}$ | | $\Delta CDC_{50}$ | | FIC Index | |
| Sequence | $H_{99}$ | $\Delta CDC_{50}$ | Caspofungin | Peptide | Caspofungin | Peptide | $H_{99}$ | $\Delta CDC_{50}$ |
| Caspofungin | 16 | 4 | — | — | — | — | — | — |
| QY15 | >128 | >128 | 8 | 0.5 | 1 | 0.5 | 0.5-1 | 0.5-1 |
| QY15-Ma | >128 | 128 | 8 | 0.5 | 1 | 0.5 | 0.5-1 | 0.25 |
| AS15 | >128 | 128 | 8 | 0.5 | 1 | 0.5 | 0.5-1 | 0.25 |
| AS15-Ma | >128 | 8 | 8 | 0.5 | 0.25 | 0.25 | 0.5-1 | 0.094 |
| AS15-Aa | >128 | >128 | — | — | — | — | — | — |
| AS15-Ha | >128 | >128 | — | — | — | — | — | — |
| AS15-Da | >128 | >128 | — | — | — | — | — | — |
| AW9-Ma | 64 | 2 | 4 | 16 | 0.125 | 0.125 | 0.5 | 0.094 |
| KS9-Ma | >128 | >128 | — | — | — | — | — | — |
| GS9-Ma | >128 | >128 | — | — | — | — | — | — |
| AS15-Pa | >128 | 128 | 8 | 0.5 | 2 | 2 | 0.5-1 | 0.53 |
| AW9-Pa | >128 | 8 | 8 | 0.5 | 2 | 1 | 0.5-1 | 0.75 |

S1. Table comprising all values of MIC, FIC, and FIC Index determined throughout the paper against wild-type and mutant strains.

| Peptide | Amount mg (Crude) | Yield % (Crude) | Amount mg (Purified) | Yield % (Purified) | Purity (%) |
|---|---|---|---|---|---|
| AS15 | 176.23 | 111.5 | 123.98 | 78.43 | 99.2 |
| AS15-MA | 199.5 | 111.4 | 120.61 | 67.34 | 97.5 |
| QY15 | 191.52 | 102.6 | 68.86 | 36.9 | 96.4 |
| QY15-MA | 186.19 | 89.67 | 133.68 | 64.38 | 96 |
| AS15-AC | 190.91 | 117.6 | 162.15 | 99.9 | 99.0 |
| AS15-HEX | 160.78 | 95.76 | 91.82 | 54.7 | 99.3 |
| AS15-DA | 179.14 | 103.3 | 132.13 | 76.2 | 98.4 |
| AW9-MA | 129.83 | 104.1 | 77.64 | 62.3 | 87.6 |
| KS9-MA | 107.14 | 97.54 | 72.85 | 66.3 | 81.1 |
| GS9-MA | 105.90 | 98.76 | 36.72 | 34.2 | 70.5 |
| AS15-Pa | 178.10 | 97.9 | 105.43 | 59.7 | 76 |
| AW9-Pa | 134.51 | 105 | 58.24 | 46.5 | 93.7 |

S4. Yield and purity of peptides before and after HPLC purification.

| | Expected | | | | Crude | | Purified | |
|---|---|---|---|---|---|---|---|---|
| | Mass | Calculated m/z | | | Observed | | Observed | |
| Peptide | (Da) | +1 | +2 | +3 | m/z | Comment | m/z | Comment |
| AS15 | 1580.76 | 1581.77 | 791.39 | 527.92 | 790.5 | +2 | 790.4 | +2 |
| AS15-Ma | 1791.13 | 1792.13 | 896.57 | 598.04 | 895.5 | +2 | 895.5 | +2 |
| QY15 | 1865.98 | 1866.99 | 934.0 | 622.99 | 932.9 | +2 | 932.9 | +2 |
| QY15-Ma | 2076.34 | 2077.35 | 1039.18 | 693.11 | 1038.3 | +2 | 1038.4 | +2 |
| AS15-Ac | 1622.80 | 1623.80 | 812.4 | 541.93 | 1623.1, 812.5 | +1, +2 | 812.3 | +2 |
| AS15-Ha | 1678.91 | 1679.91 | 840.455 | 560.63 | 1679, 839.45 | +1, +2 | 840.5 | +2 |
| AS15-Da | 1733.94 | 1734 | 867.97 | 578.98 | 867.55 | +2 | 869.6 | +2 |
| AW9-Ma | 1246.56 | 1247.56 | 624.28 | 416.52 | 1246.95, 623.6 | +1, +2 | 1247.7; 624.0 | +1, +2 |
| KS9-Ma | 1098.40 | 1099.40 | 550.2 | 367.13 | 1099, 550.6 | +1, +2 | 1098.7, 551.0 | +1, +2 |
| GS9-Ma | 1072.27 | 1073.27 | 537.135 | 358.42 | N/A | N/A | 1095.6 | +1, Na adduct |
| AS15-PA | 1819.18 | 1820.18 | 910.59 | 607.39 | 909.2 | +2 | 910.0 | +2 |
| AW9-PA | 1274.62 | 1275.62 | 638.31 | 425.87 | 1274.3, 637.7 | +1, +2 | 1275.6; 637.8 | +1, +2 |

S5. Mass Spectroscopy results for peptide predicted monoisotopic mass

What is claimed is:

1. An antifungal peptide targeting a P4-ATPase function peptide, the antifungal peptide having the following formula:

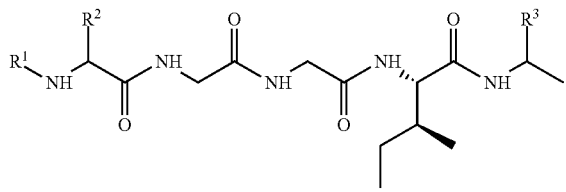

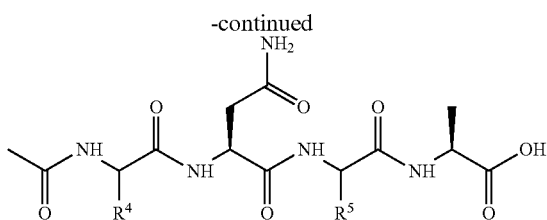

wherein,
R1 is —C(O)RA, wherein RA is a C1 to C14 alkyl group,
R2 is an alkyl group, a hydroxyl group, a phenol group, a phenyl group, or an indole group,
R3 is an alkyl group, an alkylamine group, a diamine group, or an indole group,
R4 is a hydrogen, an alkyl group, a diamine group, or alkylamine group, and
R5 is alkyl group, a alkylamide group, or a phenyl group having a hydroxyl substituent.

2. The antifungal peptide of claim 1, wherein the antifungal peptide has any one of the following formulas:

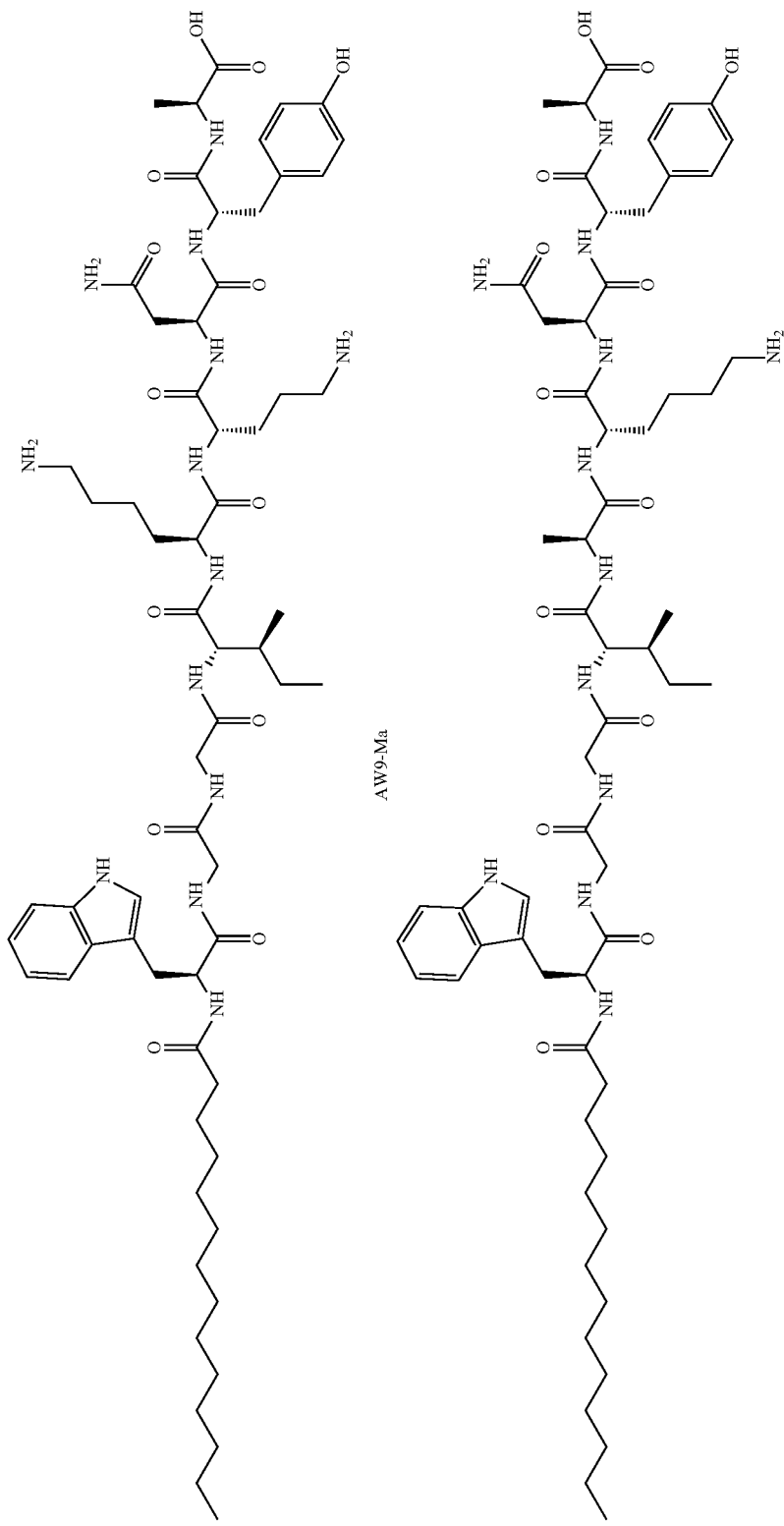

-continued
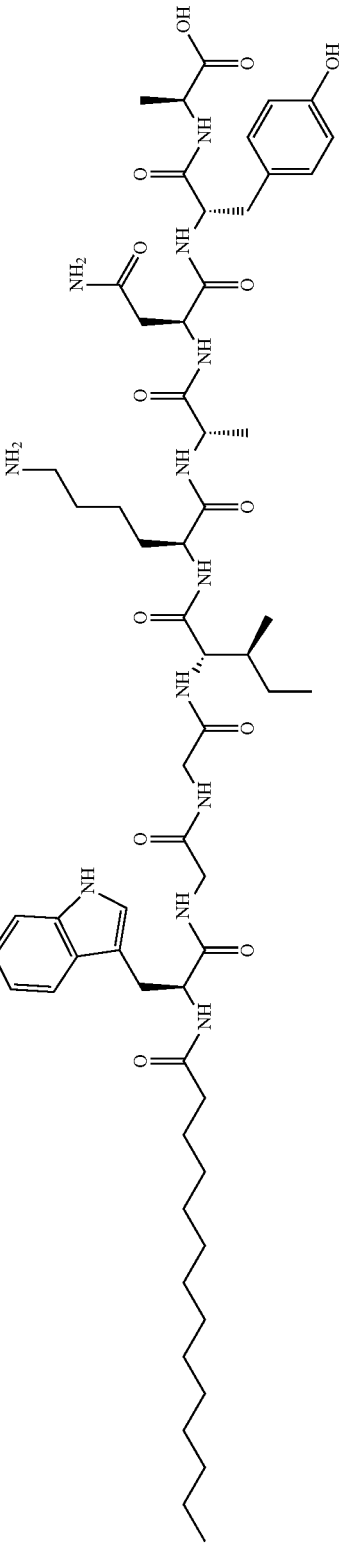
AW9-Ma-K6A (K6A)
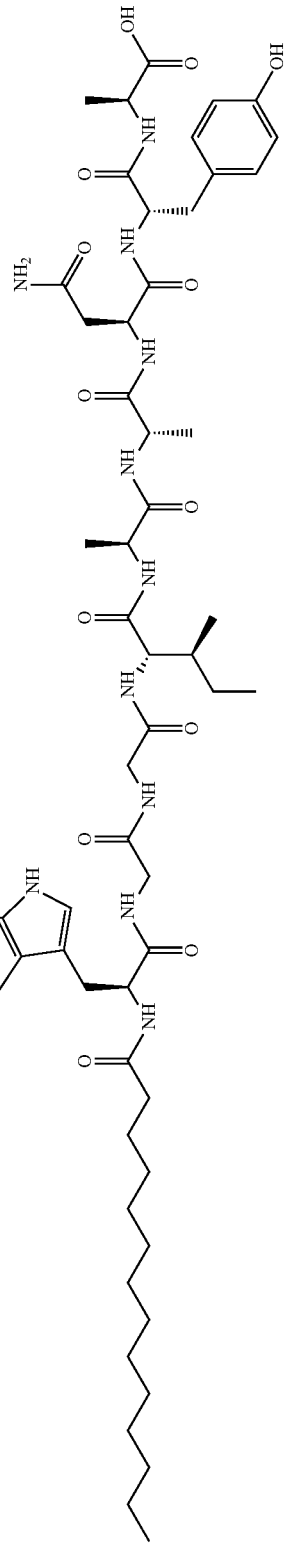
AW9-Ma-K5A;K6A (K5A;K6A)

-continued
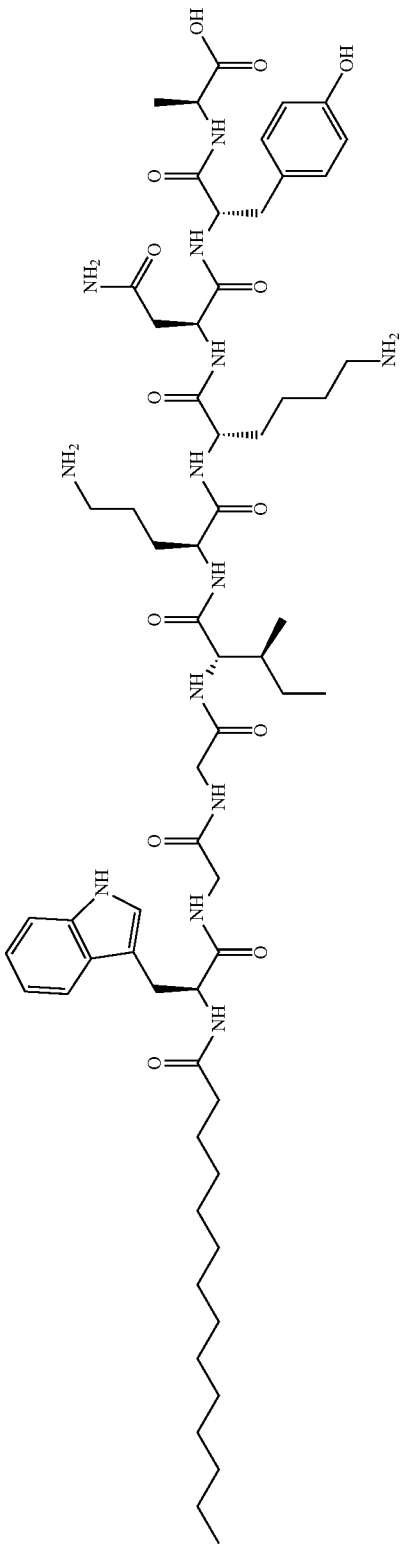
AW9-Ma-K5O (K5O)
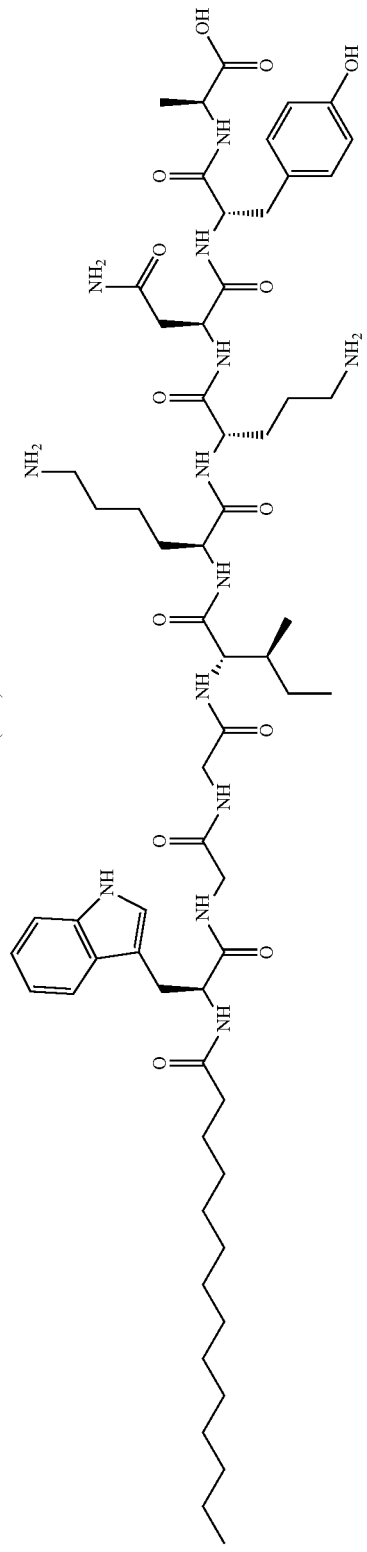
AW9-Ma-K6O (K6O)

-continued
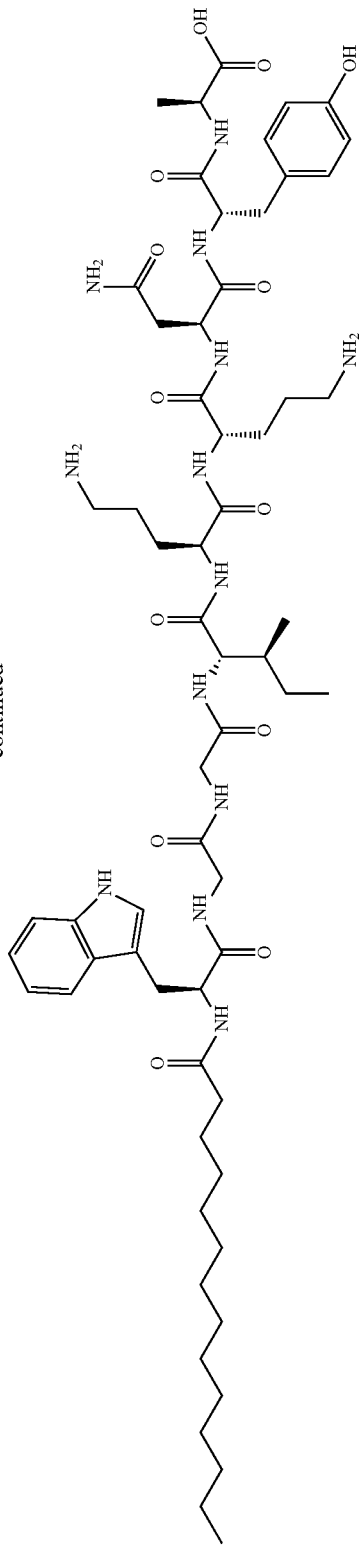
AW9-Ma-K5O;K6O (K5O;K6O)
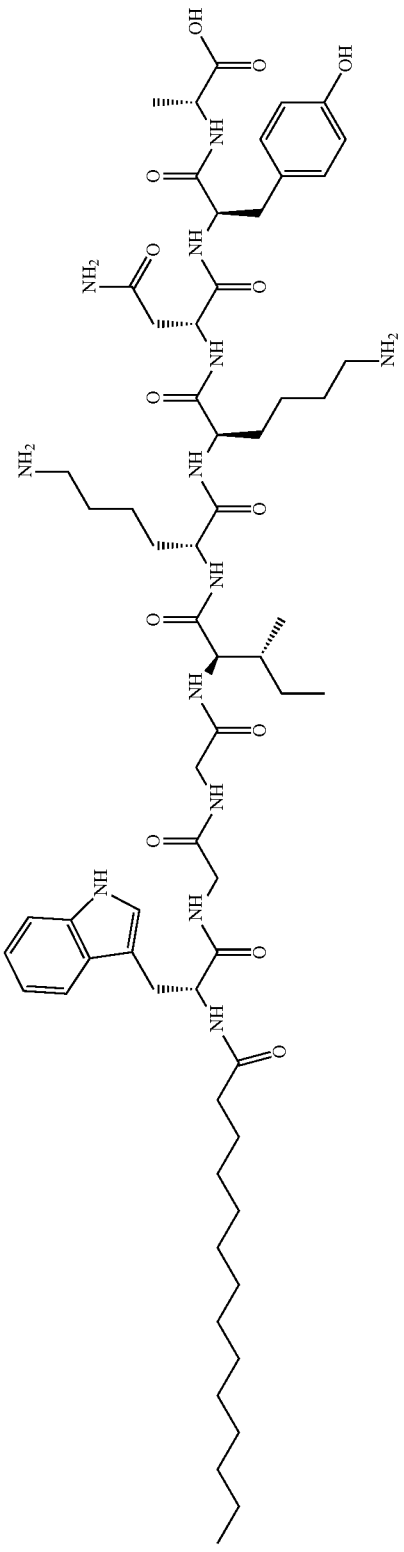
AW9-Ma-D

-continued
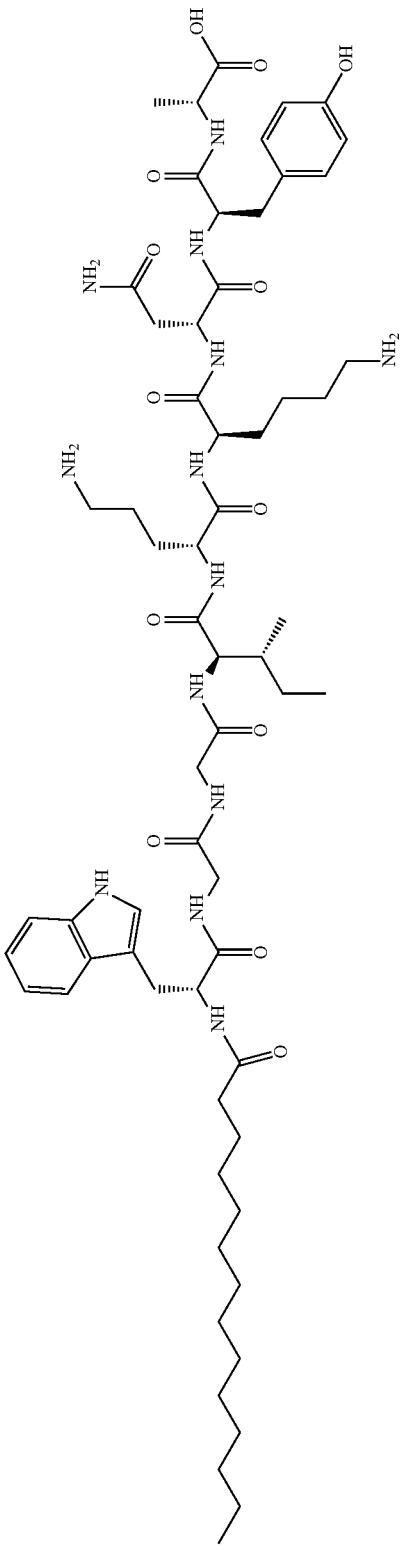
AW9-Ma-K5O-D (K5O-D)
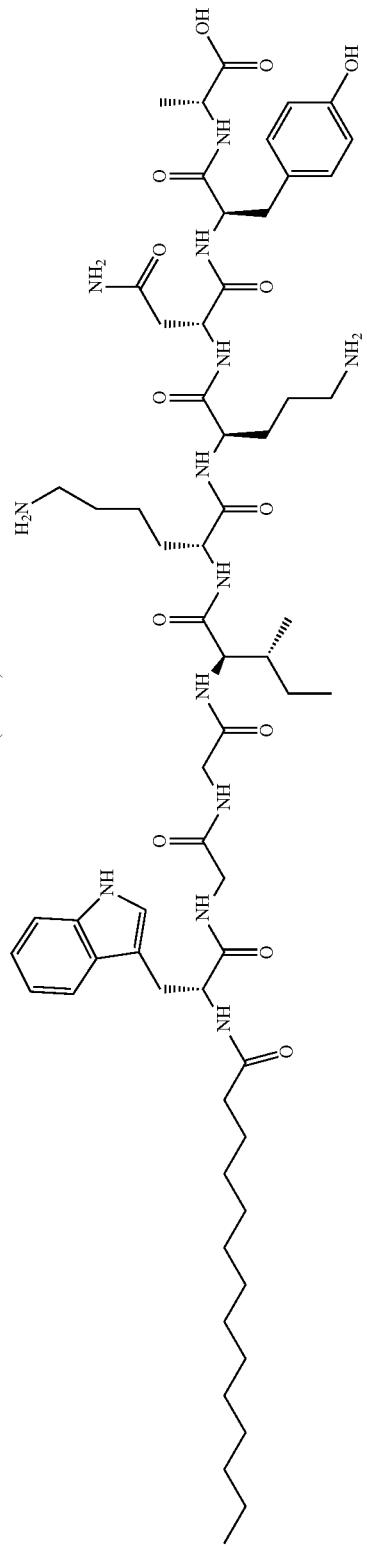
AW9-Ma-K6O-D (K6O-D)

-continued
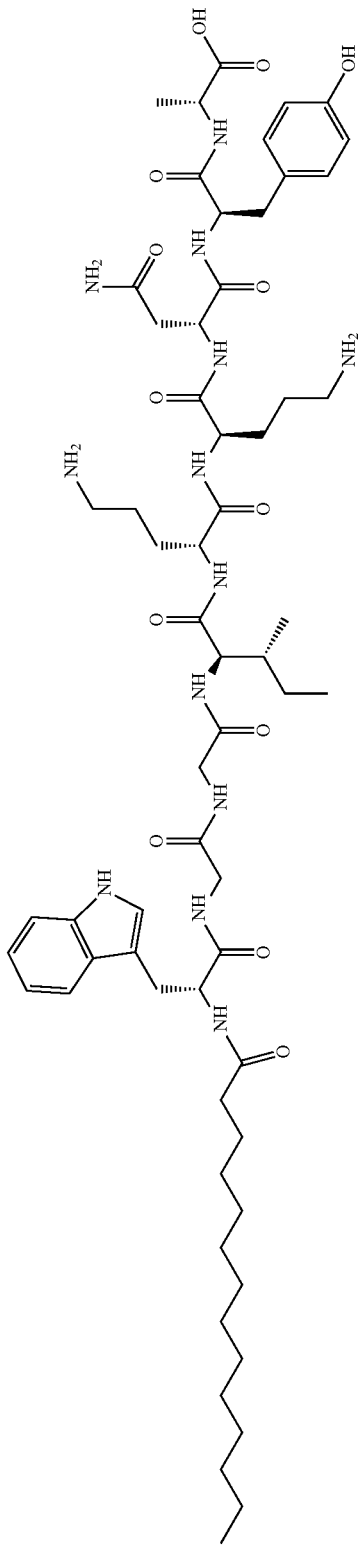
AW9-Ma-K5O;K6O-D (K5O;K6O)
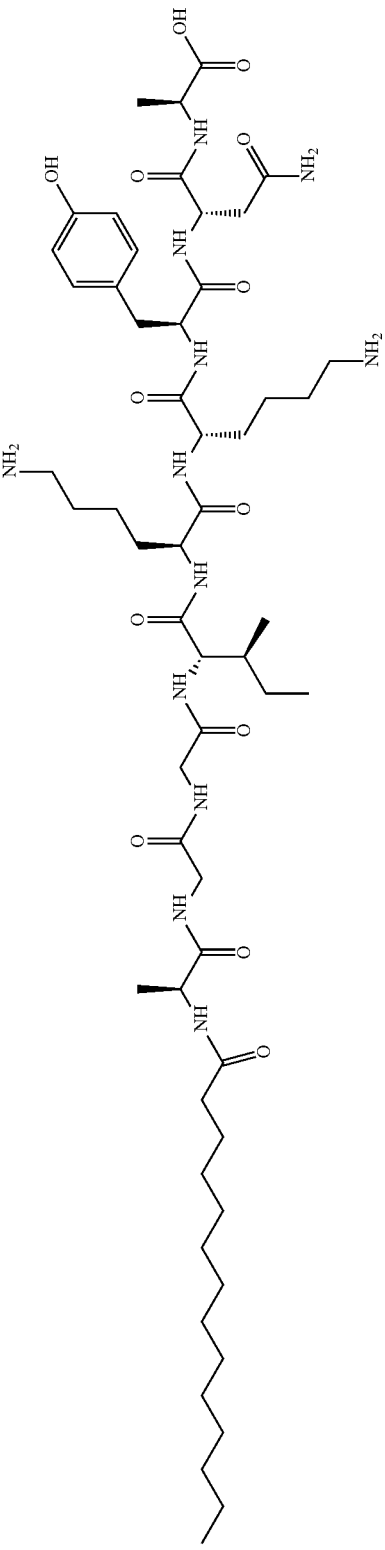
AW9-A1

-continued
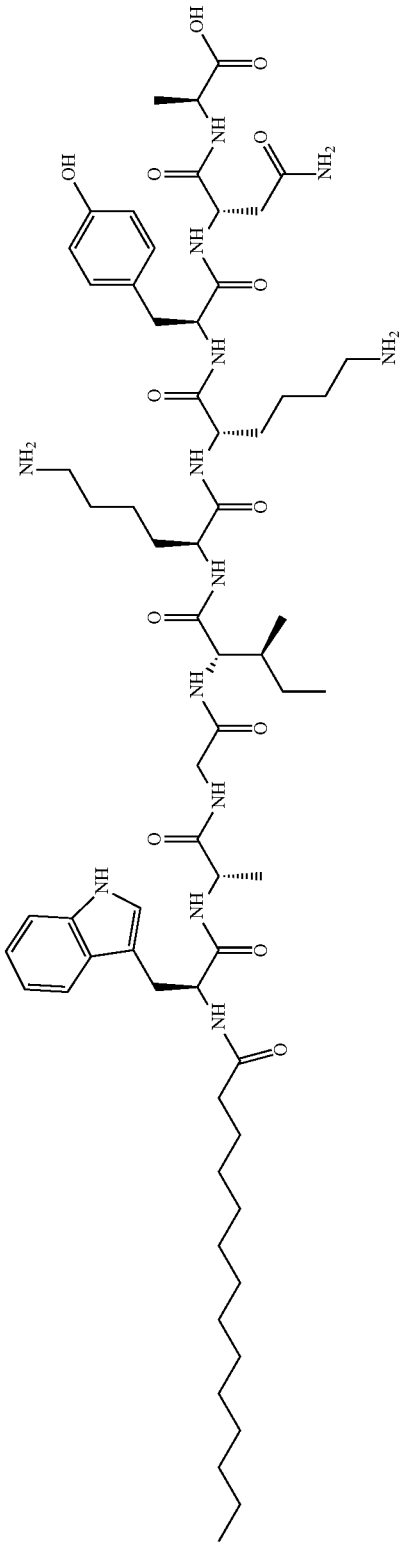
AW9-Ma-A2
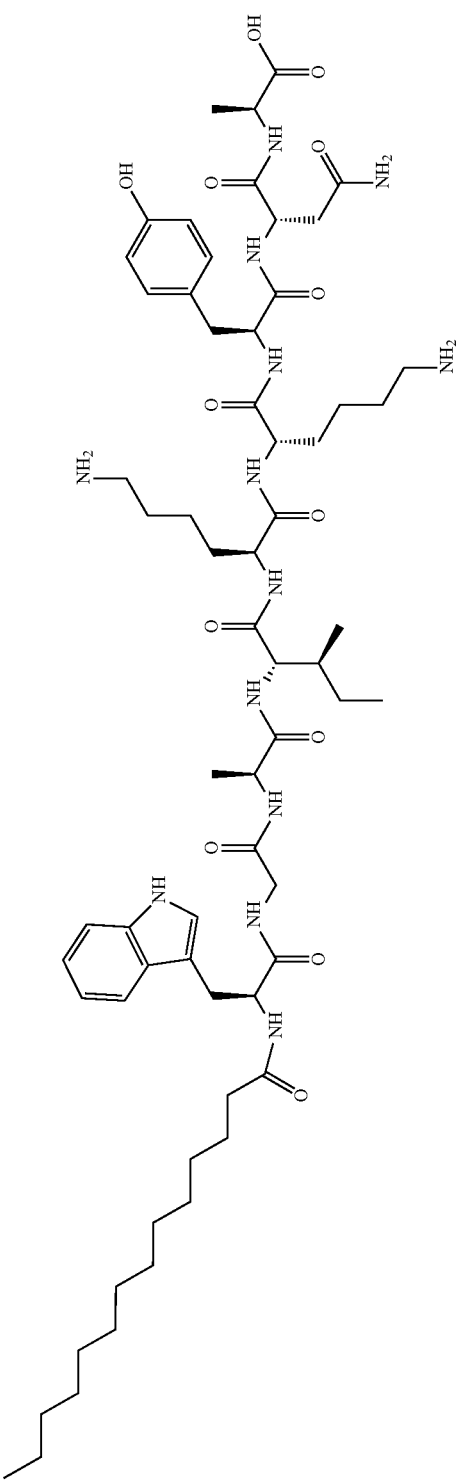
AW9-Ma-A3

-continued
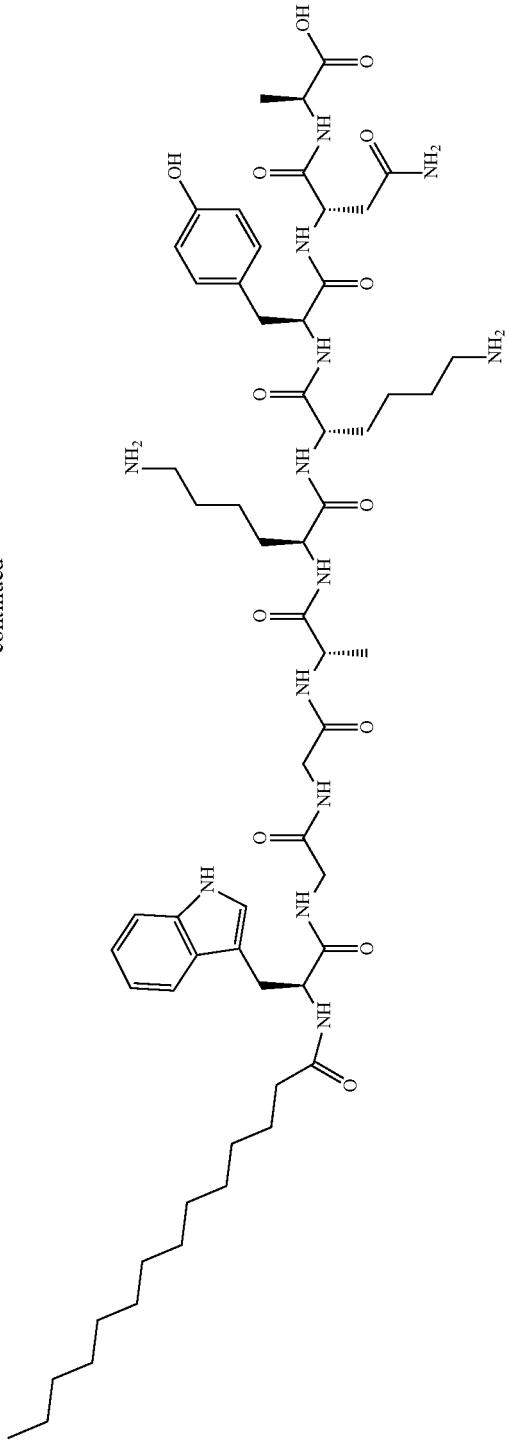
AW9-Mα-A4
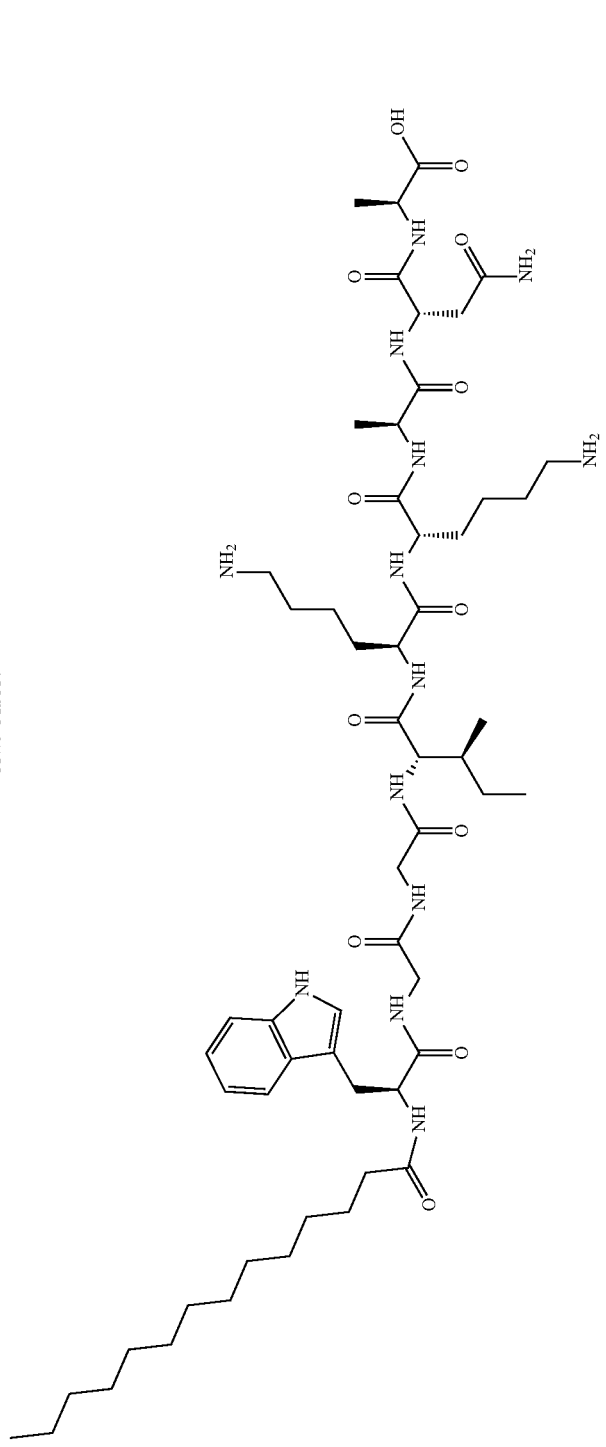
AW9-Mα-A7

-continued
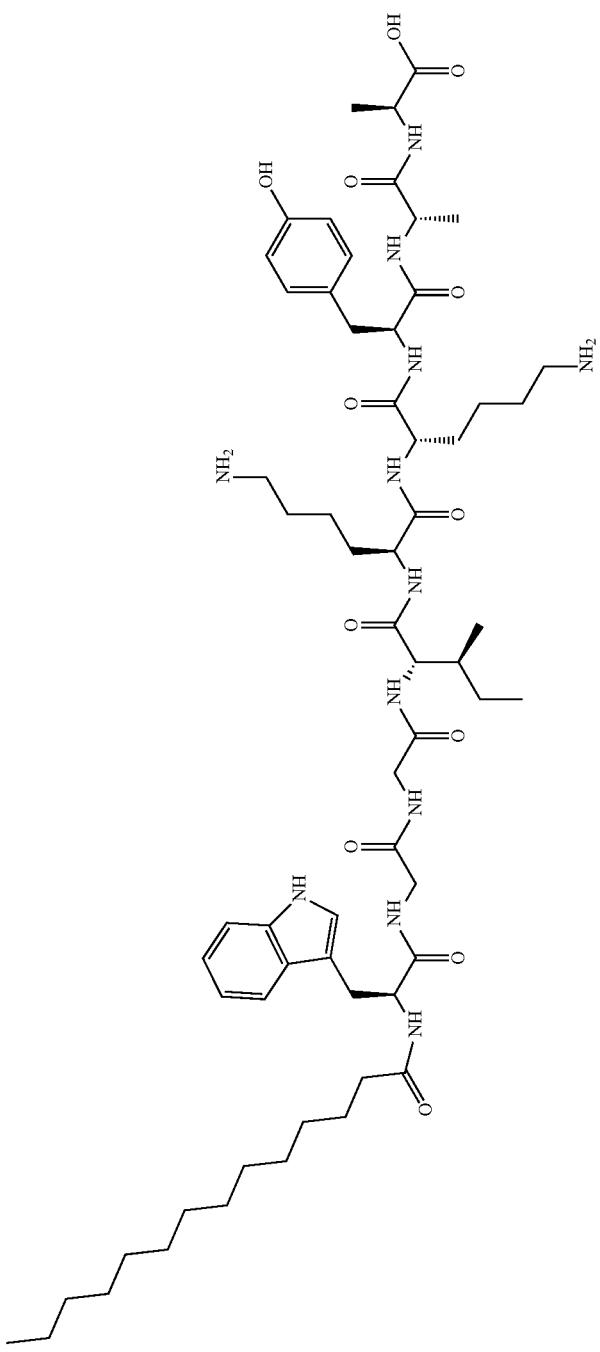
AW9-Ma-A8
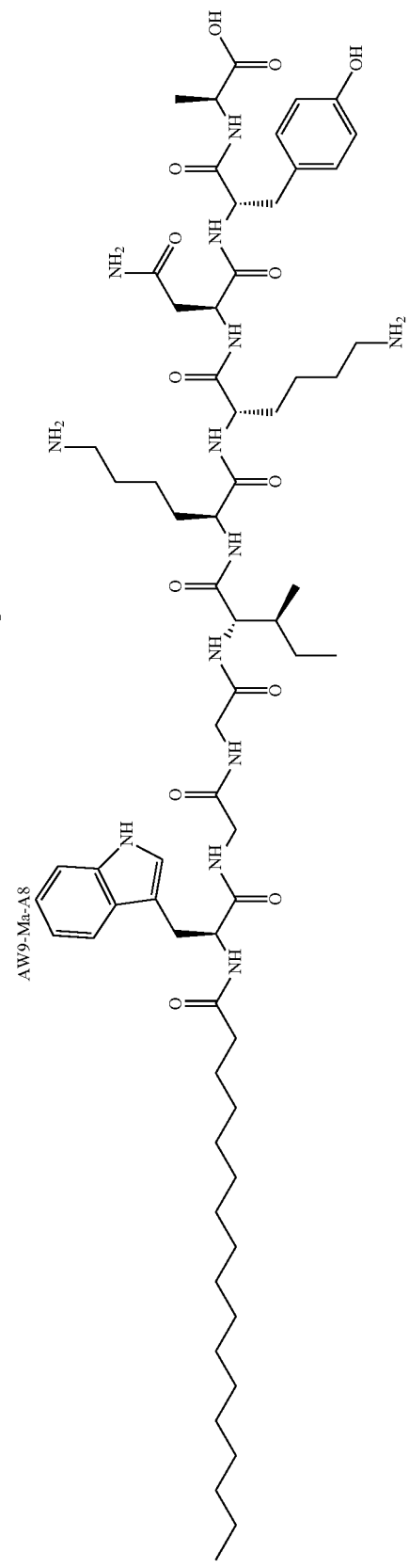
AW9-Pa

-continued
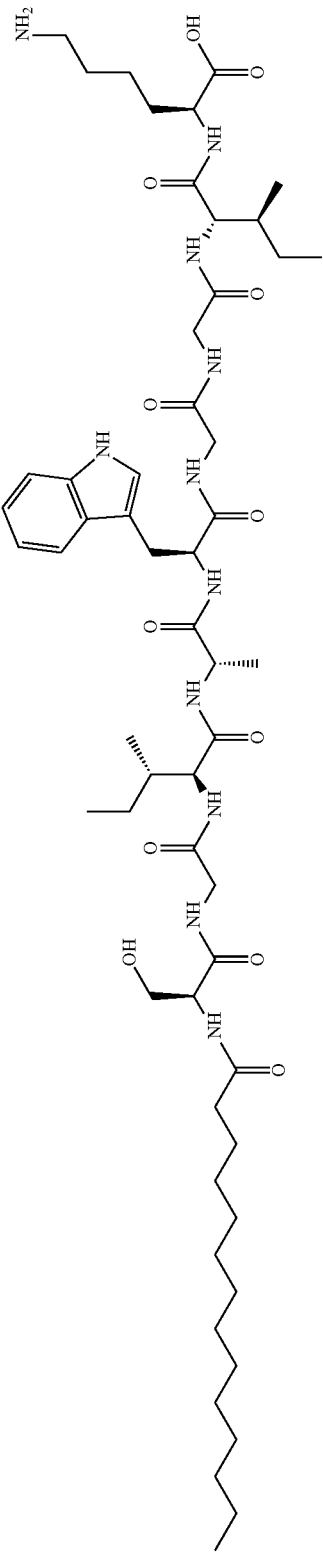
KS9-Ma
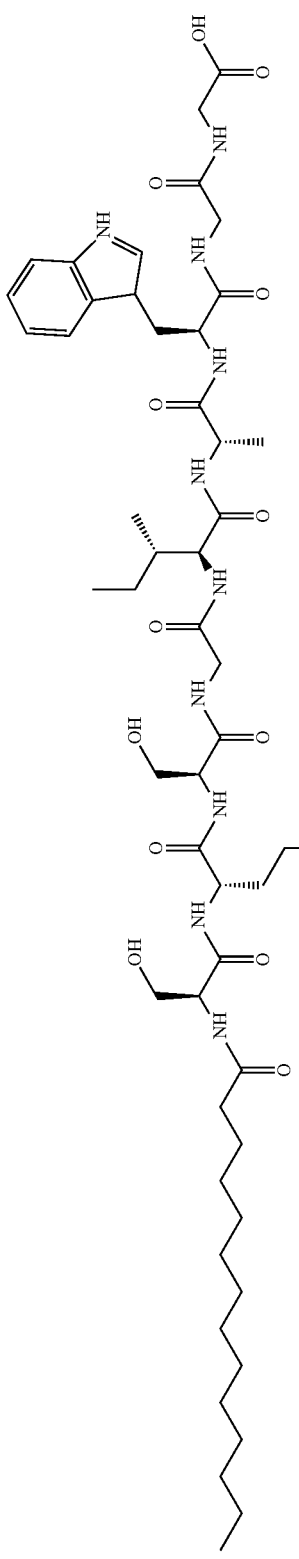
GS9-Ma

-continued
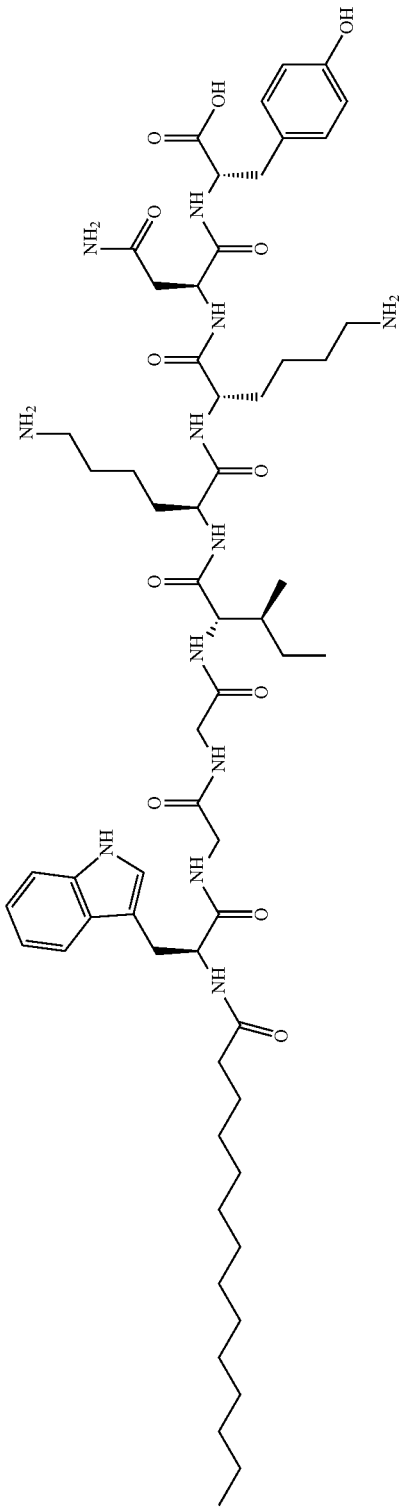
YW8-Ma
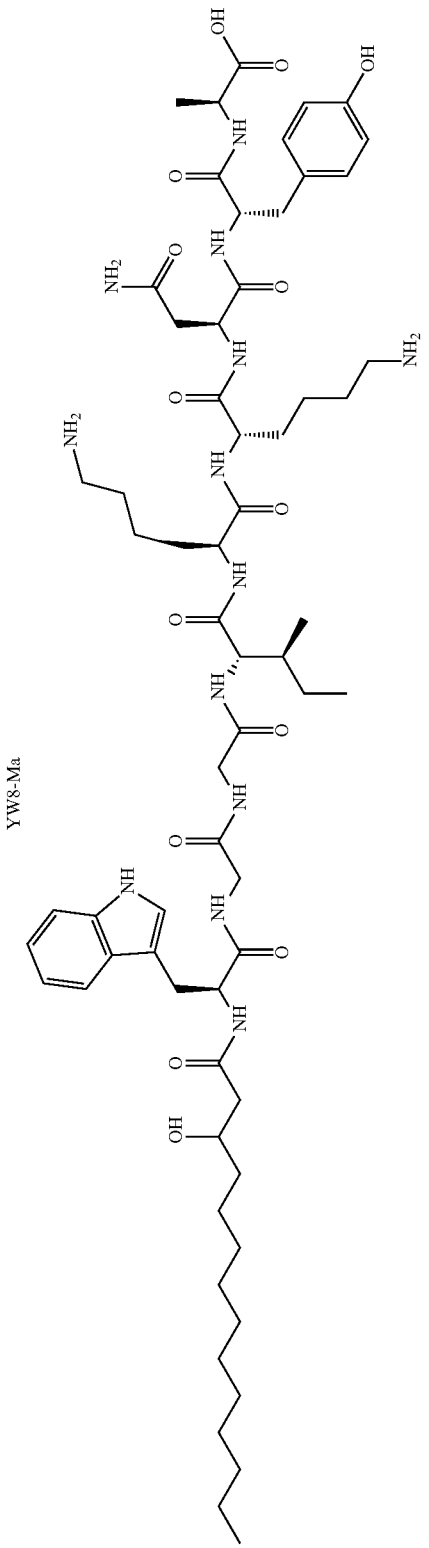
AW9-βHMa

-continued
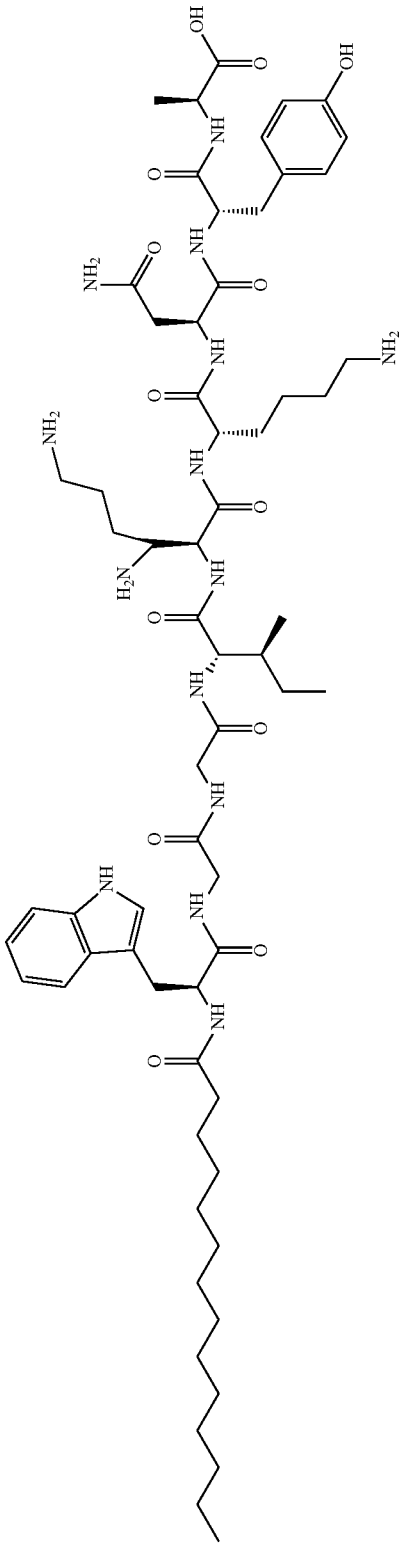
AW9-K5Dab
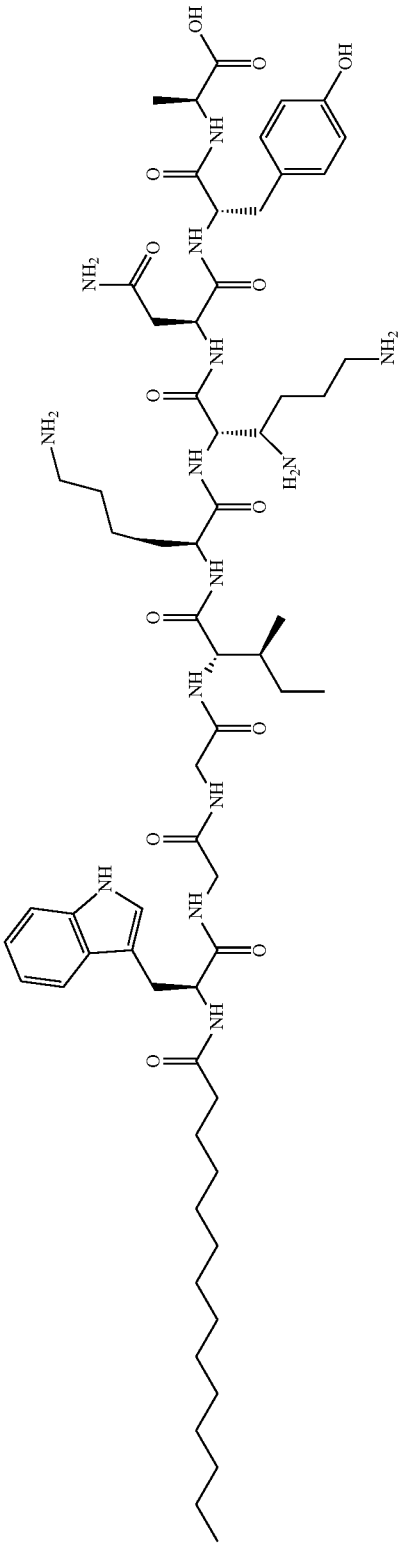
AW9-K6Dab

-continued
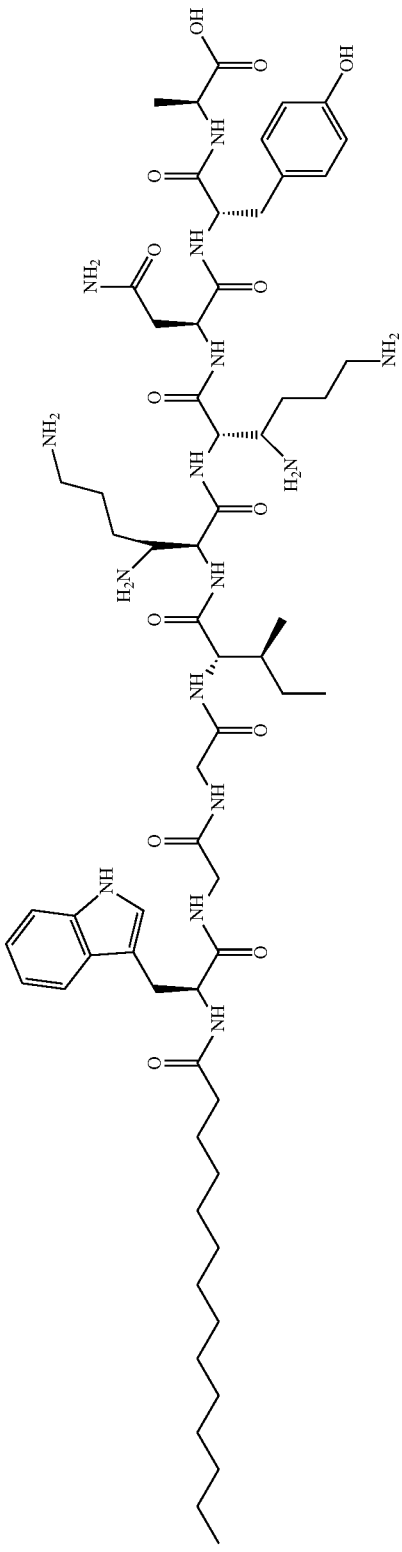
AW9-KKDabDab
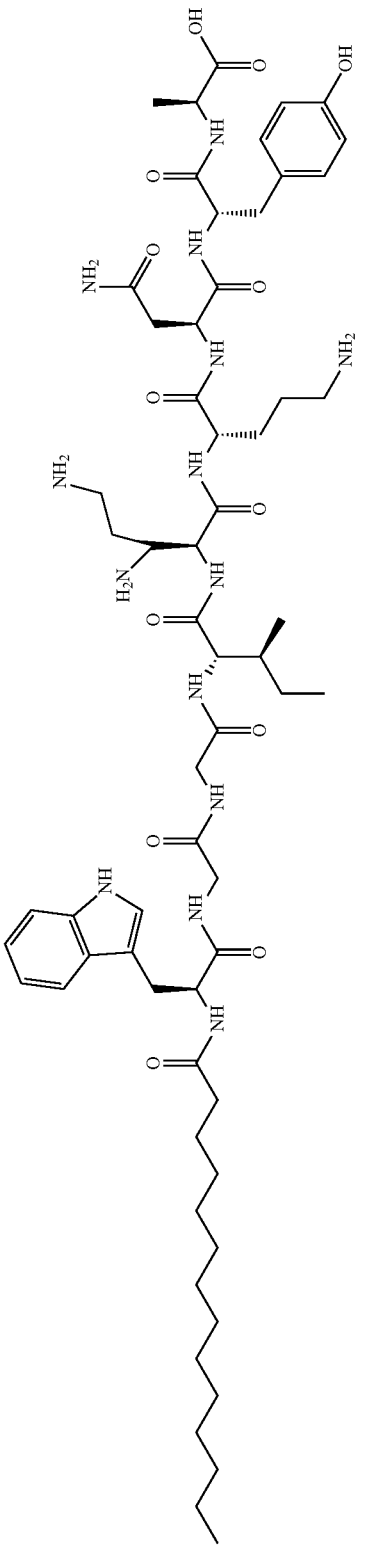
AW9-K5Dap

-continued
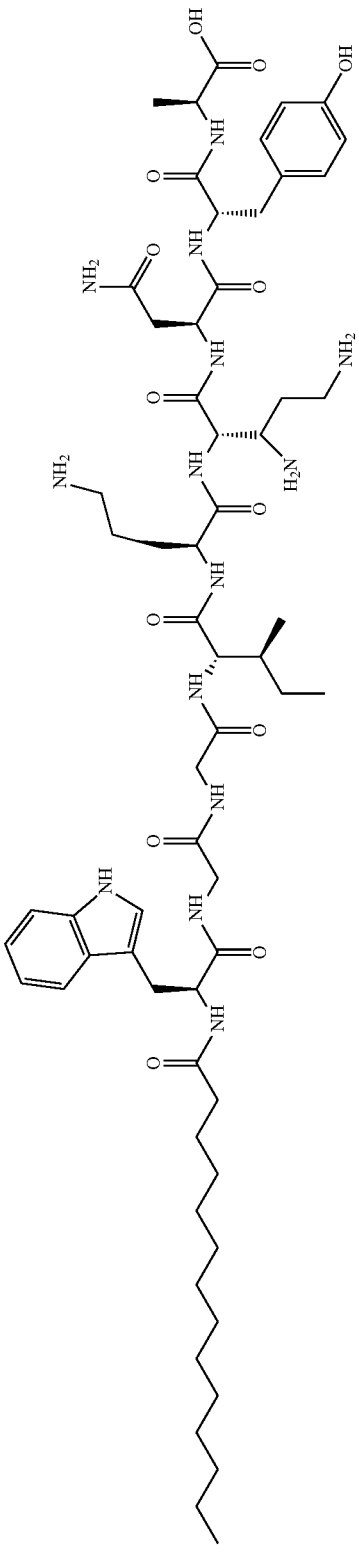
AW9-K6Dap
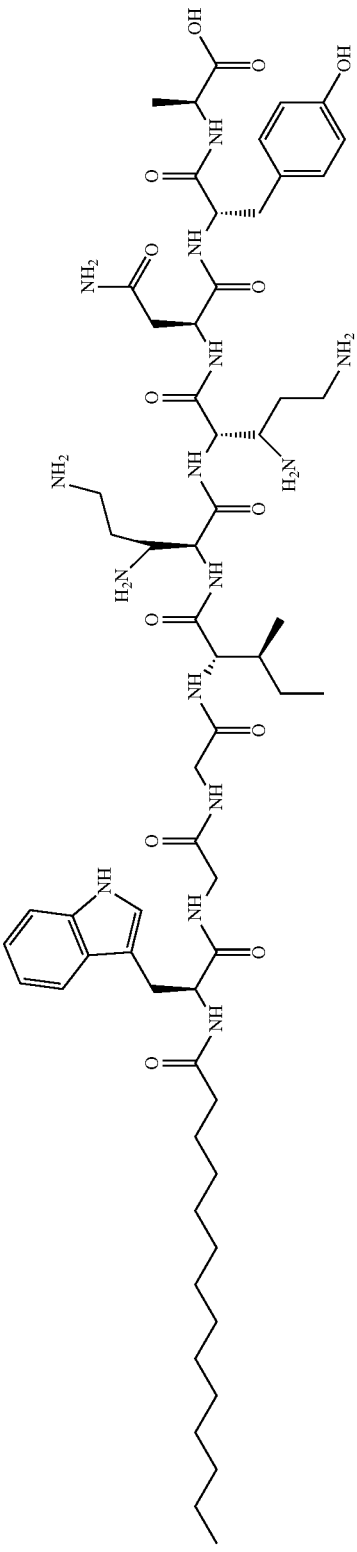
AW9-KKDapDap

3. An antifungal peptide targeting a P4-ATPase function peptide, the antifungal peptide having any one of the following formulas:

83 84
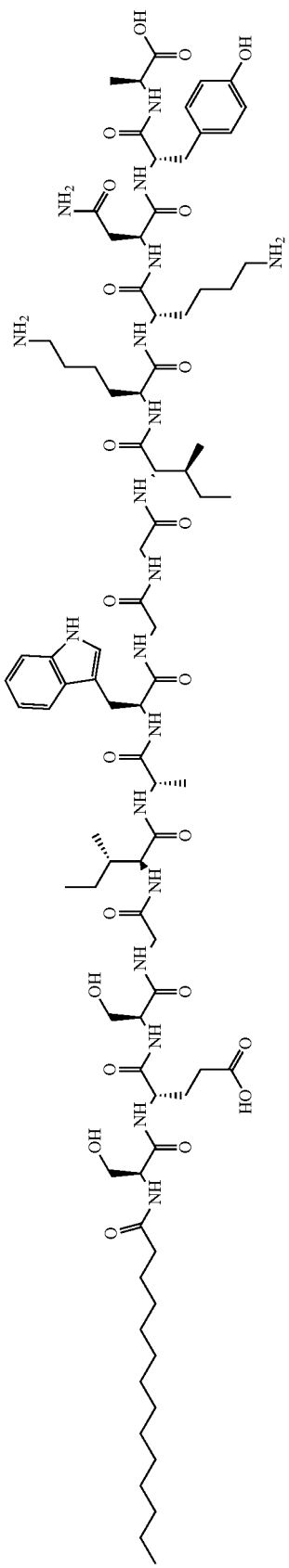
AS15-Ma
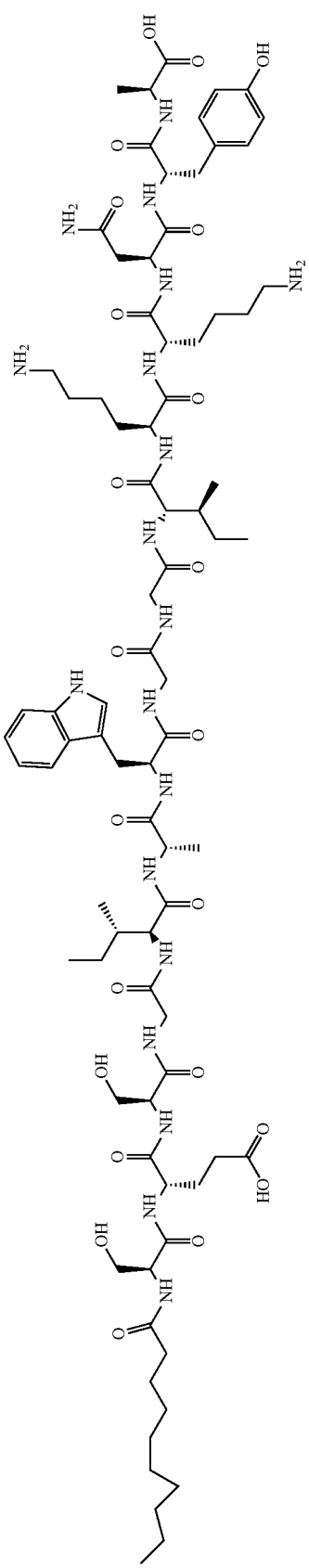
AS15-Da
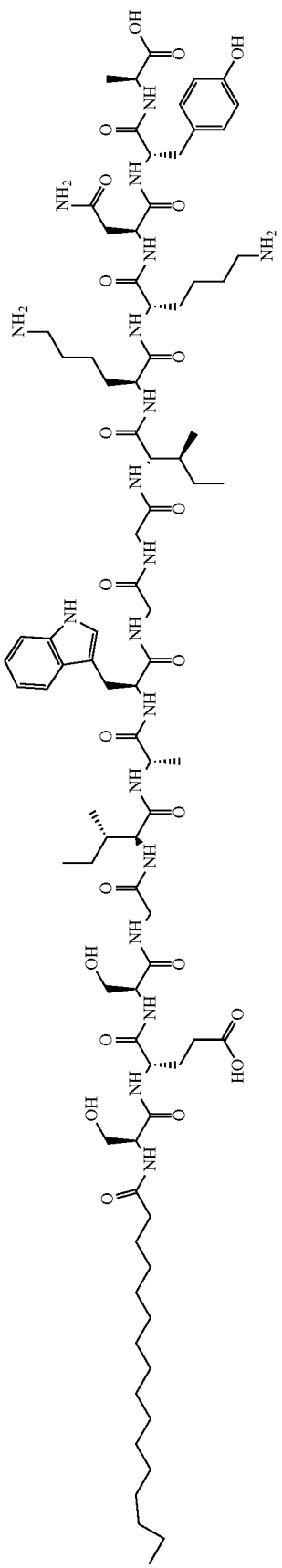
AS15-Pa

-continued
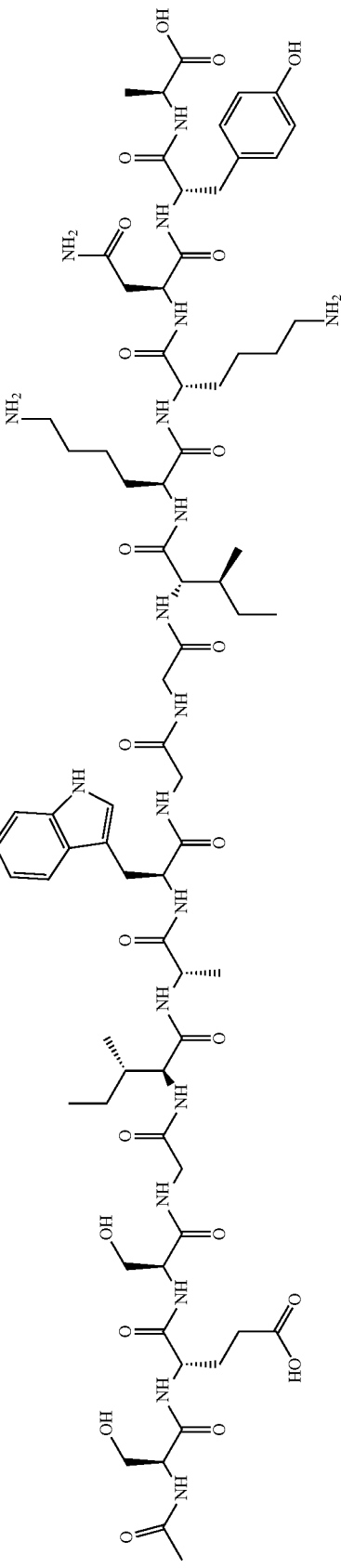
AS15-Ac
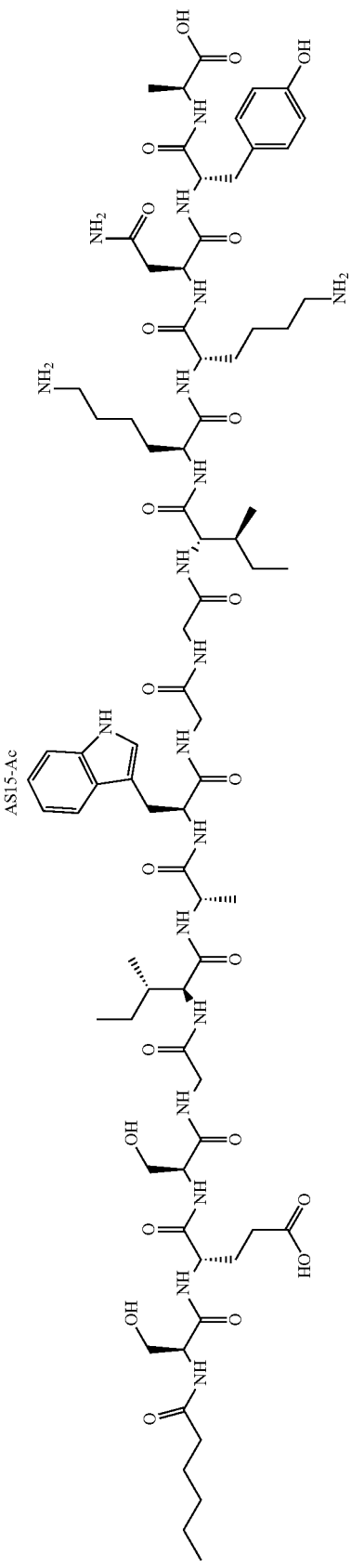
AS15-Ha
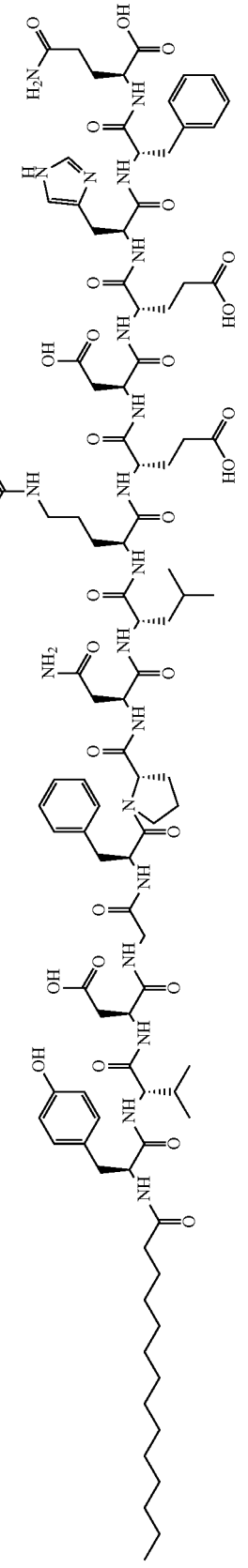
QY15-Ma

4. The antifungal peptide of claim 1 further comprising a pharmaceutical bound to the peptide and selected from a group consisting of caspofungin, itraconazole, amphotericin B, poly-L-lysine, chlorhexidine, and any combination thereof.

5. The antifungal peptide of claim 4, wherein the pharmaceutical is an antifungal drug and the peptide causes charged lipid molecules to be retained on a surface of the peptide for the peptide to work in synergy with the antifungal drug.

6. The antifungal peptide of claim 5, wherein the antifungal drug is a caspofungin or an echinocandin.

7. The antifungal peptide of claim 6, wherein the peptide provides use of lower concentration of the caspofungin as compared to use of the caspofungin without the antifungal peptide to treat an infection with similar effectiveness.

8. The antifungal peptide of claim 7, wherein the infection is a *C. neoformans* infection.

9. The antifungal peptide of claim 1, wherein the peptide is AW9-Ma or AW9-Ma-K5O (K5O).

10. The antifungal peptide of claim 1, further comprising one or more additional pharmaceutically acceptable agents.

11. The antifungal peptide of claim 10, wherein the one or more additional pharmaceutically acceptable agent is selected from a group consisting of caspofungin, itraconazole, amphotericin B, poly-L-lysine, chlorhexidine, and any combination thereof.

12. A method of treating a patient infected with *Cryptococcus neoformans*, comprising:
administering to a patient in need thereof an effective amount of an antifungal peptide of claim 1.

13. The method of claim 12 wherein the antifungal peptide is administered alone, or in combination with a therapeutically effective amount of one or more additional pharmaceutically acceptable agents.

14. The method of claim 13 wherein the one or more additional pharmaceutically acceptable agents is selected from the group consisting of caspofungin, itraconazole, amphotericin B, poly-L-lysine, chlorhexidine, and any combination thereof.

15. The method of claim 12, wherein the peptide is AW9-Ma or AW9-Ma-K5O (K5O).

16. The method of claim 14, wherein the peptide sensitize the caspofungin by blocking a flippase function.

17. The method of claim 15, wherein AW9-Ma provides minimum inhibitory concentration (MIC) of 64 µg/mL against H99 wild type and fractional inhibitory concentration (FIC) index value of 0.5 when used with caspofungin.

18. The method of claim 15, wherein AW9-Ma in combination with caspofungin provides a concentrate-dependent minimal amount of hemolysis as compared to using just caspofungin.

19. The method of claim 18, further includes causing interference of P4-ATPase and possible damage of a RBC membrane.

20. The method of claim 15, wherein when AW9-Ma is used in combination with caspofungin, the FIC of caspopfungin drop to 4 µg/mL.

21. The antifungal peptide of claim 1, wherein the antifungal peptide has the following formula:

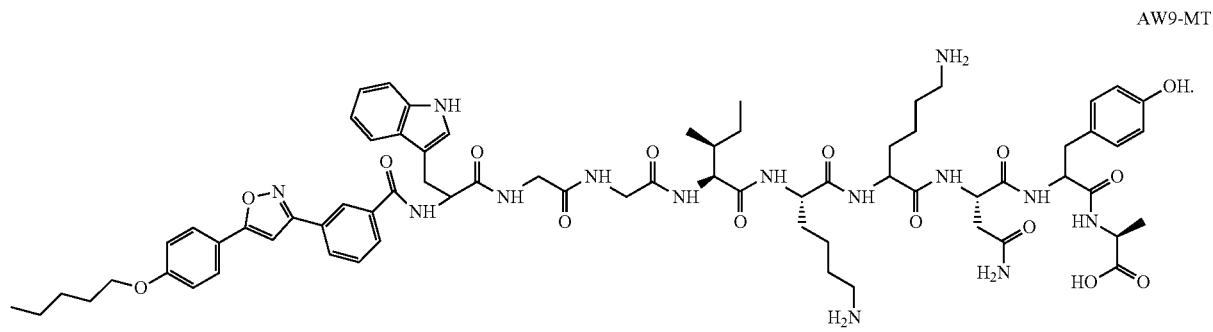 [SMILES: CCCCCOc1ccc(-c2cc(-c3cccc(C(=O)NC(Cc4c[nH]c5ccccc45)C(=O)NCC(=O)NCC(=O)N[C@H](C(=O)N[C@@H](CCCCN)C(=O)NC(CCCCN)C(=O)N[C@@H](CC(N)=O)C(=O)NC(Cc4ccc(O)cc4)C(=O)N[C@@H](C)C(=O)O)[C@@H](C)CC)c3)no2)cc1]

AW9-MT

22. The antifungal peptide of claim 1, wherein the antifungal peptide has any one of the following formulas and there are more than 2 amino acids between an isoleucine residue and a asparagine residue:

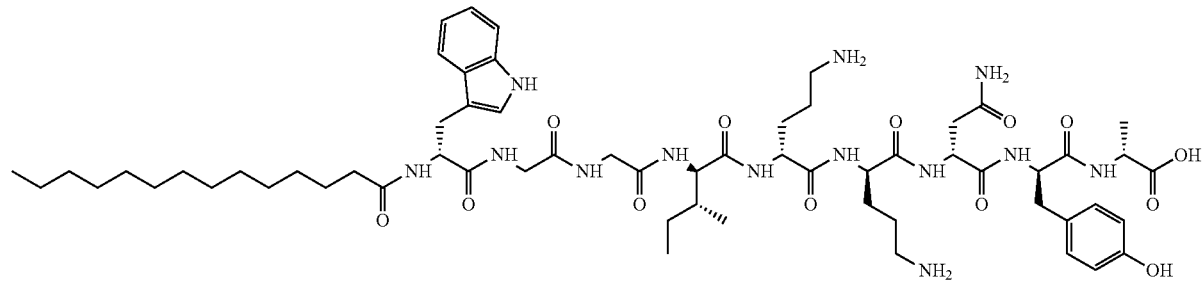
AW9-Ma-K5O; K6O-D (K5O; K6O-D)
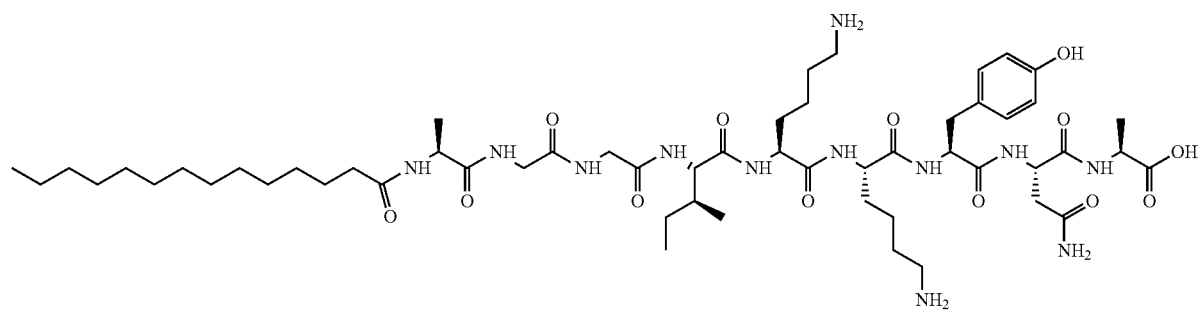
AW9-Ma-A1
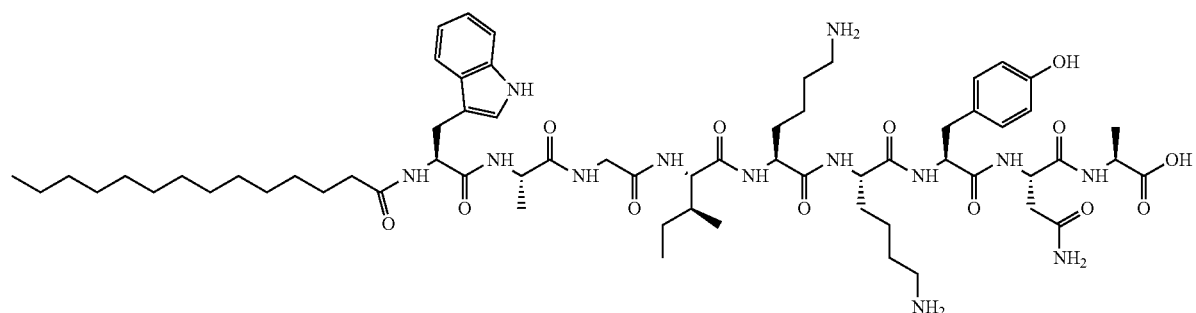
AW9-Ma-A2
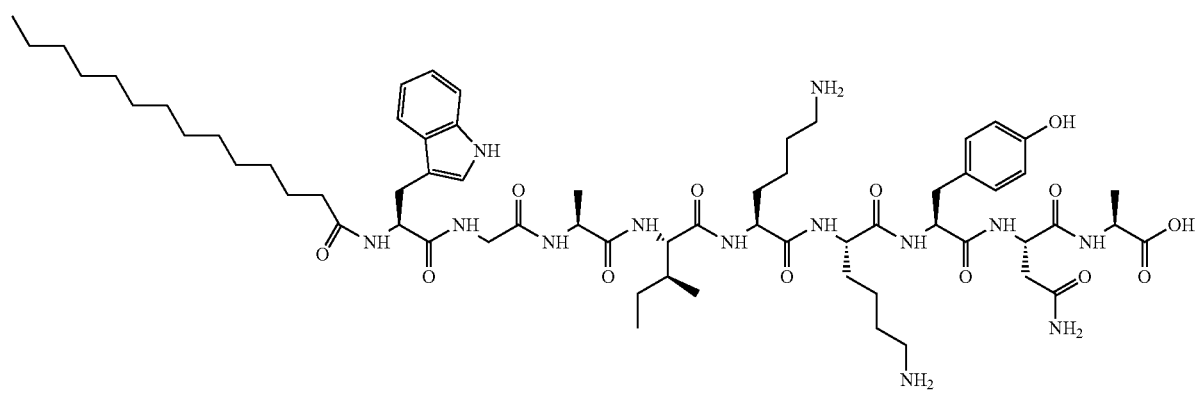
AW9-Ma-A3

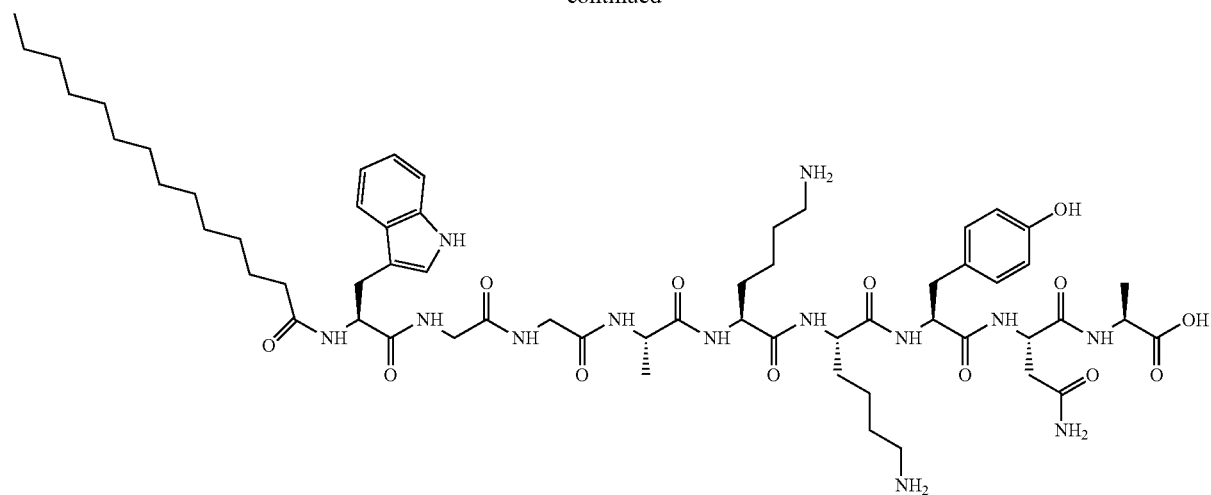
AW9-Ma-A4
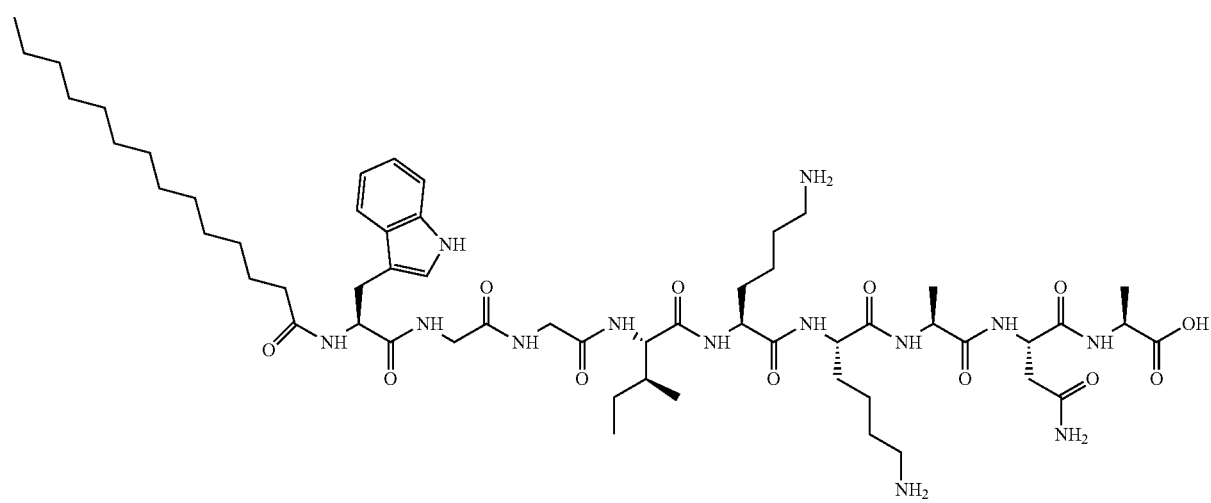
AW9-Ma-A7
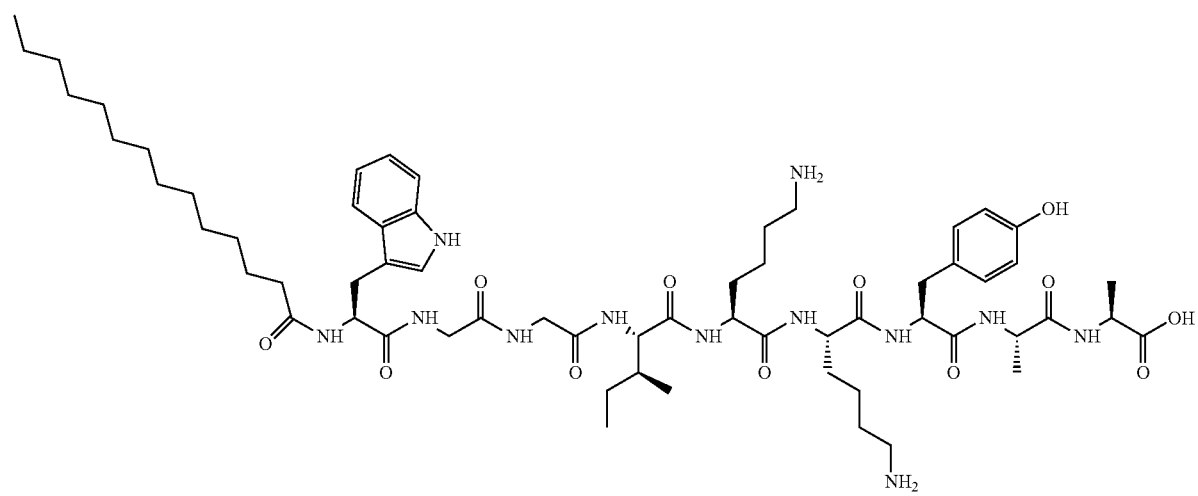
AW9-Ma-A8

-continued
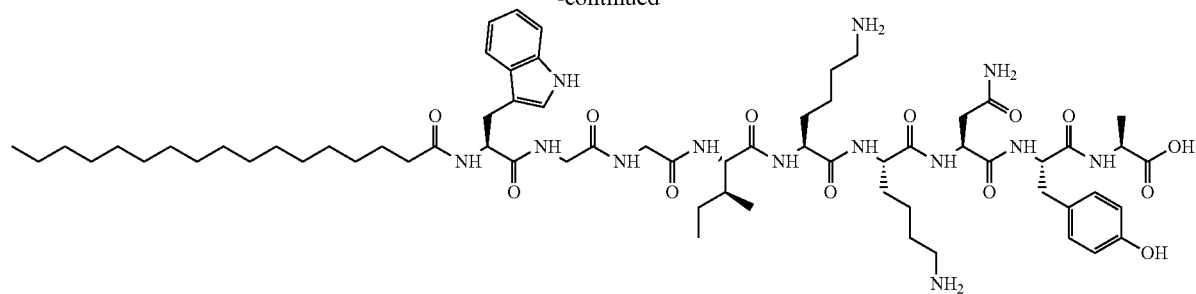
AW9-Pa
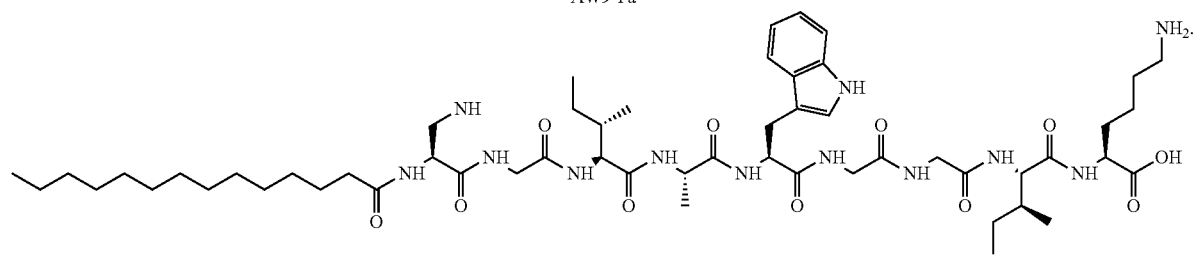
KS9-Ma
* * * * *

UNITED STATES PATENT AND TRADEMARK OFFICE
CERTIFICATE OF CORRECTION

PATENT NO. : 11,939,402 B2
APPLICATION NO. : 18/128062
DATED : March 26, 2024
INVENTOR(S) : Gregory R. Wiedman, Robert J. Tancer and Chaoyang Xue It is certified that error appears in the above-identified patent and that said Letters Patent is hereby corrected as shown below:

In the Specification

Column 1, Line 12, add the following:
Government Statement
This invention was made with government support under grant number AI155647 awarded by the National Institutes of Health. The government has certain rights in the invention.**

Signed and Sealed this
Eleventh Day of June, 2024

Katherine Kelly Vidal
*Director of the United States Patent and Trademark Office*